(12) United States Patent
Rathbun et al.

(10) Patent No.: US 10,368,927 B2
(45) Date of Patent: Aug. 6, 2019

(54) BONE PLATE WITH CAPTIVE CLIPS

(71) Applicant: DePuy Synthes Products, Inc., Raynham, MA (US)

(72) Inventors: David S. Rathbun, Gap, PA (US); Sean S. Suh, Plymouth Meeting, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 547 days.

(21) Appl. No.: 15/168,619

(22) Filed: May 31, 2016

(65) Prior Publication Data
US 2016/0346021 A1 Dec. 1, 2016

Related U.S. Application Data

(63) Continuation of application No. 13/026,110, filed on Feb. 11, 2011, now Pat. No. 9,408,646, which is a
(Continued)

(51) Int. Cl.
A61B 17/80 (2006.01)
A61B 17/17 (2006.01)
A61B 17/86 (2006.01)

(52) U.S. Cl.
CPC ...... *A61B 17/8047* (2013.01); *A61B 17/1728* (2013.01); *A61B 17/1757* (2013.01);
(Continued)

(58) Field of Classification Search
CPC ............ A61B 17/8047; A61B 17/1728; A61B 17/8605; A61B 17/1757
See application file for complete search history.

(56) References Cited

U.S. PATENT DOCUMENTS 408,080 A 7/1889 Carroll
424,836 A 4/1890 Thompson
(Continued)

FOREIGN PATENT DOCUMENTS

CH 655646 5/1986
CN 200136708 12/2000
(Continued)

OTHER PUBLICATIONS

Chinese Patent Application No. 200480025309: Chinese Official Action dated Aug. 6 2007 with English translation.
(Continued)

*Primary Examiner* — Andrew Yang
(74) *Attorney, Agent, or Firm* — BakerHostetler

(57) ABSTRACT

A fixation system includes a plate comprising a top surface, a bottom surface, a central longitudinal axis, at least one fixation hole extending between the top and bottom surfaces and comprising an undercut therein, and at least one passage intersecting one of the undercuts. At least one resilient clip is disposed in at least a portion of the undercut, with the at least one clip having a pair of generally parallel sides and an end tab. At least one fastener is provided and comprises a head and a threaded shaft, with the head comprising a perimetral groove extending around at least a portion thereof and an instrument receiving portion. The at least one clip is configured and dimensioned to seat in the undercut with the end tab extending within the passage, and the at least one fastener is configured and dimensioned to be received in the at least one fixation hole and securable therein when the at least one clip abuts the perimetral groove of the head.

20 Claims, 70 Drawing Sheets

Related U.S. Application Data continuation of application No. 11/242,660, filed on Oct. 3, 2005, now Pat. No. 7,909,860, which is a continuation-in-part of application No. 10/653,164, filed on Sep. 3, 2003, now Pat. No. 7,857,839.

(52) U.S. Cl.
CPC ...... *A61B 17/8004* (2013.01); *A61B 17/8605* (2013.01); *A61B 17/8009* (2013.01); *A61B 17/8085* (2013.01)

(56) References Cited

U.S. PATENT DOCUMENTS

| | | |
|---|---|---|
| 554,612 A | 2/1896 | Anderson |
| 831,592 A | 9/1906 | Ballard |
| 1,025,008 A | 4/1912 | Miner |
| 1,150,114 A | 8/1915 | Hays |
| 1,200,797 A | 10/1916 | Barbe |
| 1,831,813 A | 11/1931 | Levedahl |
| 2,151,919 A | 3/1939 | Jacobson |
| 2,181,746 A | 11/1939 | Siebrandt |
| 2,200,120 A | 5/1940 | Nauth |
| 2,268,515 A | 12/1941 | Olson et al. |
| 2,317,319 A | 4/1943 | West et al. |
| 2,372,888 A | 4/1945 | Edward |
| 2,393,606 A | 1/1946 | Brush |
| 2,406,832 A | 9/1946 | Hardinge |
| 2,424,485 A | 7/1947 | Miller |
| 2,486,303 A | 10/1949 | Longfellow |
| 2,494,229 A | 1/1950 | Collison |
| 2,607,339 A | 8/1952 | Price |
| 2,612,073 A | 9/1952 | Foster |
| 2,670,637 A | 2/1954 | Edmunds |
| 2,674,906 A | 4/1954 | Timpner |
| 2,782,827 A | 2/1957 | Joseph |
| 2,785,726 A | 3/1957 | Brush |
| 2,906,311 A | 9/1959 | Boyd |
| 2,972,367 A | 2/1961 | Wootton |
| 3,062,253 A | 11/1962 | Melvin |
| 3,068,869 A | 12/1962 | Sheldon et al. |
| 3,071,030 A | 1/1963 | Larry |
| 3,244,170 A | 4/1966 | McElvenny |
| 3,272,249 A | 9/1966 | Houston |
| 3,350,103 A | 10/1967 | Ahlstone |
| 3,409,058 A | 11/1968 | La et al. |
| 3,449,799 A | 6/1969 | Bien |
| 3,498,351 A | 3/1970 | Edwards et al. |
| 3,540,322 A | 11/1970 | Swanson |
| 3,547,114 A | 12/1970 | Haboush |
| 3,561,075 A | 2/1971 | Selinko |
| 3,566,947 A | 3/1971 | Jukes |
| 3,579,831 A | 5/1971 | Stevens et al. |
| 3,604,414 A | 9/1971 | Borges |
| 3,659,595 A | 5/1972 | Haboush |
| 3,707,303 A | 12/1972 | Petri |
| 3,727,611 A | 4/1973 | Schultz |
| 3,810,703 A | 5/1974 | Pasbrig |
| 3,867,932 A | 2/1975 | Huene |
| 3,896,867 A | 7/1975 | Gill et al. |
| 3,899,897 A | 8/1975 | Boerger et al. |
| 3,945,671 A | 3/1976 | Gerlach |
| 4,017,946 A | 4/1977 | Soja |
| 4,056,301 A | 11/1977 | Norden |
| 4,119,092 A | 10/1978 | Gil |
| 4,123,132 A | 10/1978 | Hardy |
| 4,270,248 A | 6/1981 | Akashi |
| 4,278,120 A | 7/1981 | Hart et al. |
| 4,280,875 A | 7/1981 | Werres |
| 4,285,377 A | 8/1981 | Hart |
| 4,288,902 A | 9/1981 | Franz |
| 4,297,063 A | 10/1981 | Hart |
| 4,299,902 A | 11/1981 | Soma et al. |
| 4,325,665 A | 4/1982 | Jukes |
| 4,352,589 A | 10/1982 | Allison et al. |
| 4,388,921 A | 6/1983 | Sutter et al. |
| 4,450,835 A | 5/1984 | Asnis et al. |
| RE31,628 E | 7/1984 | Allgower et al. |
| 4,465,065 A | 8/1984 | Gotfried |
| 4,484,570 A | 11/1984 | Sutter et al. |
| 4,488,543 A | 12/1984 | Tornier |
| 4,493,317 A | 1/1985 | Klaue |
| 4,513,744 A | 4/1985 | Klaue |
| 4,553,890 A | 11/1985 | Gulistan |
| 4,611,581 A | 9/1986 | Steffee |
| 4,640,524 A | 2/1987 | Sedlmair |
| 4,646,413 A | 3/1987 | Nall et al. |
| 4,648,768 A | 3/1987 | Hambric |
| 4,657,458 A | 4/1987 | Woller et al. |
| 4,668,134 A | 5/1987 | Vindez |
| D291,246 S | 8/1987 | Lower |
| 4,696,290 A | 9/1987 | Steffee |
| 4,708,377 A | 11/1987 | Hunting |
| 4,711,760 A | 12/1987 | Blaushild |
| 4,744,353 A | 5/1988 | McFarland |
| 4,763,548 A | 8/1988 | Leibinger et al. |
| 4,776,330 A | 10/1988 | Chapman et al. |
| 4,787,377 A | 11/1988 | Laboureau |
| RE36,020 E | 12/1988 | Moore et al. |
| 4,788,970 A | 12/1988 | Karas et al. |
| 4,790,297 A | 12/1988 | Luque |
| 4,791,918 A | 12/1988 | Von Hasselbach |
| 4,793,335 A | 12/1988 | Frey et al. |
| 4,803,976 A | 2/1989 | Frigg et al. |
| 4,804,290 A | 2/1989 | Balsells |
| 4,812,094 A | 3/1989 | Grube |
| 4,836,196 A | 6/1989 | Park et al. |
| 4,872,451 A | 10/1989 | Moore et al. |
| 4,877,020 A | 10/1989 | Vich |
| 4,898,502 A | 2/1990 | Becher |
| 4,911,153 A | 3/1990 | Border |
| 4,913,134 A | 4/1990 | Luque |
| 4,941,781 A | 7/1990 | Becher |
| 4,943,317 A | 7/1990 | Lischka et al. |
| 4,952,107 A | 8/1990 | Dupree |
| 4,957,496 A | 9/1990 | Schmidt |
| 4,957,497 A | 9/1990 | Hoogland et al. |
| 4,969,781 A | 11/1990 | Fahrner et al. |
| 4,976,576 A | 12/1990 | Mahaney |
| 5,002,542 A | 3/1991 | Frigg |
| 5,010,783 A | 4/1991 | Sparks et al. |
| 5,017,069 A | 5/1991 | Stencel |
| 5,020,949 A | 6/1991 | Davidson et al. |
| 5,026,376 A | 6/1991 | Greenberg |
| 5,030,219 A | 7/1991 | Matsen, III et al. |
| 5,030,220 A | 7/1991 | Howland |
| 5,053,036 A | 10/1991 | Perren et al. |
| 5,054,968 A | 10/1991 | Eckman |
| 5,065,490 A | 11/1991 | Wivagg et al. |
| 5,071,293 A | 12/1991 | Wells |
| 5,096,150 A | 3/1992 | Westwood |
| 5,112,336 A | 5/1992 | Krevolin et al. |
| 5,118,235 A | 6/1992 | Dill |
| 5,122,133 A | 6/1992 | Evans |
| 5,129,899 A | 7/1992 | Small et al. |
| 5,129,903 A | 7/1992 | Luhr et al. |
| 5,133,720 A | 7/1992 | Greenberg |
| 5,147,367 A | 9/1992 | Ellis |
| 5,151,103 A | 9/1992 | Tepic et al. |
| 5,154,720 A | 10/1992 | Trott et al. |
| 5,180,382 A | 1/1993 | Frigg |
| 5,190,546 A | 3/1993 | Jervis |
| 5,207,543 A | 5/1993 | Kirma |
| 5,207,753 A | 5/1993 | Badrinath |
| 5,209,751 A | 5/1993 | Farris et al. |
| 5,234,431 A | 8/1993 | Keller |
| 5,238,342 A | 8/1993 | Stencel |
| 5,250,055 A | 10/1993 | Moore et al. |
| 5,269,784 A | 12/1993 | Mast |
| 5,281,056 A | 1/1994 | Lawson et al. |
| 5,290,288 A | 3/1994 | Vignaud et al. |
| 5,304,021 A | 4/1994 | Oliver et al. |
| 5,306,278 A | 4/1994 | Dahl et al. |
| 5,312,412 A | 5/1994 | Whipple |

(56) References Cited

U.S. PATENT DOCUMENTS

| | | |
|---|---|---|
| 5,324,290 A | 6/1994 | Zdeblick et al. |
| 5,324,295 A | 6/1994 | Shapiro |
| 5,330,535 A | 7/1994 | Moser et al. |
| 5,342,363 A | 8/1994 | Richelsoph |
| 5,344,422 A | 9/1994 | Frigg |
| 5,364,399 A | 11/1994 | Lowery et al. |
| 5,368,593 A | 11/1994 | Stark |
| 5,380,323 A | 1/1995 | Howland |
| 5,385,583 A | 1/1995 | Cotrel |
| 5,387,212 A | 2/1995 | Yuan et al. |
| D357,534 S | 4/1995 | Hayes |
| 5,403,136 A | 4/1995 | Mathys |
| 5,409,493 A | 4/1995 | Greenberg |
| 5,411,348 A | 5/1995 | Balsells |
| D359,557 S | 6/1995 | Hayes |
| 5,423,819 A | 6/1995 | Small et al. |
| 5,423,826 A | 6/1995 | Coates et al. |
| 5,429,641 A | 7/1995 | Gotfried |
| 5,437,669 A | 8/1995 | Yuan et al. |
| 5,437,677 A | 8/1995 | Shearer et al. |
| 5,458,602 A | 10/1995 | Goble et al. |
| 5,470,333 A | 11/1995 | Ray |
| 5,478,342 A | 12/1995 | Kohrs |
| 5,480,440 A | 1/1996 | Kambin |
| 5,484,439 A | 1/1996 | Olson et al. |
| 5,484,446 A | 1/1996 | Burke et al. |
| 5,486,176 A | 1/1996 | Hildebrand et al. |
| 5,487,744 A | 1/1996 | Howland |
| 5,498,263 A | 3/1996 | DiNello et al. |
| 5,501,684 A | 3/1996 | Schlapfer |
| 5,507,801 A | 4/1996 | Gisin et al. |
| 5,527,315 A | 6/1996 | Jeanson et al. |
| 5,531,745 A | 7/1996 | Ray |
| 5,531,747 A | 7/1996 | Ray |
| 5,531,751 A | 7/1996 | Schultheiss et al. |
| 5,534,032 A | 7/1996 | Hodorek |
| 5,540,690 A | 7/1996 | Miller et al. |
| 5,544,664 A | 8/1996 | Benderev et al. |
| 5,545,163 A | 8/1996 | Miller et al. |
| 5,545,228 A | 8/1996 | Kambin |
| 5,545,842 A | 8/1996 | Balsells |
| 5,549,612 A | 8/1996 | Yapp et al. |
| 5,570,983 A | 11/1996 | Hollander |
| 5,575,794 A | 11/1996 | Walus et al. |
| 5,578,034 A | 11/1996 | Estes |
| 5,584,839 A | 12/1996 | Gieringer |
| 5,584,887 A | 12/1996 | Kambin |
| 5,594,722 A | 1/1997 | Iida et al. |
| 5,595,193 A | 1/1997 | Walus et al. |
| 5,597,278 A | 1/1997 | Peterkort |
| 5,601,550 A | 2/1997 | Esser |
| 5,601,553 A | 2/1997 | Trebing |
| 5,601,554 A | 2/1997 | Howland et al. |
| 5,607,428 A | 3/1997 | Lin |
| 5,616,142 A | 4/1997 | Yuan et al. |
| 5,616,144 A | 4/1997 | Yapp et al. |
| 5,620,443 A | 4/1997 | Gertzbein et al. |
| 5,624,447 A | 4/1997 | Myers |
| 5,634,927 A | 6/1997 | Houston et al. |
| 5,637,112 A | 6/1997 | Moore et al. |
| 5,642,960 A | 7/1997 | Salice |
| 5,643,265 A | 7/1997 | Errico |
| 5,645,606 A | 7/1997 | Oehy et al. |
| 5,649,931 A | 7/1997 | Bryant et al. |
| D382,056 S | 8/1997 | Kammerer |
| 5,653,708 A | 8/1997 | Howland |
| 5,669,915 A | 9/1997 | Caspar et al. |
| 5,672,177 A | 9/1997 | Seldin |
| 5,676,666 A | 10/1997 | Oxland et al. |
| 5,676,667 A | 10/1997 | Hausman |
| 5,681,311 A | 10/1997 | Foley et al. |
| 5,681,312 A | 10/1997 | Yuan |
| 5,700,267 A | 10/1997 | Urbanski |
| 5,683,216 A | 11/1997 | Erbes |
| 5,702,395 A | 12/1997 | Hopf |
| 5,707,372 A | 1/1998 | Errico et al. |
| 5,709,686 A | 1/1998 | Talos |
| 5,713,900 A | 2/1998 | Benzel et al. |
| 5,722,978 A | 3/1998 | Jenkins, Jr. |
| 5,725,532 A | 3/1998 | Shoemaker |
| 5,725,588 A | 3/1998 | Errico et al. |
| 5,733,287 A | 3/1998 | Tepic |
| 5,735,853 A | 4/1998 | Olerud |
| 5,735,899 A | 4/1998 | Schwartz et al. |
| 5,741,258 A | 4/1998 | Klaue |
| 5,741,266 A | 4/1998 | Moran et al. |
| 5,743,916 A | 4/1998 | Greenberg et al. |
| 5,746,743 A | 5/1998 | Greenberg |
| 5,746,763 A | 5/1998 | Benderev et al. |
| 5,749,884 A | 5/1998 | Benderev et al. |
| 5,755,721 A | 5/1998 | Hearn |
| 5,766,221 A | 6/1998 | Benderev et al. |
| 5,769,856 A | 6/1998 | Dong et al. |
| 5,778,804 A | 7/1998 | Read |
| D397,220 S | 8/1998 | Kumar et al. |
| 5,797,918 A | 8/1998 | McGuire et al. |
| D398,996 S | 9/1998 | Simmons et al. |
| 5,800,433 A | 9/1998 | Benzel et al. |
| 5,800,435 A | 9/1998 | Errico et al. |
| 5,810,823 A | 9/1998 | Klaue |
| 5,823,286 A | 10/1998 | Ishihara et al. |
| 5,827,285 A | 10/1998 | Bramlet |
| 5,827,286 A | 10/1998 | Incavo et al. |
| 5,836,950 A | 11/1998 | Hansson |
| 5,843,082 A | 12/1998 | Yuan et al. |
| 5,851,207 A | 12/1998 | Cesarone |
| D404,126 S | 1/1999 | Asfora |
| 5,855,580 A | 1/1999 | Kreidler et al. |
| 5,873,289 A | 2/1999 | Jarvis |
| 5,876,402 A | 3/1999 | Errico et al. |
| 5,879,389 A | 3/1999 | Koshino |
| 5,888,034 A | 3/1999 | Greenberg |
| 5,895,390 A | 4/1999 | Moran et al. |
| 5,899,906 A | 5/1999 | Schenk |
| 5,902,303 A | 5/1999 | Eckhof et al. |
| 5,902,304 A | 5/1999 | Walker et al. |
| 5,904,683 A | 5/1999 | Pohndorf et al. |
| 5,910,143 A | 6/1999 | Cripe et al. |
| 5,911,758 A | 6/1999 | Oehy et al. |
| 5,913,860 A | 6/1999 | Scholl |
| 5,931,838 A | 8/1999 | Vito |
| 5,935,169 A | 8/1999 | Chan |
| 5,938,686 A | 8/1999 | Benderev et al. |
| 5,947,654 A | 9/1999 | Blankenship et al. |
| 5,951,561 A | 9/1999 | Pepper et al. |
| 5,954,722 A | 9/1999 | Bono |
| 5,957,927 A | 9/1999 | Magee et al. |
| 5,961,257 A | 10/1999 | Bettini et al. |
| 5,961,530 A | 10/1999 | Moore et al. |
| 5,964,761 A | 10/1999 | Kambin |
| 5,964,762 A | 10/1999 | Biedermann et al. |
| 5,964,763 A | 10/1999 | Incavo et al. |
| 5,976,141 A | 11/1999 | Haag |
| 5,976,145 A | 11/1999 | Kennefick, III |
| 5,997,541 A | 12/1999 | Schenk |
| 6,004,322 A | 12/1999 | Bernstein |
| 6,004,323 A | 12/1999 | Park et al. |
| 6,007,535 A | 12/1999 | Rayhack et al. |
| 6,013,083 A | 1/2000 | Bennett |
| 6,017,345 A | 1/2000 | Richelsoph |
| 6,019,767 A | 2/2000 | Howell |
| 6,030,389 A | 2/2000 | Wagner et al. |
| 6,036,696 A | 3/2000 | Lambrecht et al. |
| 6,048,344 A | 4/2000 | Schenk |
| 6,059,789 A | 5/2000 | Dinger et al. |
| 6,063,090 A | 5/2000 | Schlapfer |
| 6,066,140 A | 5/2000 | Gertzbein et al. |
| 6,066,142 A | 5/2000 | Serbousek et al. |
| 6,083,224 A | 7/2000 | Gertzbein et al. |
| 6,086,614 A | 7/2000 | Mumme |
| 6,106,526 A | 8/2000 | Harms et al. |
| 6,113,637 A | 9/2000 | Gill et al. |
| 6,117,135 A | 9/2000 | Schlapfer |
| 6,117,173 A | 9/2000 | Taddia et al. |

(56) References Cited

U.S. PATENT DOCUMENTS

| | | | |
|---|---|---|---|
| 6,136,002 A | 10/2000 | Shih et al. |
| 6,139,550 A | 10/2000 | Michelson |
| D433,506 S | 11/2000 | Asfora |
| 6,143,012 A | 11/2000 | Gausepohl |
| 6,152,927 A | 11/2000 | Farris et al. |
| 6,156,037 A | 12/2000 | LeHuec et al. |
| 6,176,861 B1 | 1/2001 | Bernstein et al. |
| 6,187,005 B1 | 2/2001 | Brace |
| 6,193,720 B1 | 2/2001 | Yuan et al. |
| 6,193,721 B1 | 2/2001 | Michelson |
| 6,193,723 B1 | 2/2001 | Cripe et al. |
| 6,206,881 B1 | 3/2001 | Frigg |
| 6,206,886 B1 | 3/2001 | Bennett |
| 6,210,415 B1 | 4/2001 | Bester |
| 6,224,602 B1 | 5/2001 | Hayes |
| 6,228,085 B1 | 5/2001 | Theken et al. |
| 6,235,033 B1 | 5/2001 | Brace |
| 6,235,034 B1 | 5/2001 | Bray, Jr. |
| 6,238,400 B1 | 5/2001 | Bays |
| 6,241,729 B1 | 6/2001 | Estes et al. |
| 6,241,731 B1 | 6/2001 | Fiz |
| 6,254,603 B1 | 7/2001 | Gertzbein et al. |
| 6,258,089 B1 | 7/2001 | Campbell et al. |
| 6,258,091 B1 | 7/2001 | Sevrain et al. |
| 6,261,291 B1 | 7/2001 | Talaber et al. |
| 6,273,889 B1 | 8/2001 | Richelsoph |
| 6,277,124 B1 | 8/2001 | Haag |
| 6,280,445 B1 | 8/2001 | Morrison et al. |
| 6,283,969 B1 | 9/2001 | Grusin et al. |
| 6,287,309 B1 | 9/2001 | Bacelli et al. |
| 6,287,313 B1 | 9/2001 | Sasso |
| 6,293,949 B1 | 9/2001 | Justis et al. |
| 6,299,616 B1 | 10/2001 | Beger |
| 6,299,644 B1 | 10/2001 | Vanderschot |
| 6,302,883 B1 | 10/2001 | Bono |
| 6,306,136 B1 | 10/2001 | Baccelli |
| 6,306,139 B1 | 10/2001 | Fuentes |
| 6,306,140 B1 | 10/2001 | Siddiqui |
| 6,309,393 B1 | 10/2001 | Tepic |
| 6,315,779 B1 | 11/2001 | Morrison et al. |
| 6,322,562 B1 | 11/2001 | Wolter |
| 6,328,738 B1 | 12/2001 | Suddaby |
| 6,330,845 B1 | 12/2001 | Meulink |
| 6,331,179 B1 | 12/2001 | Freid et al. |
| 6,342,055 B1 | 1/2002 | Eisermann et al. |
| 6,342,056 B1 | 1/2002 | Mac-Thiong et al. |
| 6,342,057 B1 | 1/2002 | Brace et al. |
| 6,355,038 B1 | 3/2002 | Pisharodi |
| 6,361,537 B1 | 3/2002 | Anderson |
| 6,371,959 B1 | 4/2002 | Trice |
| 6,379,357 B1 | 4/2002 | Bernstein et al. |
| 6,379,364 B1 | 4/2002 | Brace et al. |
| 6,383,186 B1 | 5/2002 | Michelson |
| 6,398,783 B1 | 6/2002 | Michelson |
| 6,398,785 B2 | 6/2002 | Carchidi et al. |
| 6,402,756 B1 | 6/2002 | Ralph et al. |
| 6,416,518 B1 | 7/2002 | DeMayo |
| 6,416,528 B1 | 7/2002 | Michelson |
| 6,419,678 B1 | 7/2002 | Asfora |
| 6,423,069 B1 | 7/2002 | Sellers |
| 6,428,542 B1 | 8/2002 | Michelson |
| 6,432,108 B1 | 8/2002 | Burgess et al. |
| 6,436,103 B1 | 8/2002 | Suddaby et al. |
| 6,440,136 B1 | 8/2002 | Gambale et al. |
| 6,447,512 B1 | 9/2002 | Landry et al. |
| 6,454,769 B2 | 9/2002 | Wagner |
| 6,454,771 B1 | 9/2002 | Michelson |
| 6,471,704 B2 | 10/2002 | Gertzbein et al. |
| 6,471,706 B1 | 10/2002 | Schumacher et al. |
| 6,475,190 B2 | 11/2002 | Young |
| 6,491,714 B1 | 12/2002 | Bennett |
| 6,494,913 B1 | 12/2002 | Huebner |
| 6,503,250 B2 | 1/2003 | Paul |
| 6,524,238 B2 | 2/2003 | Velikaris et al. |
| 6,524,312 B2 | 2/2003 | Landry et al. |
| 6,527,776 B1 | 3/2003 | Michelson |
| 6,533,786 B1 | 3/2003 | Needham et al. |
| 6,558,089 B2 | 5/2003 | DeBlasio |
| 6,562,046 B2 | 5/2003 | Sasso |
| 6,565,571 B1 | 5/2003 | Jackowski et al. |
| 6,575,975 B2 | 6/2003 | Brace et al. |
| 6,585,738 B1 | 7/2003 | Mangione et al. |
| 6,592,586 B1 | 7/2003 | Michelson |
| 6,599,290 B2 | 7/2003 | Bailey et al. |
| 6,602,254 B2 | 8/2003 | Gertzbein et al. |
| 6,602,255 B1 | 8/2003 | Campbell et al. |
| 6,602,256 B1 | 8/2003 | Hayes |
| 6,610,062 B2 | 8/2003 | Bailey et al. |
| 6,616,666 B1 | 9/2003 | Michelson |
| 6,620,163 B1 | 9/2003 | Michelson |
| 6,641,583 B2 | 11/2003 | Shluzas et al. |
| 6,643,265 B1 | 11/2003 | Schzukin |
| 6,645,207 B2 | 11/2003 | Dixon et al. |
| 6,645,208 B2 | 11/2003 | Apfelbaum et al. |
| 6,652,525 B1 | 11/2003 | Assaker et al. |
| 6,663,632 B1 | 12/2003 | Frigg |
| 6,666,867 B2 | 12/2003 | Ralph et al. |
| 6,669,697 B1 | 12/2003 | Pisharodi |
| 6,669,700 B1 | 12/2003 | Farris et al. |
| 6,682,530 B2 | 1/2004 | Dixon et al. |
| 6,689,133 B2 | 2/2004 | Morrison et al. |
| 6,689,134 B2 | 2/2004 | Ralph et al. |
| 6,692,503 B2 | 2/2004 | Foley et al. |
| 6,695,846 B2 | 2/2004 | Richelsoph et al. |
| 6,699,249 B2 | 3/2004 | Schlapfer et al. |
| 6,702,817 B2 | 3/2004 | Beger et al. |
| 6,712,818 B1 | 3/2004 | Michelson |
| RE38,684 E | 1/2005 | Cesarone |
| 6,872,210 B2 | 3/2005 | Hearn |
| 6,960,216 B2 | 11/2005 | Kolb et al. |
| 6,964,664 B2 | 11/2005 | Freid et al. |
| 7,001,387 B2 | 2/2006 | Farris et al. |
| 7,001,389 B1* | 2/2006 | Navarro ............ A61B 17/8047 606/281 |
| 7,008,427 B2 | 3/2006 | Sevrain |
| 7,128,744 B2 | 10/2006 | Weaver et al. |
| 7,175,624 B2 | 2/2007 | Konieczynski et al. |
| 7,186,254 B2 | 3/2007 | Dinh et al. |
| 7,220,263 B2 | 5/2007 | Cordaro |
| 7,249,544 B2 | 7/2007 | Totsu |
| 7,318,825 B2 | 1/2008 | Butler et al. |
| 7,357,804 B2 | 4/2008 | Binder, Jr. et al. |
| 7,452,361 B2 | 11/2008 | Kreidler |
| 7,637,928 B2 | 12/2009 | Fernandez |
| 7,666,185 B2 | 2/2010 | Ryan et al. |
| 7,727,265 B2 | 6/2010 | Paul |
| 7,731,721 B2 | 6/2010 | Rathbun et al. |
| 7,740,649 B2 | 6/2010 | Mosca et al. |
| 7,749,256 B2 | 7/2010 | Farris et al. |
| 7,857,839 B2 | 12/2010 | Duong et al. |
| 7,875,061 B2 | 1/2011 | Bolger et al. |
| 7,887,547 B2 | 2/2011 | Campbell et al. |
| 7,909,860 B2 | 3/2011 | Rathbun et al. |
| RE43,008 E | 12/2011 | Talaber et al. |
| 8,128,628 B2 | 3/2012 | Freid et al. |
| 8,236,034 B2 | 8/2012 | Binder et al. |
| 8,262,659 B2 | 9/2012 | Ryan et al. |
| 8,277,493 B2 | 10/2012 | Farris et al. |
| 8,287,550 B2 | 10/2012 | Campbell et al. |
| 8,388,663 B2 | 3/2013 | Bush et al. |
| 8,500,737 B2 | 8/2013 | Richelsoph et al. |
| 8,641,743 B2 | 2/2014 | Michelson |
| 8,795,340 B2 | 8/2014 | Weiman |
| 8,801,794 B2 | 8/2014 | Blain |
| 8,814,869 B2 | 8/2014 | Freid et al. |
| 8,821,552 B2 | 9/2014 | Reitzig et al. |
| 9,101,422 B2 | 8/2015 | Freid et al. |
| 9,113,965 B2 | 8/2015 | Weiman |
| 9,220,548 B2 | 12/2015 | Duong et al. |
| 9,408,646 B2 | 8/2016 | Rathbun et al. |
| 9,414,870 B2 | 8/2016 | Ryan et al. |
| 2001/0010000 A1 | 7/2001 | Gertzbein et al. |
| 2001/0014807 A1 | 8/2001 | Wagner et al. |
| 2001/0027320 A1 | 10/2001 | Sasso |

(56) References Cited

U.S. PATENT DOCUMENTS

| | | |
|---|---|---|
| 2001/0037111 A1 | 11/2001 | Dixon et al. |
| 2001/0037112 A1 | 11/2001 | Brace et al. |
| 2001/0041894 A1 | 11/2001 | Campbell et al. |
| 2001/0047172 A1 | 11/2001 | Foley et al. |
| 2002/0004661 A1 | 1/2002 | Sevrain et al. |
| 2002/0013586 A1 | 1/2002 | Justis et al. |
| 2002/0022847 A1 | 2/2002 | Ray, III et al. |
| 2002/0026194 A1 | 2/2002 | Morrison et al. |
| 2002/0029040 A1 | 3/2002 | Morrison et al. |
| 2002/0045896 A1 | 4/2002 | Michelson |
| 2002/0045897 A1 | 4/2002 | Dixon et al. |
| 2002/0045898 A1 | 4/2002 | Freid et al. |
| 2002/0045899 A1 | 4/2002 | Errico et al. |
| 2002/0055741 A1 | 5/2002 | Schlapfer et al. |
| 2002/0058939 A1 | 5/2002 | Wagner et al. |
| 2002/0065517 A1 | 5/2002 | Paul |
| 2002/0077630 A1 | 6/2002 | Lin |
| 2002/0082606 A1 | 6/2002 | Suddaby |
| 2002/0111630 A1 | 8/2002 | Ralph et al. |
| 2002/0116002 A1 | 8/2002 | Sellers |
| 2002/0120273 A1 | 8/2002 | Needham et al. |
| 2002/0128655 A1 | 9/2002 | Michelson |
| 2002/0133172 A1 | 9/2002 | Lambrecht et al. |
| 2002/0143328 A1 | 10/2002 | Shluzas et al. |
| 2002/0143336 A1 | 10/2002 | Hearn |
| 2002/0147450 A1 | 10/2002 | LeHuec et al. |
| 2002/0151896 A1 | 10/2002 | Ferree |
| 2002/0151899 A1 | 10/2002 | Bailey et al. |
| 2002/0161367 A1 | 10/2002 | Ferree |
| 2002/0169453 A1 | 11/2002 | Berger |
| 2002/0183749 A1 | 12/2002 | Burgess et al. |
| 2002/0183754 A1 | 12/2002 | Michelson |
| 2002/0183755 A1 | 12/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2002/0193795 A1 | 12/2002 | Gertzbein et al. |
| 2003/0018335 A1 | 1/2003 | Michelson |
| 2003/0028250 A1 | 2/2003 | Reiley et al. |
| 2003/0032865 A1 | 2/2003 | Estes et al. |
| 2003/0036759 A1 | 2/2003 | Musso |
| 2003/0040748 A1 | 2/2003 | Aikins et al. |
| 2003/0040749 A1 | 2/2003 | Grabowski et al. |
| 2003/0040752 A1 | 2/2003 | Kitchens |
| 2003/0040753 A1 | 2/2003 | Daum et al. |
| 2003/0045875 A1 | 3/2003 | Bertranou et al. |
| 2003/0045880 A1 | 3/2003 | Michelson |
| 2003/0050640 A1 | 3/2003 | Lee et al. |
| 2003/0055430 A1 | 3/2003 | Kim |
| 2003/0060828 A1 | 3/2003 | Michelson |
| 2003/0074001 A1 | 4/2003 | Apfelbaum et al. |
| 2003/0083661 A1 | 5/2003 | Orbay et al. |
| 2003/0083667 A1 | 5/2003 | Ralph et al. |
| 2003/0093082 A1 | 5/2003 | Campbell et al. |
| 2003/0105462 A1 | 6/2003 | Haider et al. |
| 2003/0105463 A1 | 6/2003 | Wolgen |
| 2003/0114856 A1 | 6/2003 | Nathanson et al. |
| 2003/0130661 A1 | 7/2003 | Osman |
| 2003/0135210 A1 | 7/2003 | Dixon et al. |
| 2003/0149434 A1 | 8/2003 | Paul |
| 2003/0153920 A1 | 8/2003 | Ralph et al. |
| 2003/0171752 A1 | 9/2003 | Assaker et al. |
| 2003/0187440 A1 | 10/2003 | Richelsoph et al. |
| 2003/0187442 A1 | 10/2003 | Richelsoph et al. |
| 2003/0187443 A1 | 10/2003 | Lauryssen et al. |
| 2003/0204190 A1 | 10/2003 | Li |
| 2003/0208203 A1 | 11/2003 | Lim et al. |
| 2003/0212399 A1 | 11/2003 | Dinh et al. |
| 2003/0225409 A1 | 12/2003 | Freid et al. |
| 2003/0229348 A1 | 12/2003 | Sevrain |
| 2004/0006343 A1 | 1/2004 | Sevrain |
| 2004/0019353 A1 | 1/2004 | Freid et al. |
| 2004/0030338 A1 | 2/2004 | Paul |
| 2004/0039388 A1 | 2/2004 | Biedermann et al. |
| 2004/0068319 A1 | 4/2004 | Cordaro |
| 2004/0087951 A1 | 5/2004 | Khalili |
| 2004/0092939 A1 | 5/2004 | Freid et al. |
| 2004/0097935 A1 | 5/2004 | Richelsoph et al. |
| 2004/0127899 A1 | 7/2004 | Konieczynski et al. |
| 2004/0127904 A1 | 7/2004 | Konieczynski et al. |
| 2004/0167521 A1 | 8/2004 | DeWindt |
| 2004/0186482 A1 | 9/2004 | Kolb et al. |
| 2004/0204712 A1 | 10/2004 | Kolb et al. |
| 2004/0260306 A1 | 12/2004 | Fallin et al. |
| 2005/0010227 A1 | 1/2005 | Paul |
| 2005/0015092 A1 | 1/2005 | Rathbun et al. |
| 2005/0043732 A1 | 2/2005 | Dalton |
| 2005/0049593 A1 | 3/2005 | Duong et al. |
| 2005/0049595 A1 | 3/2005 | Suh |
| 2005/0085814 A1 | 4/2005 | Sherman et al. |
| 2005/0192577 A1 | 9/2005 | Mosca et al. |
| 2007/0288010 A1 | 12/2007 | Alleyne |
| 2009/0210186 A1 | 8/2009 | Siess |
| 2010/0069967 A1 | 3/2010 | Jacene et al. |
| 2010/0094357 A1 | 4/2010 | Wallenstein et al. |
| 2011/0137344 A1 | 6/2011 | Rathbun et al. |
| 2011/0144700 A1 | 6/2011 | Konieczynski et al. |
| 2012/0065682 A1 | 3/2012 | Duong et al. |

FOREIGN PATENT DOCUMENTS

| | | |
|---|---|---|
| CN | 00136708 | 7/2002 |
| DE | 3222037 | 4/1984 |
| DE | 3539502 C1 | 2/1987 |
| DE | 3804749 A1 | 3/1989 |
| DE | 4007306 | 5/1991 |
| DE | 4238582 | 5/1994 |
| DE | 10015734 | 9/2001 |
| DE | 10044714 A1 | 4/2002 |
| EP | 0281763 | 9/1988 |
| EP | 0495488 | 7/1992 |
| EP | 0518071 | 12/1992 |
| EP | 0599640 | 6/1994 |
| EP | 504346 B1 | 5/1995 |
| EP | 0684017 | 11/1995 |
| EP | 0689799 | 1/1996 |
| EP | 0726064 | 8/1996 |
| EP | 0739610 | 10/1996 |
| EP | 0773004 | 5/1997 |
| EP | 0829240 | 3/1998 |
| EP | 897697 A1 | 2/1999 |
| EP | 0904740 | 3/1999 |
| EP | 0910297 B1 | 10/2001 |
| EP | 1169971 | 1/2002 |
| EP | 1205154 | 5/2002 |
| EP | 1250892 | 10/2002 |
| EP | 1285632 | 2/2003 |
| EP | 1346697 | 9/2003 |
| EP | 1348390 | 10/2003 |
| FR | 2674118 A1 | 9/1992 |
| FR | 2713473 | 6/1995 |
| FR | 2720623 | 12/1995 |
| FR | 2723839 A1 | 3/1996 |
| FR | 2735008 | 12/1996 |
| FR | 2763828 | 12/1998 |
| FR | 2796829 | 2/2001 |
| FR | 2810532 | 12/2001 |
| GB | 157668 A | 1/1921 |
| GB | 265592 A | 8/1927 |
| GB | 2239482 A | 7/1991 |
| GB | 2243316 | 10/1991 |
| GB | 2266246 A | 10/1993 |
| JP | 2180249 | 7/1990 |
| JP | 2236331 | 9/1990 |
| JP | 5111495 | 5/1993 |
| JP | 2001-245894 | 9/2001 |
| JP | 2003310633 | 11/2003 |
| JP | 5111495 | 1/2013 |
| WO | WO 91/07139 | 5/1991 |
| WO | WO 92/06005 | 4/1992 |
| WO | 94/16634 A1 | 8/1994 |
| WO | WO 1994/026193 A1 | 11/1994 |
| WO | WO 95/22937 | 8/1995 |
| WO | WO 95/25474 | 9/1995 |

(56) References Cited

FOREIGN PATENT DOCUMENTS

| WO | WO 1995/031941 A1 | 11/1995 |
|---|---|---|
| WO | WO 96/14802 | 5/1996 |
| WO | WO 96/20650 | 7/1996 |
| WO | WO 97/20512 | 6/1997 |
| WO | WO 97/22301 A1 | 6/1997 |
| WO | 98/01079 A1 | 1/1998 |
| WO | WO 98/11837 | 3/1998 |
| WO | WO 98/34553 | 8/1998 |
| WO | WO 99/04718 | 2/1999 |
| WO | WO 1999/009903 | 3/1999 |
| WO | WO 99/15094 | 4/1999 |
| WO | WO 1999/027864 | 6/1999 |
| WO | WO 99/52453 | 10/1999 |
| WO | WO 00/01314 | 1/2000 |
| WO | WO 00/54681 | 9/2000 |
| WO | WO 00/78238 | 12/2000 |
| WO | WO 02/02999 | 1/2002 |
| WO | WO 02/17794 A1 | 3/2002 |
| WO | WO 02/080791 | 10/2002 |
| WO | WO 2003/063714 | 8/2003 |
| WO | WO 2003/071966 | 9/2003 |
| WO | WO 2004/093702 | 11/2004 |
| WO | WO 2005/023089 | 3/2005 |
| WO | WO 2006/028971 | 3/2006 |
| WO | WO 2006/138500 | 12/2006 |
| WO | WO 2007/041638 | 4/2007 |

OTHER PUBLICATIONS

Boothroyd et al., Product Design for Manufacture and Assembly, Marcel Dekket, Inc., 1994, 64-67.
Aesculap, ABC Anterior Cervical Plating System, Advanced Biomechanical Concept, 7 pages.
Aesculap ABC Anterior Cervical Plating System Surgical Technique Ronald I. Apfelbaum M.D. contributions from José Bárbera M.D. and Wolfhard Caspar M.D. ©1999, 22 pages.
Blackstone Medical Inc. Blackstone™ Anterior Cervical Plate the Next-Generation for Easier Implantation and Reliable Performance, 4 pages.
Codman, Anterior Cervical Plate System, Technique Guide, Apr. 1997, 13 pages.
Depuy Motech™ Restoring the Natural Balance, Introducing the Profile™ Anterior Thoracolumbar Compression Plate, 1998, 2 pages.
Depuy Motech™ Restoring the Natural Balance, Introducing Peak™, Polyaxial Cervical Plate, 1998, 2 pages.
DePuy Motech AcroMed™, a Johnson & Johnson company DOC™, Ventral Cervical Stabilization, System Surgical Technique, Edward C. Benzel M.D. FACS, Hensen Yuan M.D., Aug. 1999, 8 pages.
AcroMed, DOC Ventral Cervical Stabilization System, Surgical Technique, Edward C. Benzel M.D. FACS, Hansen Yuan M.D., Feb. 1998, 8 pages.
Eurosurgical Ortho Tech REO Spineline SpineNet, The Apex of Technology Dec. 26, 2001, 13 pages.
Interpore Cross International, TPS Surgical Technique Summary, 2000, 3 pages.
Interpore Cross International, C-TEK™ Anterior Cervical Plate, Surgical Technique, 2001, 8 pages.
Interpore Cross Internationa,l, Telescopic Plate Spacer TPS™, Spinal System, Surgical Technique for the Cervical Spine, 2000, 1 page.
Medtronic Sofamor Danek, Premier Anterior Cervical Plate System, Surgical Technique, Thomas A. Zdeblick M.D., Harry N. Herkowitz M.D., 2003, 3 pages.
Medtronic Sofamor Danek, Anterior Fixation System, Surgical Technique, Thomas A. Zdeblick M.D., 1999, 2 pages.
Medtronic Sofamor Danek, Zephir™, Anterior Cervical System, Smoothly Natural, Appendix 3, Concept 17, Mar. 2000, 5 pages.
Medtronic Sofamor Danek, Zephir™, Anterior Cervical System, Smoothly Natural, Optimal Design, 6 pages.
Medtronic Sofamor Danek, Zephir™, Anterior Cervical System, Surgical Technique, Richard Assaker M.D., Mar. 2000, 12 pages.
Medtronic Sofamor Danek, Premier Anterior Cervical Plate System, 2000, 10 pages.
Medtronic Sofamor Danek, Atlantis™, Anterior Cervical Plate System, Surgical Technique, Volker K.H. Sonntag M.D., Regis W. Haid Jr. M.D., Stephen M. Papadopoulos M.D., 2000, 29 pages.
Sofamor Danek the Spine Specialist™, Atlantis™ Anterior Cervical Plate System, 1998, 4 pages.
Scient'X, PCB Cervical System, 4 pages.
Scient'X, Secuplate Surgical Technique, 4 pages.
Stryker, Reflex™ Anterior Cervical Plate, Reliable and Flexible, May 2001, 16 pages.
Sulzer Medica, Sulzer Spine Tech, Trinica™ Anterior Cervical Plate System Featuring Secure-Twist™ Anti-migration System, Aug. 2001, 4 pages.
Sulzer Medica, Sulzer Spine-Tech, Trinica™ Anterior Cervical Plate System, Surgical Technique, Featuring Secure-Twist™ Anti-migration System, Sep. 2001, 12 pages.
Synthes Spine, The Cervical Spine Locking Plate CSLP, Original Instruments and Implants of the Association the Study of Internal Fixation—OA ASIF 2000, 23 pages.
Ulrich medizintechnik, anterior distractable cage, 3 pages with English Translation.
Ulrich medizintechnik, winged anterior distraction device ADD plus, 4 pages with English Translation.
Window Cervical Stabilization System, Quick Reference Guide, 2000, 3 pages.
International Search Report, Completed Jan. 25, 2007 for PCT/US2006/038845 filed Oct. 3, 2006.
Depuy Mothech AcroMed™, Ventral Cervical Stabilization System, Aug. 1999, 8 pages.
Mooftakhar M.D. et al. "Anterior Cervical Plates: a Historical Perspective" Dept. of Neurosurgery University of Wisconsin School of Medicine Madison Wisconsin Neurosurg Focus vol. 16 (1) Article 8 Jan. 2004.
Supplementary European Search Report, completed Oct. 9, 2008 for European Application No. 04782953.6, filed Sep. 2, 2004.
Stryker—"Surgical Techniques—Alta (Registered) Lag Screw Surgical Technique" by Michael W. Chapman, 2005, 9 pages.
Steffee et al., Segmental spine plates with pedicle screw fixation, Clin Orthop (203): pp. 45-53, 1986.
Steffee and Sitkowski, Posterior lumbar interbody fusion and plates, Clin Orthop (227): pp. 99-102.
Ryan et al., Bolt-plate fixation for anterior spinal fusion, Clin Orthop (203): pp. 196-202, 1986.
Rao et al., Clinical Evaluation of the Alta Hip Bolt in Peritrochanteric Hip Fractures, Am J Orthop (Belle Mead NJ). Sep. 1998;27(9):612-6.
Ramotowski and Granowski, Zespol: An original method of stable osteosynthesis, Clin Orthop (272), 1991, pp. 67-75.
Howmedica Surgical Techniques—Digital Femoral Plating Surgical Technique by Dana C. Mears, PhD, 1995.
Howmedica Surgical Techniques—Alta Lag Screw Surgical Technique by Michael W. Chapman, 1992, 16 pages.
Howmedica 1997/78 Product Catalog.
Howmedica—your orthopaedic resource—1993 Product Catalog.
Howmedica—your orthopaedic resource—1990 Product Catalog.
Howmedica "Alta Modular Trauma System" documents, 1989 and 1991, 27 pages.
Fasteners Handbook by Julius Soled, P.E. Consulting EngineerCopyright, 1957, p. 43.
Cover page of Journal of Orthopaedic Trauma, vol. 6, No. 1, and advertisement for the Alta Modular Trauma System, 1992, 2 pages.
Alta Modular Trauma System—The Howmedica Alta Hip Bolt Surgical Technique by Michael Chapman, Jan. 1992, 20 pages.

\* cited by examiner

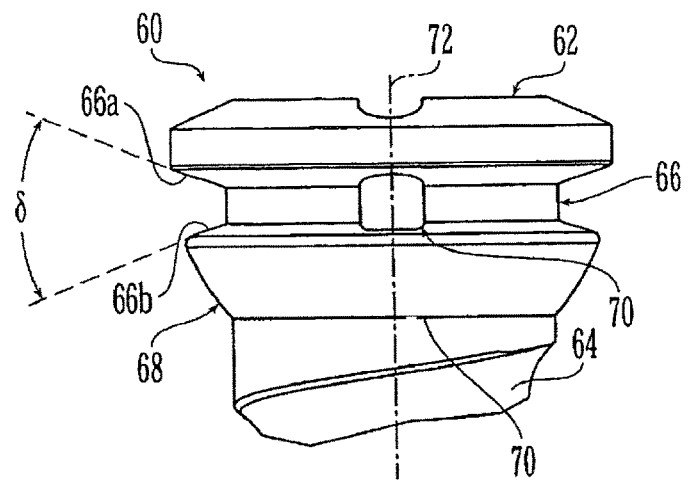
*Fig. 4D*
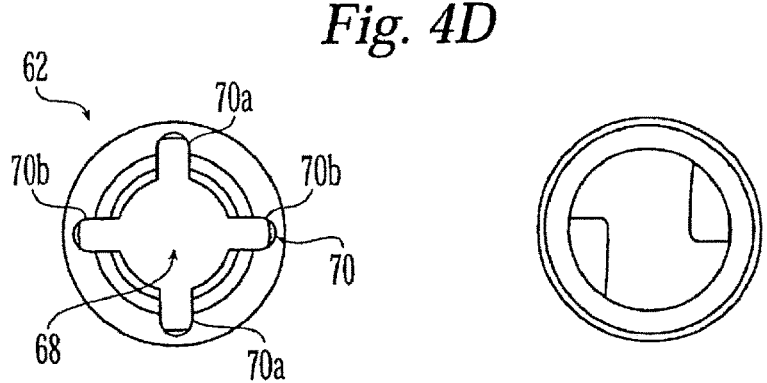
*Fig. 4E*     *Fig. 4F*
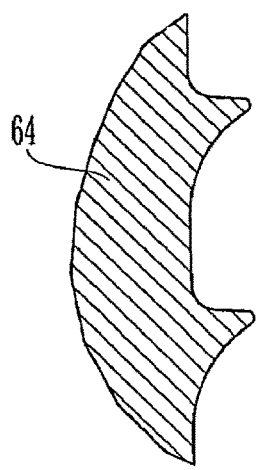
*Fig. 4G*

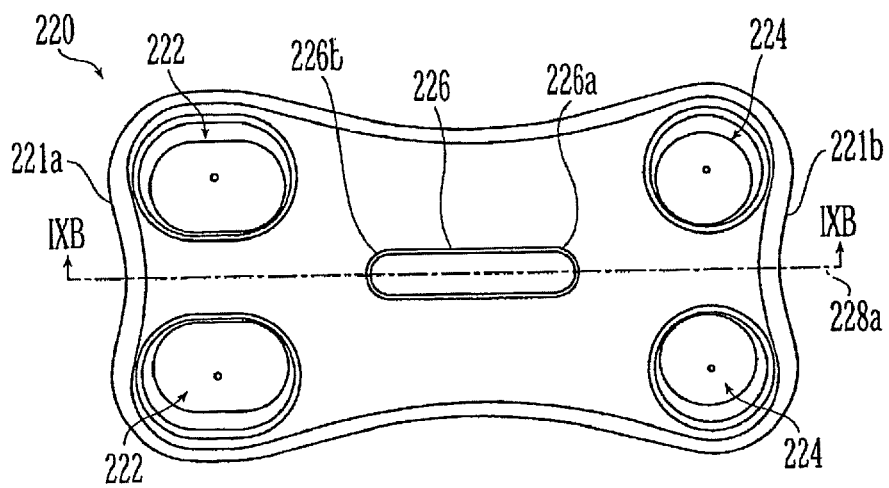
Fig. 9A
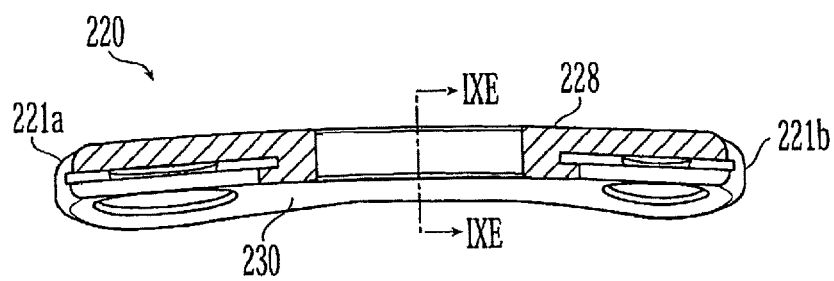
Fig. 9B
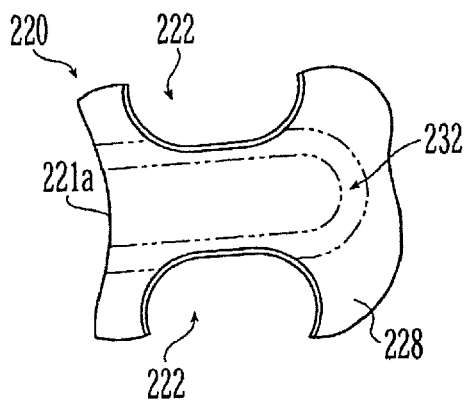 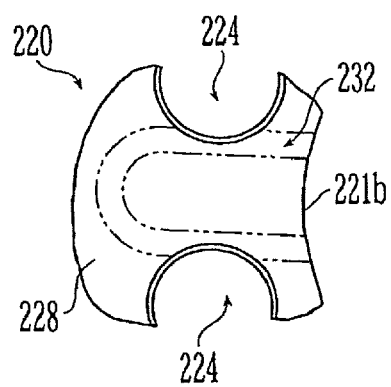
Fig. 9C  Fig. 9D

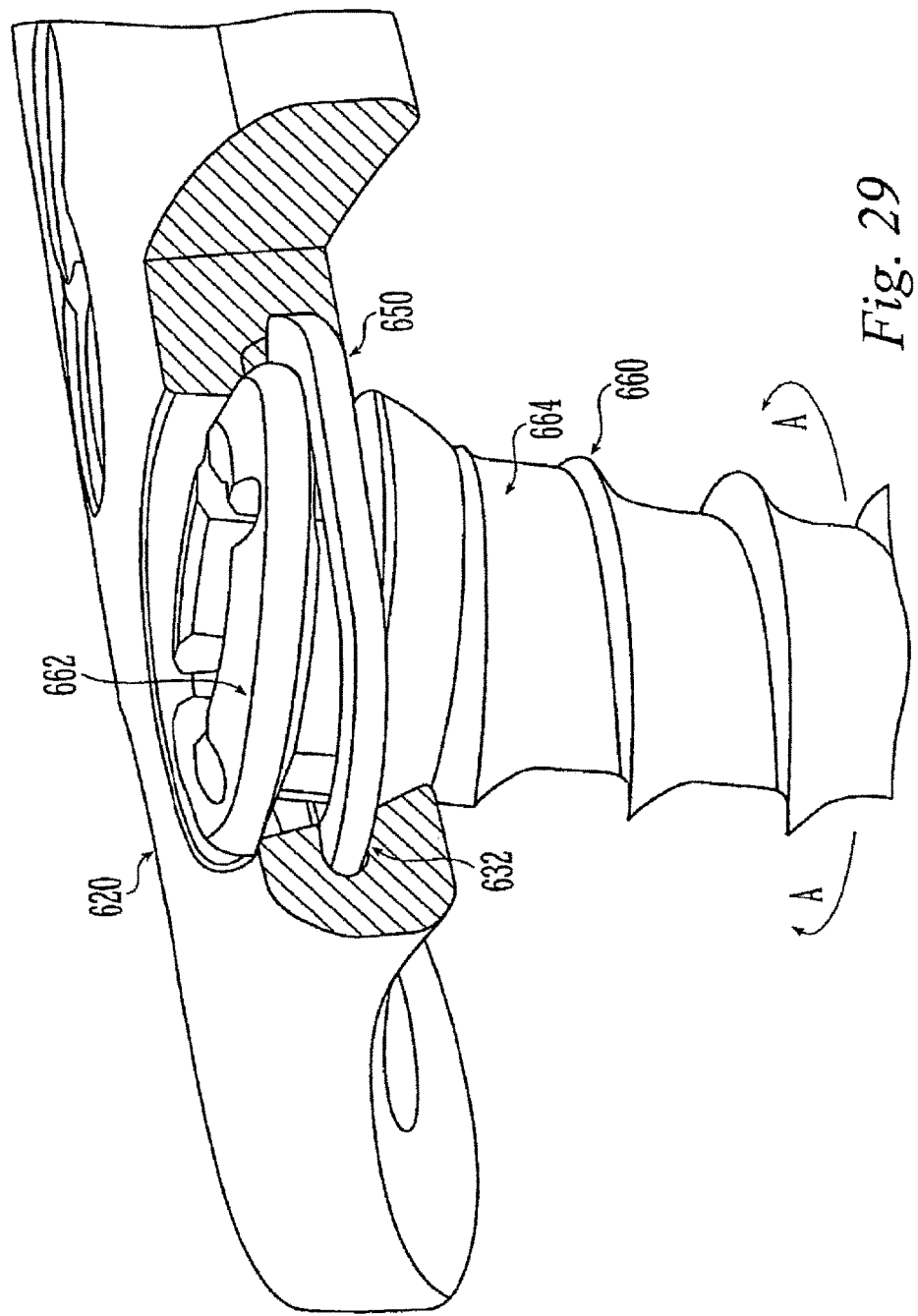

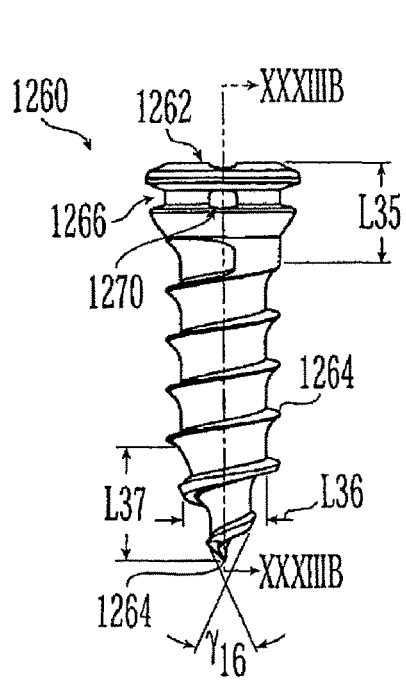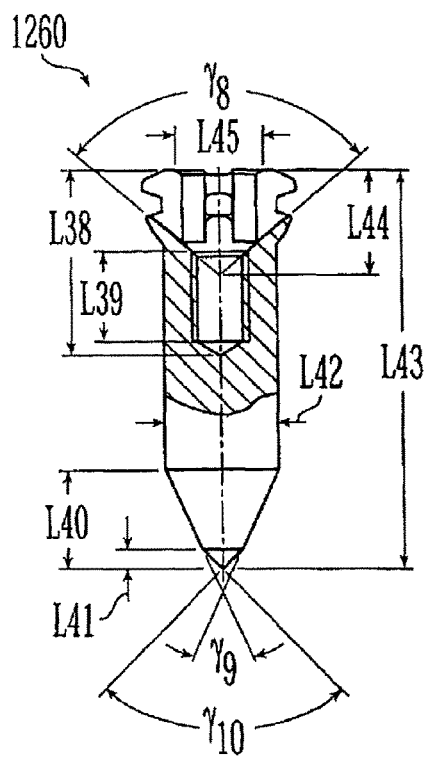
Fig. 33A    Fig. 33B
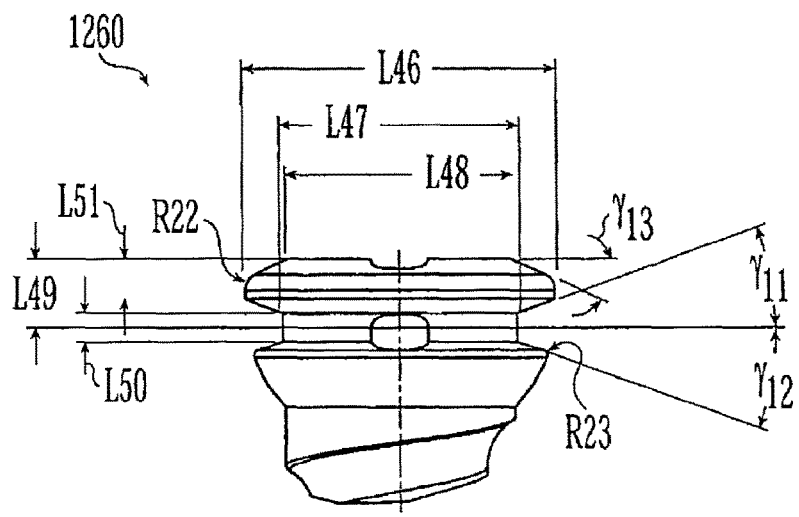
Fig. 33C

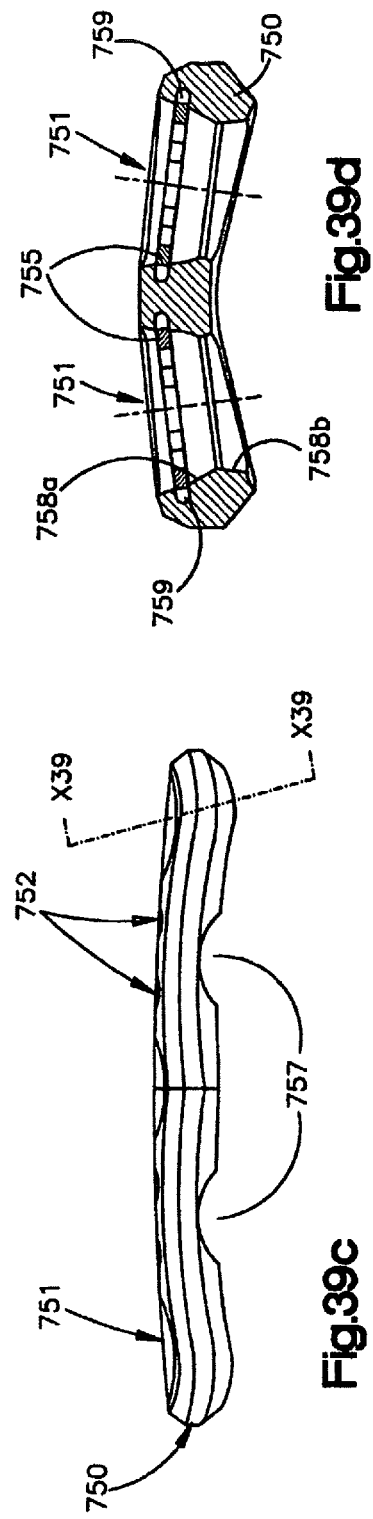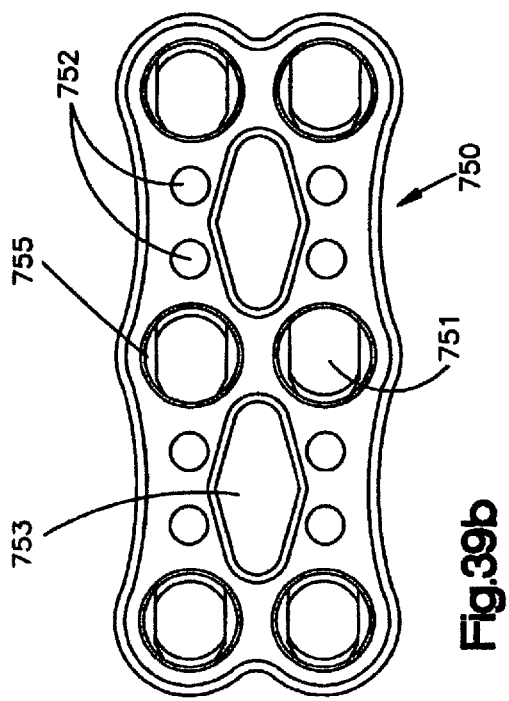

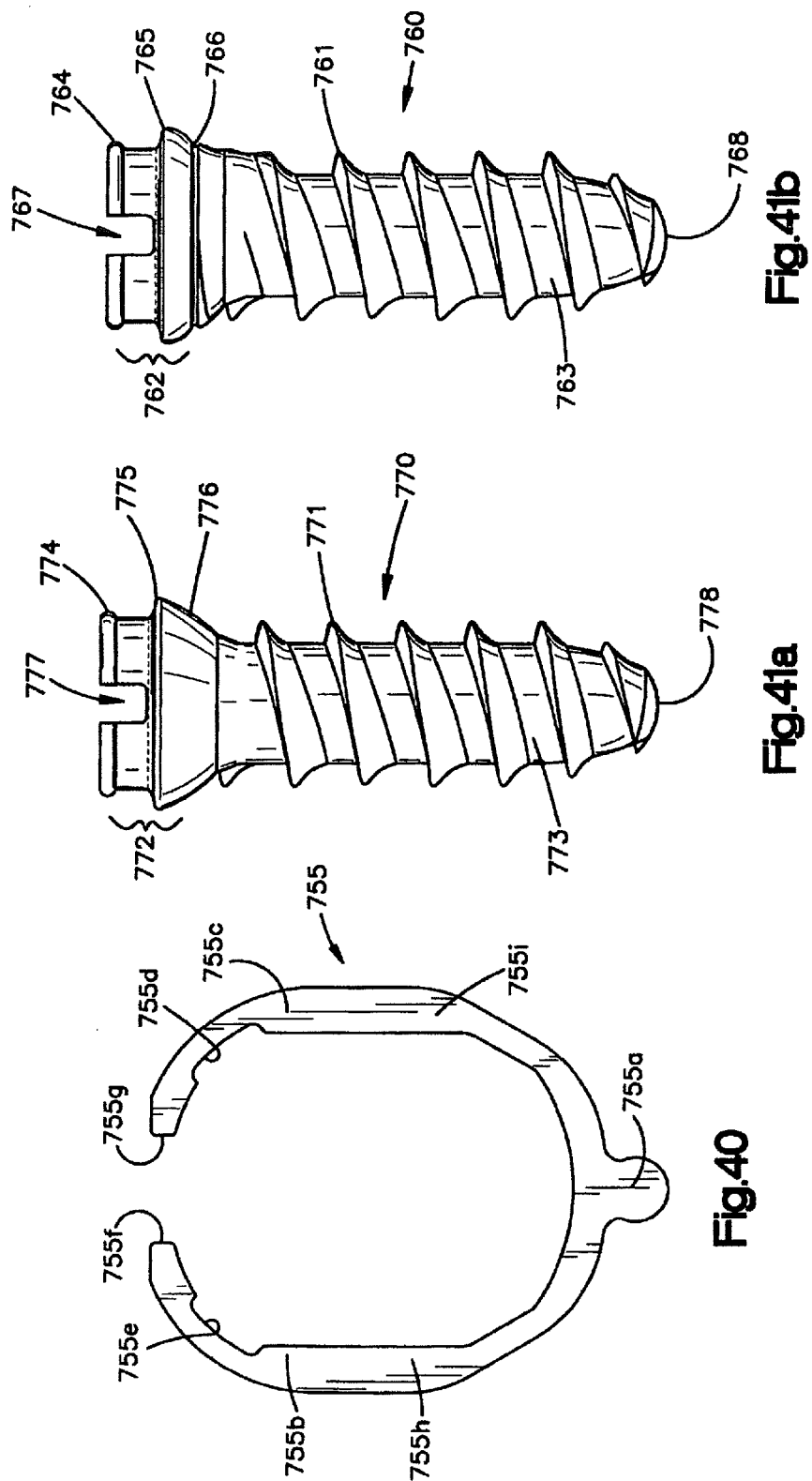

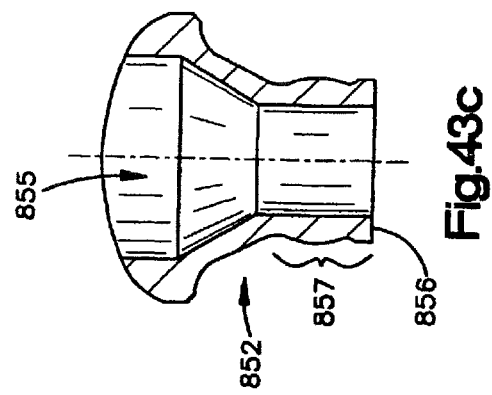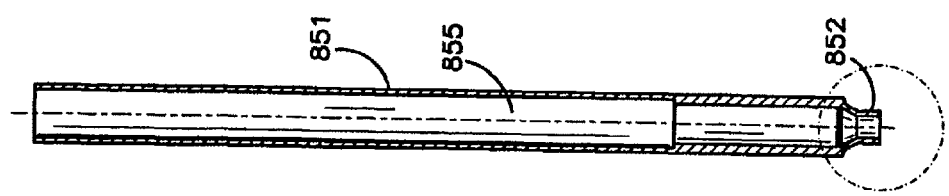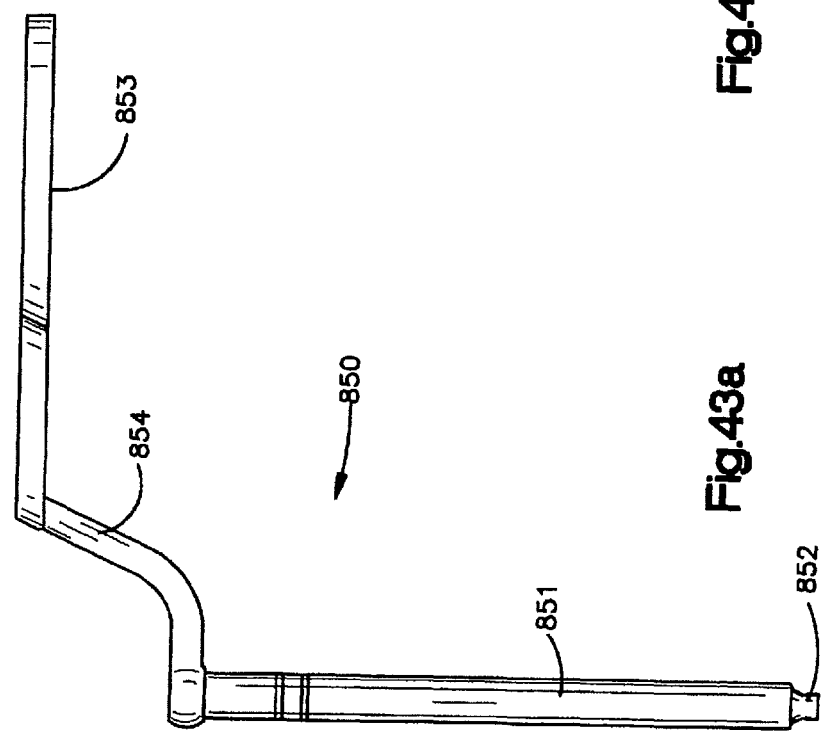

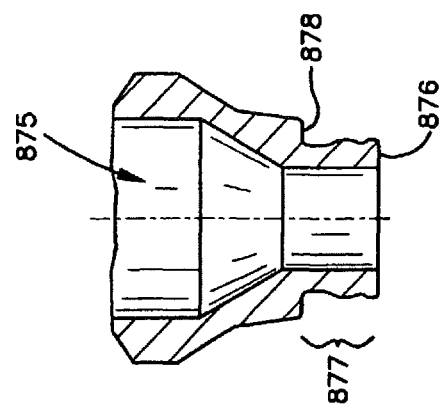
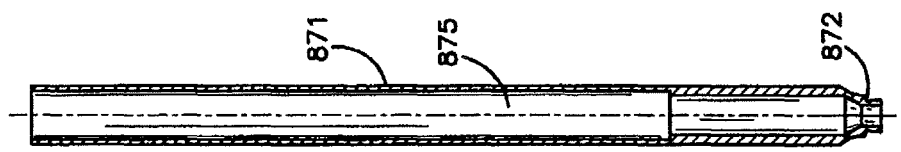
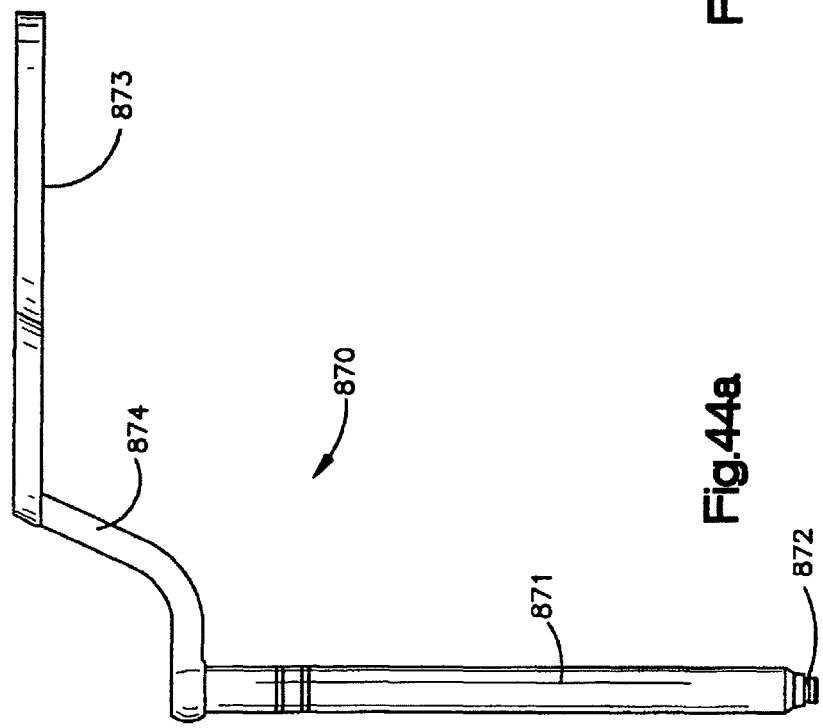

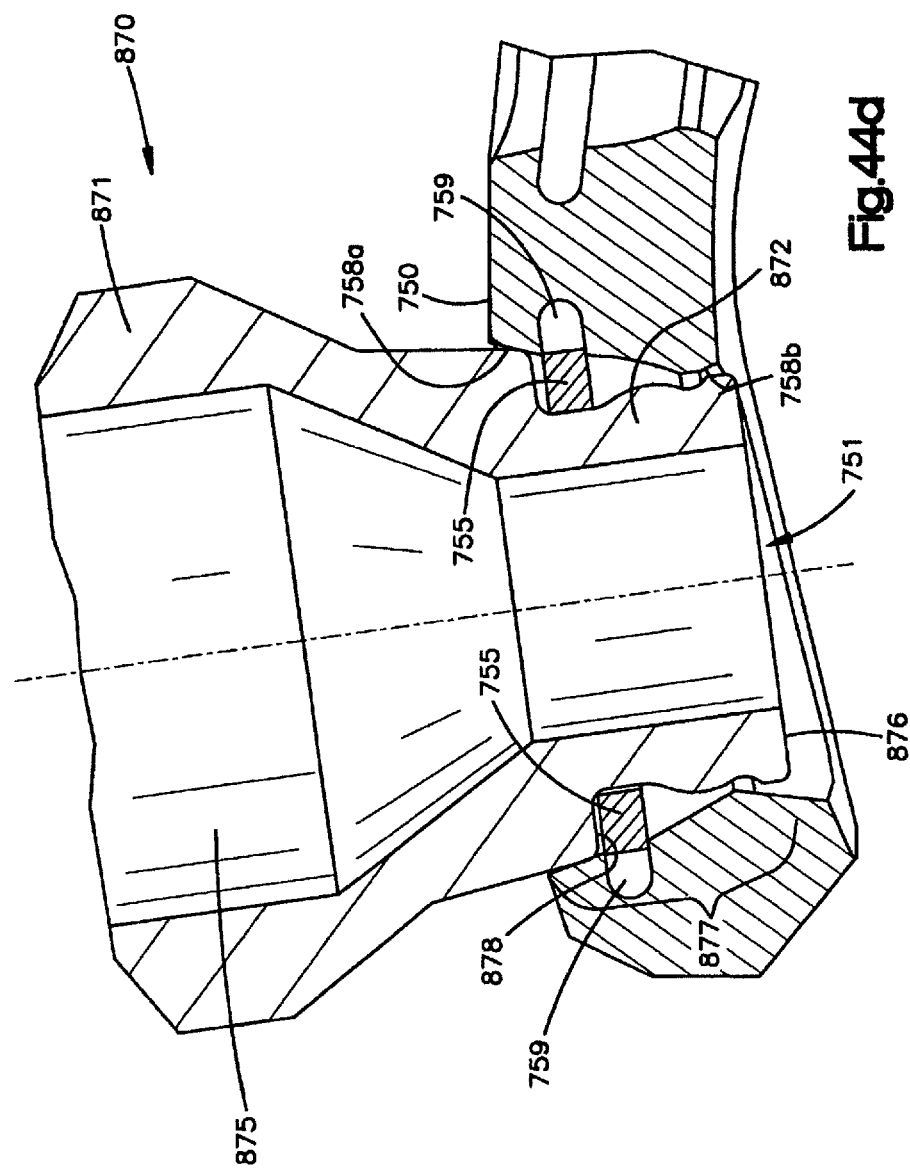

US 10,368,927 B2

BONE PLATE WITH CAPTIVE CLIPS

CROSS REFERENCE TO RELATED APPLICATIONS

This application is a continuation application of U.S. patent application Ser. No. 13/026,110, filed Feb. 11, 2011, which is a continuation application of U.S. patent application Ser. No. 11/242,660, filed Oct. 3, 2005, now U.S. Pat. No. 7,909,860, which is a continuation-in-part of U.S. patent application Ser. No. 10/653,164, filed Sep. 3, 2003, now U.S. Pat. No. 7,857,839, the entire disclosures of each being expressly incorporated herein by reference thereto.

FIELD OF THE INVENTION

The invention is related to a fixation system. More particularly, the invention is related to a plate with a clip for resisting post-operative fastener back-out.

BACKGROUND OF THE INVENTION

Orthopedic fixation devices such as plates are frequently coupled to bone with fasteners inserted through plate holes. It is known that securing such fasteners to the bone plate, for example through the use of expansion-head screws, can decrease the incidence of loosening of the fixation assembly post-operatively. It is also known that a bushing may be disposed in each plate hole to receive the fastener to permit polyaxial movement so that the fastener may be angulated at a surgeon-selected angle. However, typically as the fastener is inserted into bone through the bushing and plate hole, a threaded head of the fastener engages a threaded internal surface of the bushing to expand the bushing against the wall of the plate hole, thereby locking the screw at a given angular orientation with respect to the plate.

Despite these fixation systems, there exists a need for bone plates that allow post-operative angulation and/or movement. In particular, with respect to fixation of the spine, there exists a need for anterior cervical compression plates and associated fasteners that allow the vertebral bodies to compress over grafts post-operatively. In order for compression to occur, there exists a need for a plate/fastener construct that allows for translational and/or rotational settling that both occur post-operatively between the plate and fasteners that have been rigidly placed into vertebral bodies. More particularly, there exists a need for a fixation system that facilitates translational settling by permitting a fastener to slide within a plate hole. There further exists a need for a fixation system that facilitates rotational settling by permitting a fastener head to toggle or pivot within the plate hole. In addition, there exists a need for a fixation system that permits fastener motion associated with translational and/or rotational settling while also resisting back-out of the fastener from the plate.

SUMMARY OF THE INVENTION

The invention relates to a fixation system that includes a plate comprising a top surface, a bottom surface, a central longitudinal axis, at least one fixation hole extending between the top and bottom surfaces and comprising an undercut therein, and at least one passage intersecting one of the undercuts. At least one resilient clip is disposed in at least a portion of the undercut, with the at least one clip having a pair of generally parallel sides and an end tab. At least one fastener is provided and comprises a head and a threaded shaft, with the head comprising a perimetral groove extending around at least a portion thereof and an instrument receiving portion. The at least one clip is configured and dimensioned to seat in the undercut with the end tab extending within the passage, and the at least one fastener is configured and dimensioned to be received in the at least one fixation hole and securable therein when the at least one clip abuts the perimetral groove of the head.

The fixation system may further comprise a slot extending through the central longitudinal axis. The slot may be aligned along the central longitudinal axis or may be disposed transverse to the central longitudinal axis. The slot may include a dog-bone shape or the slot may include a pair of overlapping circular shapes. Also, the at least one passage may extend transverse to at least one of the fixation holes.

The instrument receiving portion of the head of the at least one fastener may at least partially intersect the undercut. A portion of the undercut may be disposed closer to the top surface than the bottom surface, and may extend completely around the at least one fixation hole.

Each of the fixation holes may further include a lower portion disposed between the bottom surface and the undercut, with the lower portion tapering toward a central axis of the fixation hole. The taper of the lower portion may be semispherical. The lower portion also may have a first maximum inner dimension and the undercut may have a second maximum inner dimension, wherein the first maximum inner dimension is less than the second maximum inner dimension.

The head of the fastener may further include a tapered portion disposed between the threaded shaft and the perimetral groove, with the tapered portion tapering toward a central axis of the fastener.

At least one fixation hole may be circular. Also, the plate may include at least two pairs of fixation holes. One pair of fixation holes may be generally circular and the other pair of fixation holes may be generally oblong.

In addition, the perimetral groove of the fastener may be interrupted by at least one corner, at least two corners, or at least four corners. Each corner may be configured and dimensioned as a cam to abut an inner wall of the clip. The perimetral groove of the fastener may include an upper surface and a lower surface disposed at between about 10° and about 70° with respect to each other. In some embodiments, the perimetral groove includes an upper surface and a lower surface disposed at between about 30° and about 50° with respect to each other, and in some embodiments, the perimetral groove includes an upper surface and a lower surface aligned at about 40° with respect to each other.

The instrument receiving portion of the head of the at least one fastener may intersect the perimetral groove in at least one location, at least two locations, or at least four locations. The instrument receiving portion of the head of the at least one fastener may have two substantially perpendicular slots. Also, the instrument receiving portion may include an internal thread that may extend within the shaft.

The clip may be generally wishbone-shaped. In some embodiments, the clip includes a generally circular portion or a generally arcuate portion. The clip may also include a discontinuity. In some embodiments the clip may be configured and dimensioned to slide in the undercut, while in other embodiments the clip may be configured and dimensioned to be fixed and stationary in the plate.

The undercut of the plate may be sized to retain the clip at least partially therein while permitting expansion thereof. The at least one fixation hole may include at least two pairs of fixation holes, with at least one of the pairs of fixation holes being configured and dimensioned to permit toggling of fasteners disposed therein. The head of the fastener may be configured and dimensioned to permit toggling in the at least one fixation hole, or the head may be configured and dimensioned for coupling to the plate at a fixed angle.

The fastener may be permitted to toggle. The head of the fastener may further include at least one scallop disposed proximate a top peripheral portion of the head. In some embodiments, four scallops are provided. The at least one scallop may include an arcuate portion.

At least one surface of the head may include roughening for interacting with the clip. In some embodiments, the roughening is formed by steps on a surface.

The at least one resilient clip may be configured and dimensioned to permit toggling of the at least one fastener through a greater angular range in a cephalad-caudal direction of the plate than in other directions of the plate. In particular, the at least one resilient clip may be configured and dimensioned to permit toggling through a greater angular range in a cephalad-caudal direction of the plate than in a medial-lateral direction of the plate. Toggling of the at least one fastener may be permitted between about 0° and about 32° along a plane extending parallel to the central longitudinal axis of the plate, while toggling of the at least one fastener may be permitted between about 0° and about 20° along a plane extending perpendicular to the central longitudinal axis of the plate.

The invention also relates to a fixation system including a plate having a top surface, a bottom surface, a central longitudinal axis, and a slot extending through the central longitudinal axis. The plate may also have at least two pairs of fixation holes, with each of the fixation holes extending between the top and bottom surfaces and including an undercut therein. In addition, at least one passage may extend transverse to one of the fixation holes and intersect one of the undercuts. The fixation system may also include a resilient clip disposed in at least one of the undercuts, with the clip having a pair of generally parallel sides and an end tab. At least one fastener having a head and a threaded shaft may be provided, with the head including a perimetral groove extending around at least a portion thereof and an instrument receiving portion that at least partially intersects the groove. Each clip may be configured and dimensioned to seat in an undercut with the end tab extending within the passage, and each fastener may be configured and dimensioned to be received in one of the fixation holes and securable therein when the clip abuts the perimetral groove of the head.

BRIEF DESCRIPTION OF THE DRAWINGS

Preferred features of the present invention are disclosed in the accompanying drawings, wherein:

FIG. 4D shows a partial side view of the head of the fastener of FIG. 4A;

FIG. 4E shows a top view of the fastener of FIG. 4A;

FIG. 4F shows a bottom view of the fastener of FIG. 4A;

FIG. 4G shows a partial cross-sectional side view of the shaft and threads of the fastener of FIG. 4A;

FIG. 9A shows a top view of a plate for use with a third embodiment of a fixation system;

FIG. 9B shows a partial cross-sectional view taken along line IXB-IXB of the plate of FIG. 9A;

FIG. 9C shows a top view of end 221a of the plate of FIG. 9A;

FIG. 9D shows a top view of end 221b of the plate of FIG. 9A;

FIG. 29 shows a partial cross-sectional perspective view of the plate of FIGS. 23A, 24A, 25A, and 26A with a fastener and the captive clip of FIG. 28A installed therein;

FIG. 33A shows a side view of an embodiment of a variable angle, self-drilling fastener;

FIG. 33B shows a partial cross-sectional side view taken along line XXXIIIB-XXXIIIB of the fastener of FIG. 33A;

FIG. 33C shows a partial side view of the head of the fastener of FIG. 33A;

FIG. 34C shows a partial side view of a fixed-angle head of the fastener of FIG. 34A;

FIG. 34D shows a top view of the fastener of FIG. 34A;

FIG. 34E shows a partial cross-sectional side view taken along line XXXIVF-XXXIVF of the fastener of FIG. 34A;

FIG. 35A shows aside view of an embodiment of a fixed angle, self-drilling fastener;

FIG. 35B shows a partial cross-sectional side view taken along line XXXVB-XXXVB of the fastener of FIG. 35A;

FIG. 35C shows a partial side view of the head of the fastener of FIG. 35A;

FIG. 35D shows a top view of the fastener of FIG. 35A;

FIG. 35E shows a partial cross-sectional side view taken along line XXXVF-XXXVF of the fastener of FIG. 35A;

FIG. 36A shows a first perspective view of an embodiment of a plate having a fastener with scallops installed therewith;

FIG. 36B shows another perspective view of the embodiment of FIG. 36A;

FIG. 36C shows another perspective view of the embodiment of FIG. 36A;

FIG. 36D shows another perspective view of the embodiment of FIG. 36A;

Figure 37A:
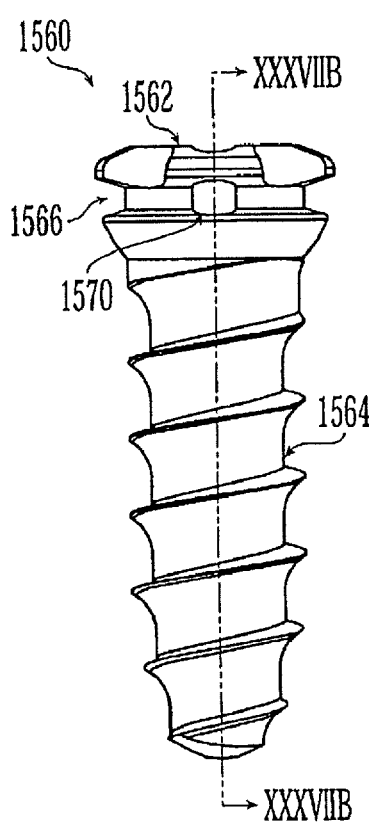
Figure 37B:
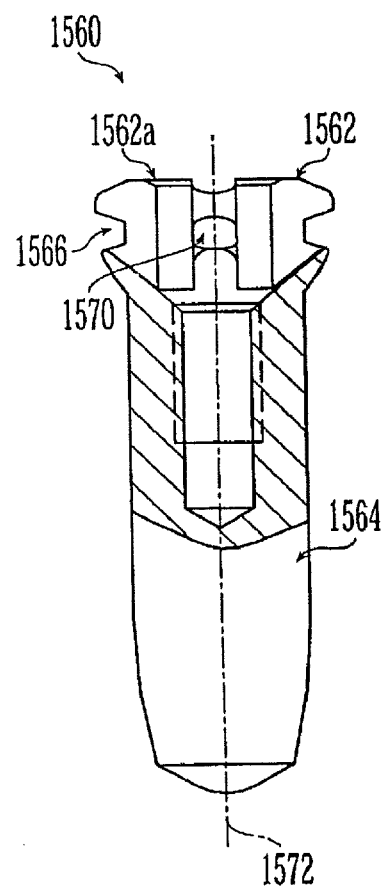
Figure 37C:
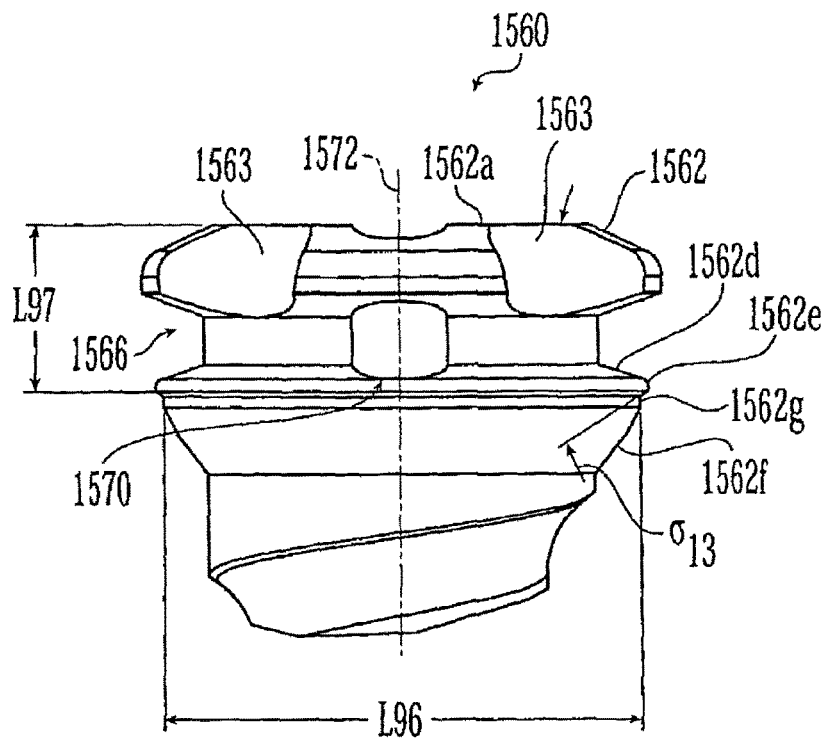
Figure 37D:
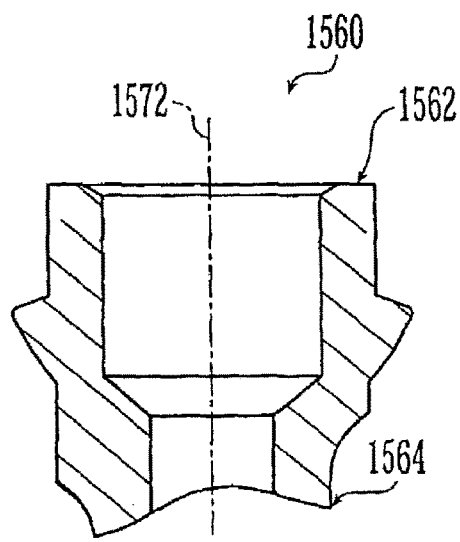
Figure 37E:
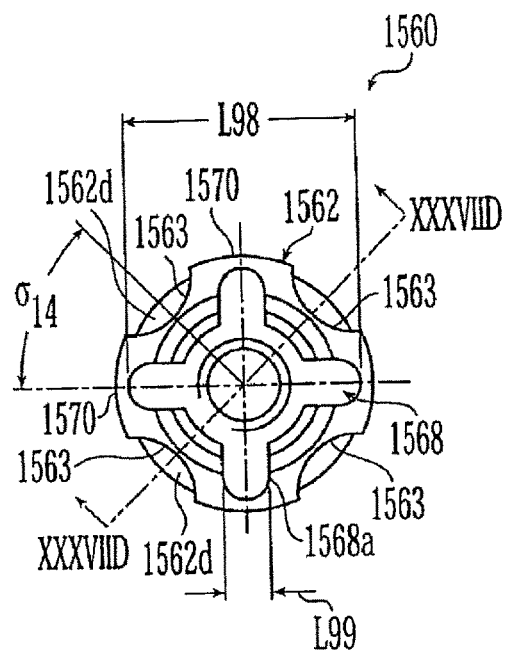
Figure 37F:
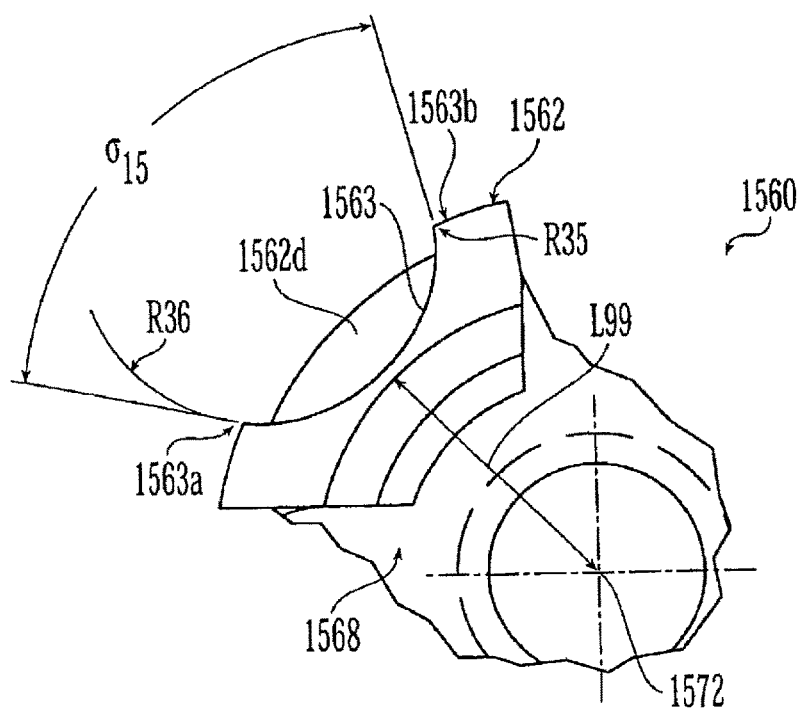

FIG. 37A shows a side view of an embodiment of a fastener;

FIG. 37B shows a partial cross-sectional side view taken along line XXXVIIB-XXXVIIB of the fastener of FIG. 37A;

FIG. 37C shows a partial side view of the head of the fastener of FIG. 37A;

FIG. 37D shows a partial cross-sectional side view taken along line XXXVIID-XXXVIID of the fastener of FIG. 37E;

FIG. 37E shows a top view of the fastener of FIG. 37A;

FIG. 37F shows a partial top view of the fastener of FIG. 37A

Figure 37G:
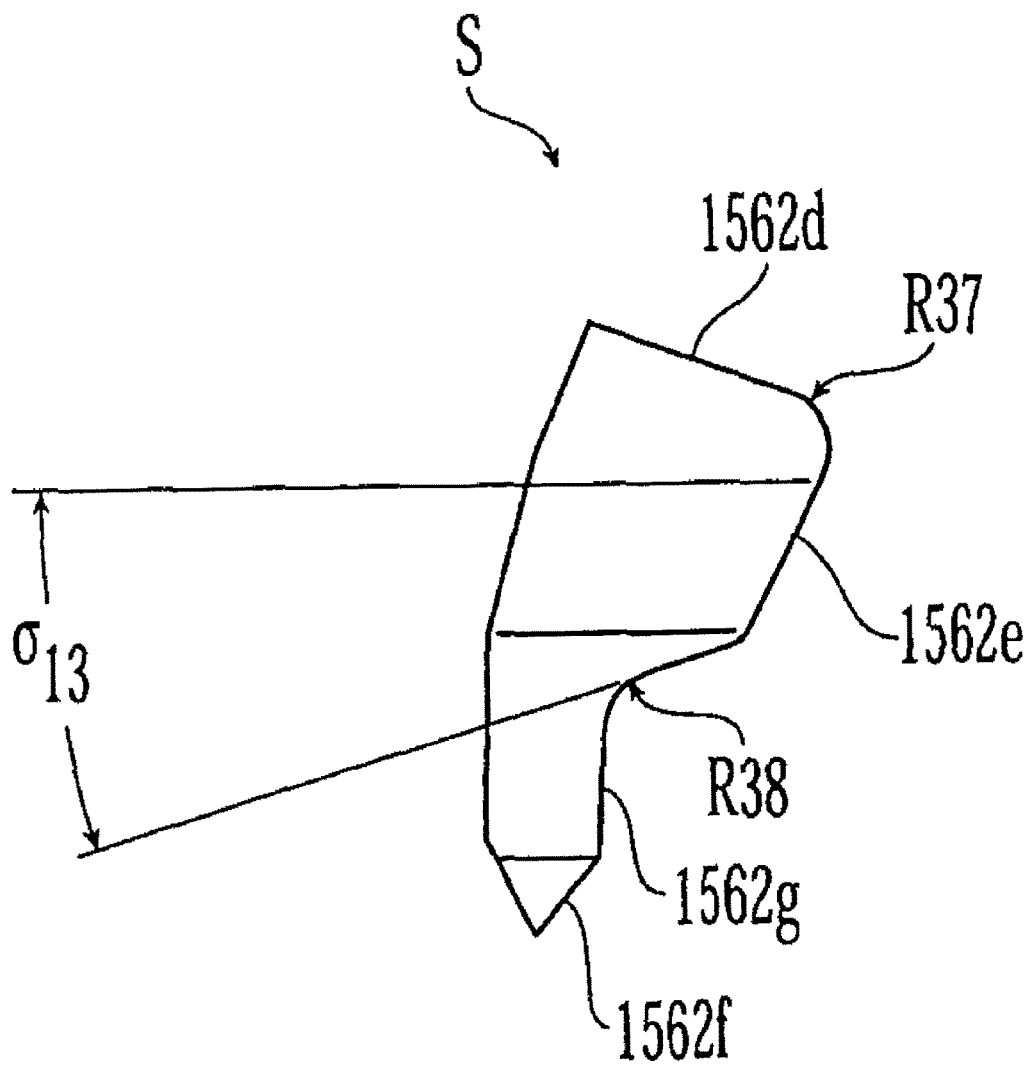
Figure 37H:
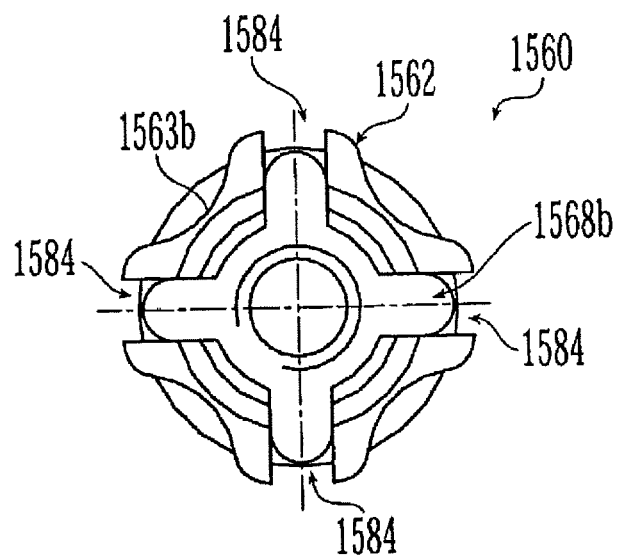
Figure 37I:
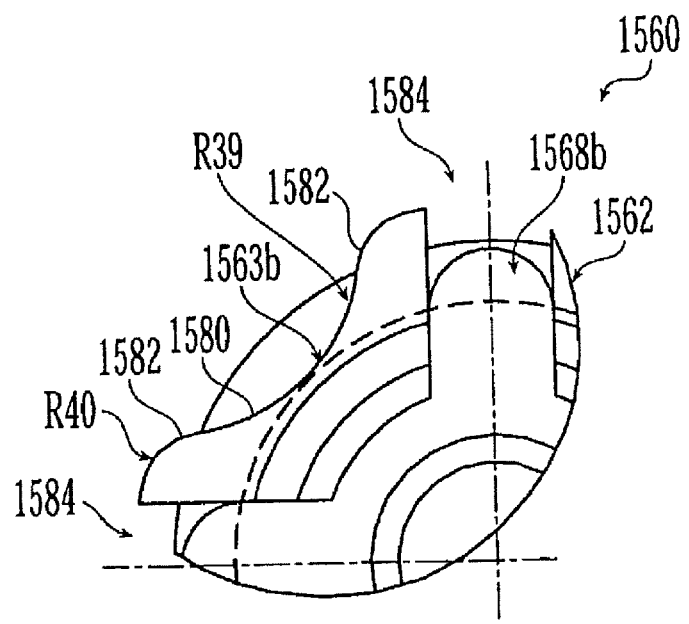
Figure 38A:
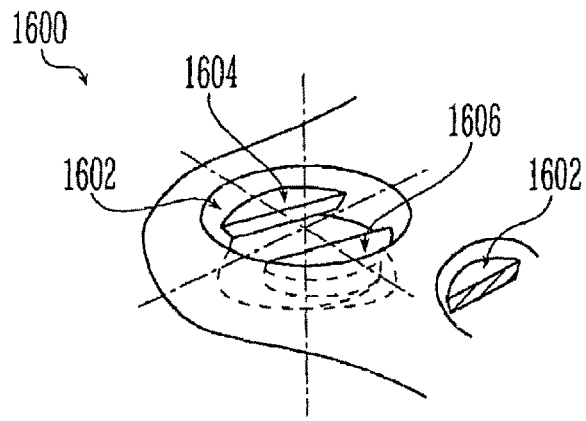
Figure 38B:
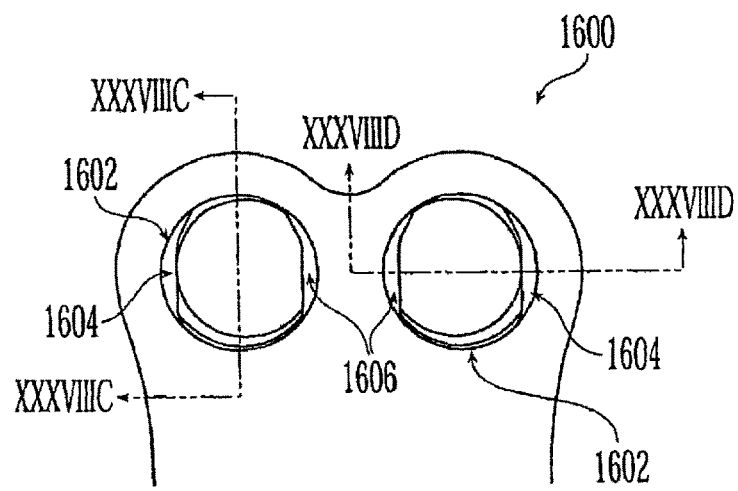
Figure 38C:
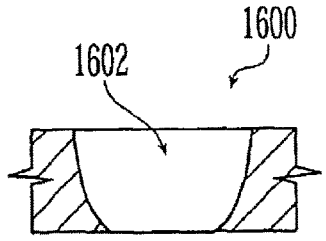
Figure 38D:
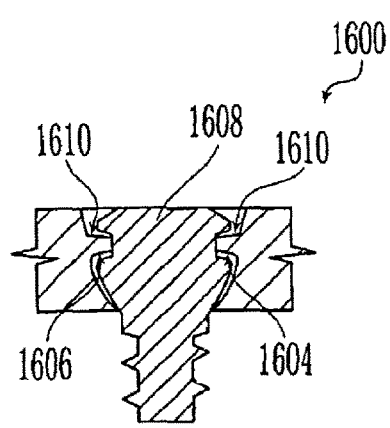
Figure 38E:
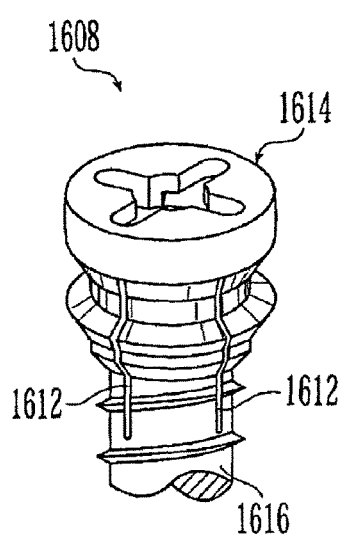
Figure 38F:
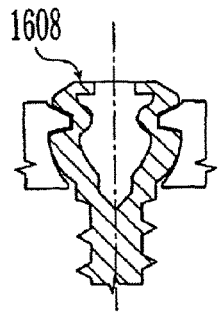
Figure 38G:
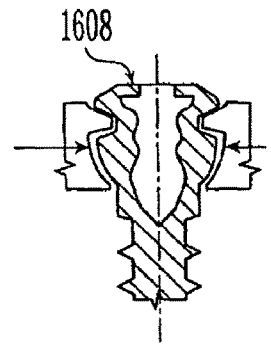
Figure 39A:
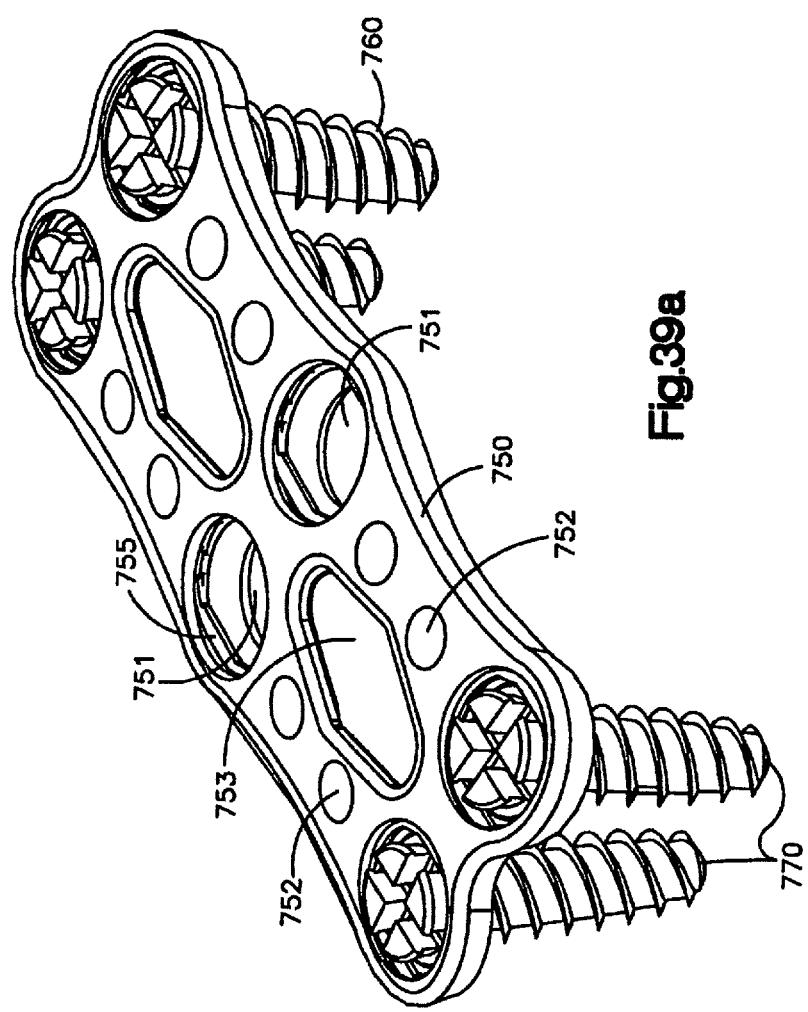
Figure 42A:
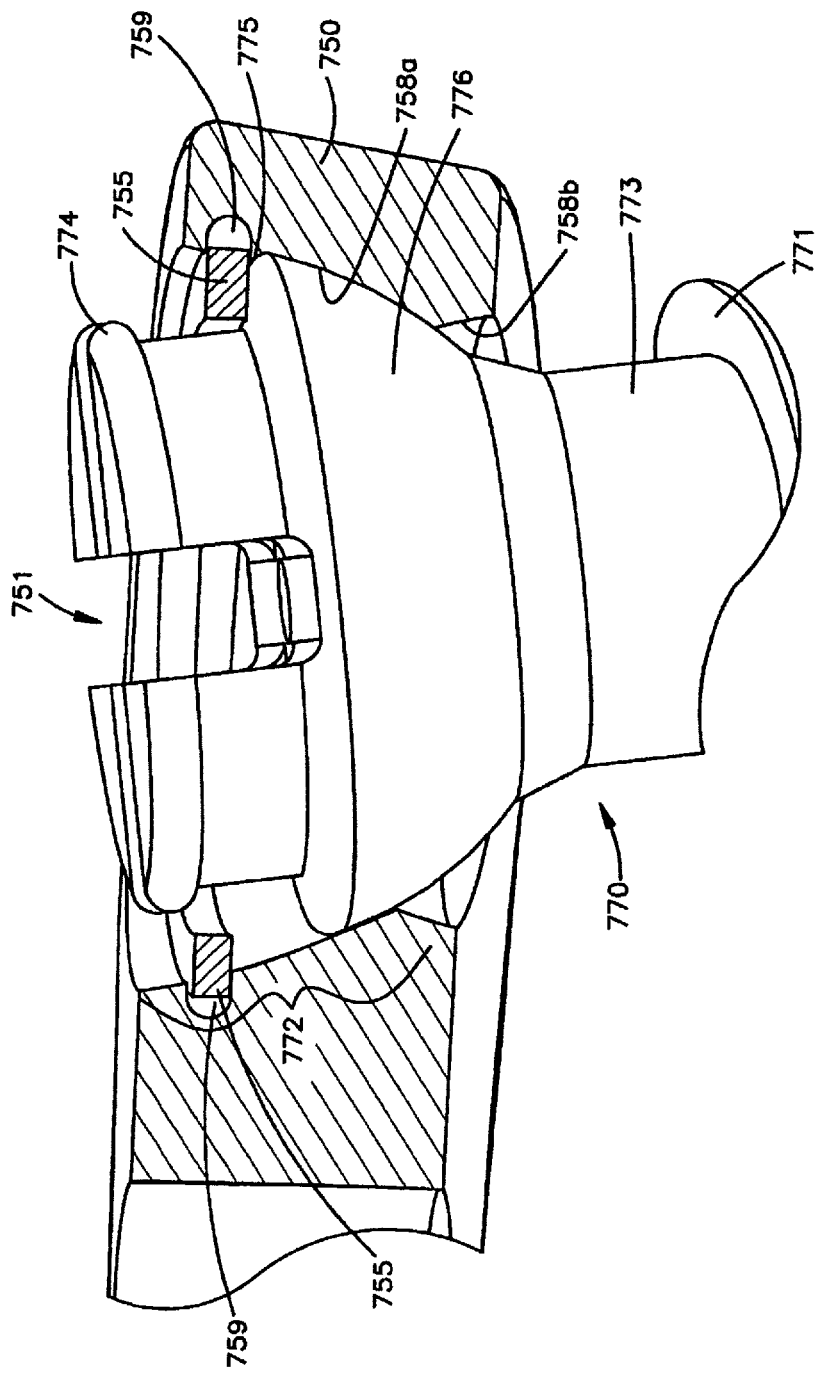
Figure 42B:
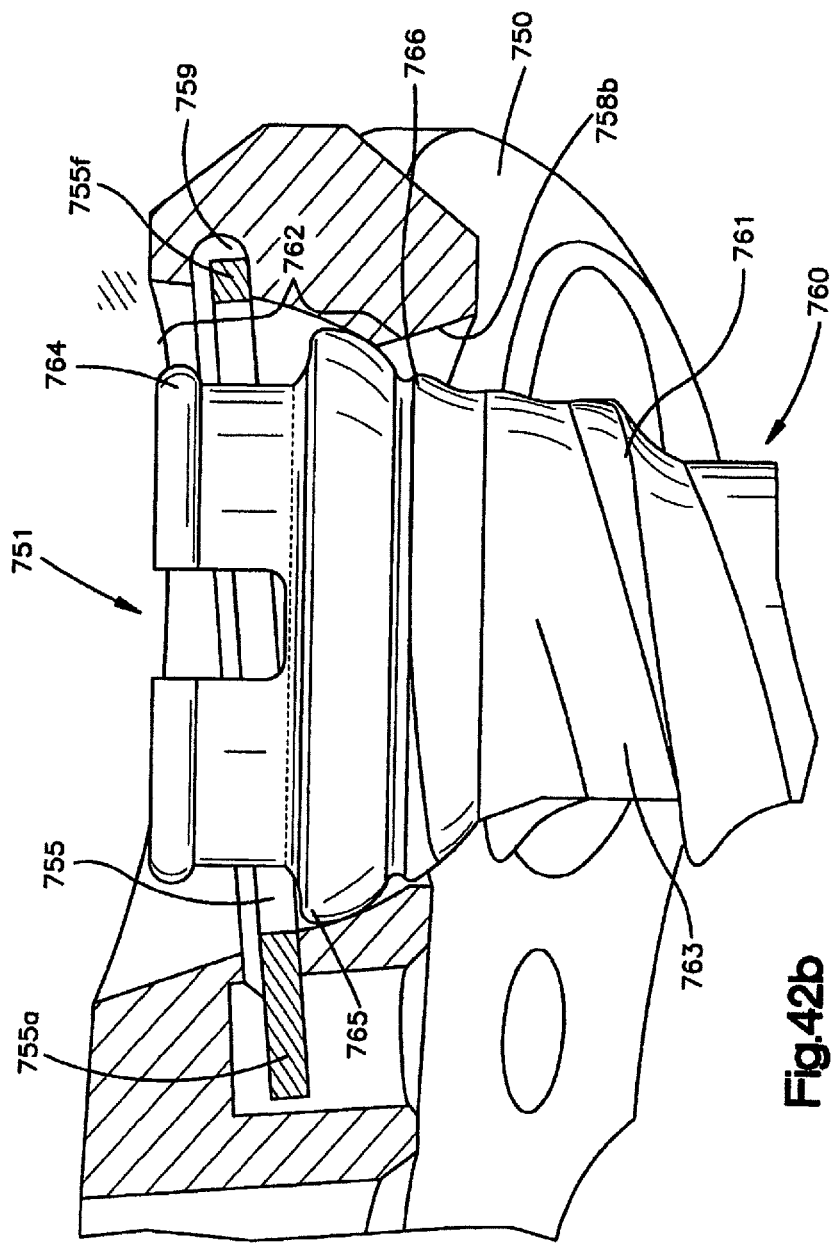

FIG. 37G shows a partial side view of area S of FIG. 37C;

FIG. 37H shows an alternate a top view of the fastener of FIG. 37A;

FIG. 37I shows an alternate partial top view of the fastener of FIG. 37A;

FIG. 38A shows a perspective view of an embodiment of a plate having gussets;

FIG. 38B shows a top view of the plate of FIG. 38A;

FIG. 38C shows a cross-sectional side view taken along line XXXVIIIC-XXXVIIIC of the plate of FIG. 38A;

FIG. 38D shows a cross-sectional side view taken along line XXXVIIID-XXXVIIID of the plate of FIG. 38A, with a fastener disposed in a hole in the plate;

FIG. 38E shows a perspective view of an embodiment of a fastener with slits;

FIG. 38F shows a cross-sectional side view of the fastener of FIG. 38E with a fastener head in an expanded state;

FIG. 38G shows a cross-sectional side view of the fastener of FIG. 38E with a fastener head in a contracted state as being inserted or removed from the plate;

FIG. 39A shows a perspective view of another embodiment of a fixation system;

FIG. 39B shows a top view of the plate of the fixation system shown in FIG. 39A;

FIG. 39C shows a side view of the plate of FIG. 39B;

FIG. 39D shows a cross-sectional view of the plate of FIG. 39C taken along the line X39-X39;

FIG. 40 shows a top view of an embodiment of a clip;

FIG. 41A shows a side view of an exemplary variable-angle screw;

FIG. 41B shows a side view of an exemplary fixed-angle screw;

FIG. 42A shows a partially-removed cross-sectional view of a variable-angle screw engaging a plate;

FIG. 42B shows a partially-removed cross-sectional view of a fixed-angle screw engaging a plate;

FIG. 43A shows a side view of an exemplary variable-angle drill guide for use with the system of FIG. 39A;

FIG. 43B shows a cross-sectional view of the barrel of the drill guide of FIG. 43A;

FIG. 43C shows an enlarged partial cross-sectional view of the tip portion of the drill guide of FIG. 43A;

FIG. 44A shows a side view of an exemplary fixed-angle drill guide for use with the system of FIG. 39A;

FIG. 44B shows a cross-sectional view of the barrel of the drill guide of FIG. 44A;

FIG. 44C shows an enlarged partial cross-sectional view of the tip portion of the drill guide of FIG. 44A; and FIG. 44D shows a partially-removed cross-sectional view of a fixed-angle drill guide engaging a plate.

DETAILED DESCRIPTION OF ILLUSTRATIVE EMBODIMENTS

Turning to FIGS. 1A-4G, a first embodiment of a fixation system is shown. The fixation system includes a plate 20 with two pairs of fixation holes 22, 24. Fixation holes 22 are oblong in shape so as to have a different length than width (i.e., the hole is non-circular), while fixation holes 24 are circular in shape. The fixation holes are preferably oblong in the direction along the longitudinal axis 28a of the bone plate 20. Although plate 20 is provided with two pairs of fixation holes 22, 24, more than two pairs may instead be provided, for example so that plate 20 may span a greater length and thus be fastened to multiple locations along the spine. Single holes alternatively may be provided as opposed to pairs.

A slot 26 is aligned along central longitudinal axis 28a for receiving a drill/screw guide and for graft visualization. Preferably, slot 26 does not receive any fasteners. In alternate embodiments, more than one slot may be provided, and the slot or slots may be disposed transverse to central longitudinal axis 28a. Preferably, slot 26 includes straight portions 26a and semicircular portions 26b.

Each of fixation holes 22, 24 extends between top and bottom surfaces 28, 30 and includes an undercut 32. In one embodiment, undercut 32 is disposed closer to top surface 28 than bottom surface 30 while in another embodiment, undercut 32 is disposed closer to bottom surface 30 than top surface 28. Undercut 32 also may be disposed intermediate top and bottom surfaces 28, 30, or transverse to the surfaces. Preferably, an undercut 32 extends completely around each of fixation holes 22, 24. A lower portion 34 of each fixation hole 22, 24 may be disposed between bottom surface 28 and undercut 32 and may taper toward a central axis 36 of the respective fixation hole as shown for example in FIG. 1D. Preferably, lower portion 34 has a first maximum inner dimension L1 and the undercut has a second maximum inner dimension L2, wherein the first maximum inner dimension L1 is less than the second maximum inner dimension L2.

Figure 2A:
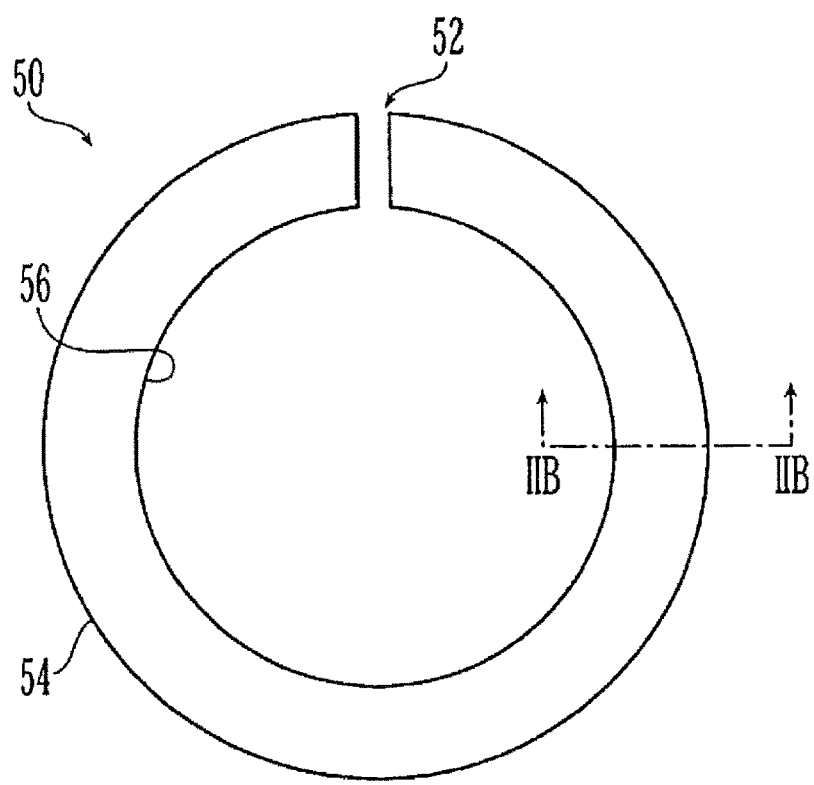
FIG. 2A shows a captive clip for use with the plate of FIG. 1A.
Figure 2B:
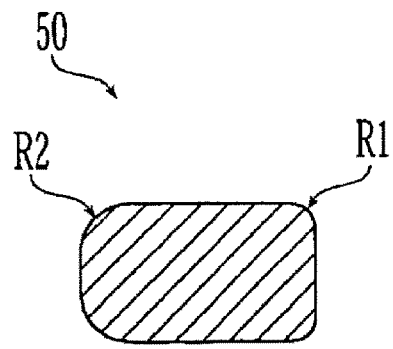
FIG. 2B shows a cross-sectional view taken along line IIB-IIB of the captive clip of FIG. 2A.

Turning to FIGS. 2A and 2B, a generally circular captive clip 50 is shown with a slit 52 that permits elastic expansion/compression of clip 50 as will be explained shortly, as well as an outer edge 54 and an inner edge 56. Clip 50 includes a generally rectangular cross-section, and in one embodiment, is provided with a radius R1 adjoining outer edge 54 of about 0.1 mm and a second radius R2 adjoining inner edge 56 of about 0.2 mm.

Figure 1A:
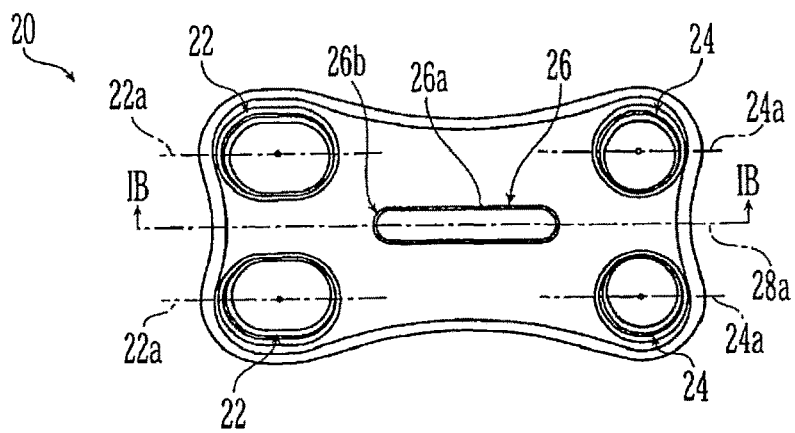
FIG. 1A shows a top view of a plate for use with a first embodiment of a fixation system.
Figure 1B:
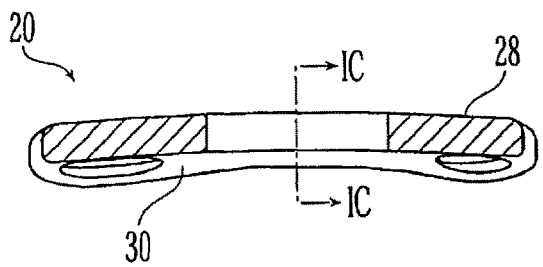
FIG. 1B shows a partial cross-sectional view taken along line IB-IB of the plate of FIG. 1A.
Figure 1C:
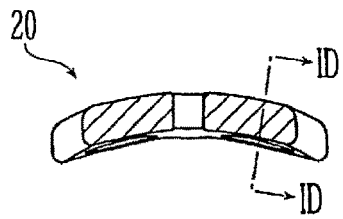
FIG. 1C shows a partial cross-sectional view taken along line IC-IC of the plate of FIG. 1B.
Figure 1D:
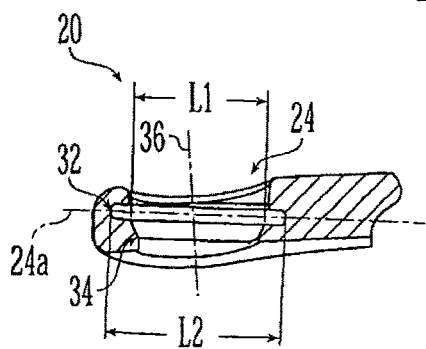
FIG. 1D shows a partial cross-sectional view taken along line ID-ID of the plate of FIG. 1C.
Figure 1E:
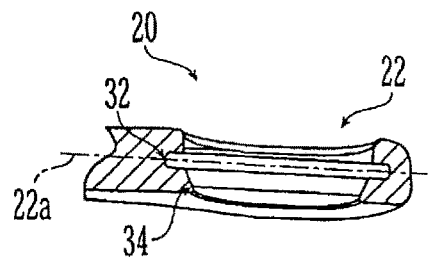
FIG. 1E shows another partial cross-sectional view taken along line ID-ID of the plate of FIG. 1C.
Figure 3:
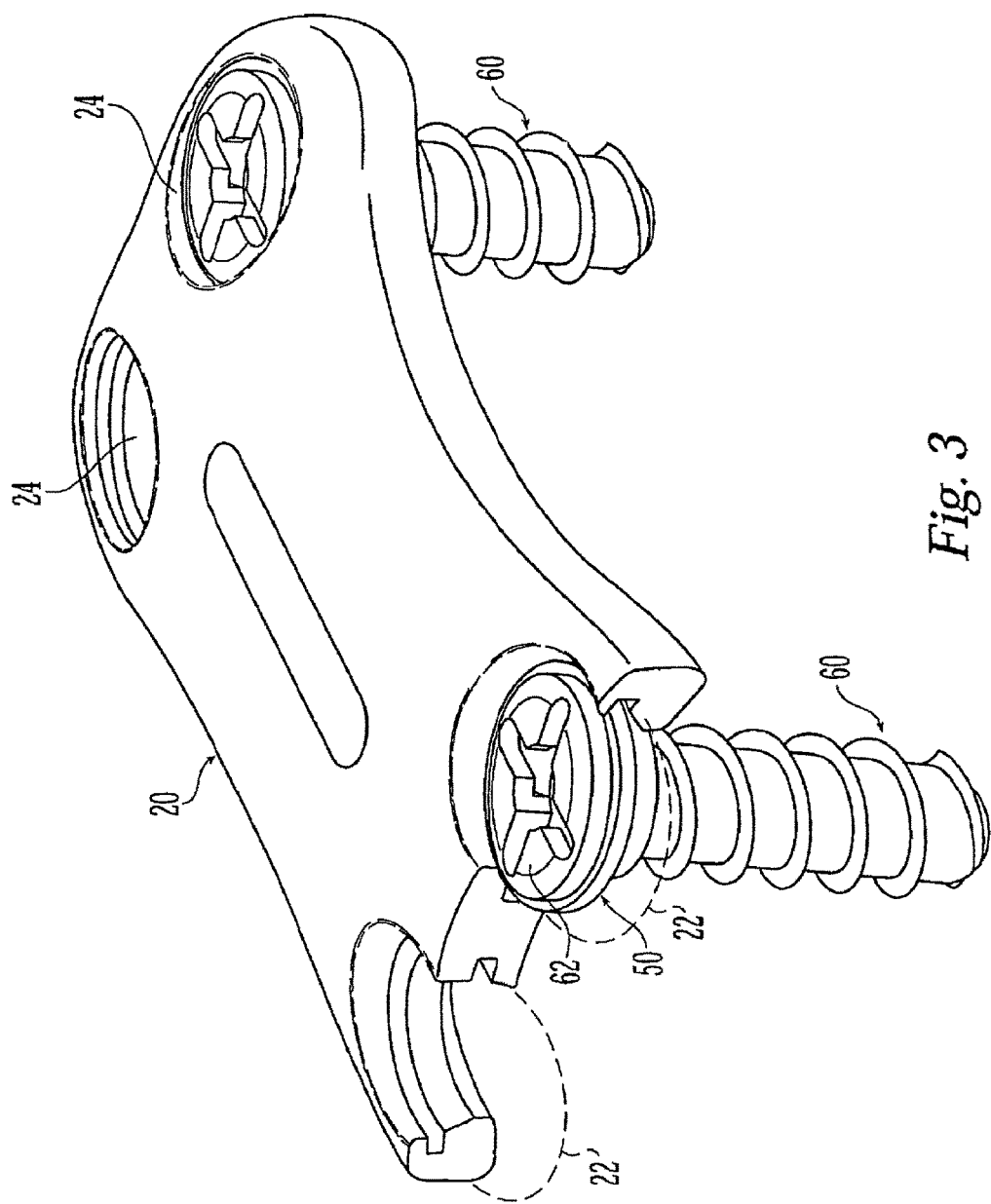
FIG. 3 shows a partial cross-sectional perspective view of the plate of FIG. 1A with fasteners installed therewith.
Figure 4A:
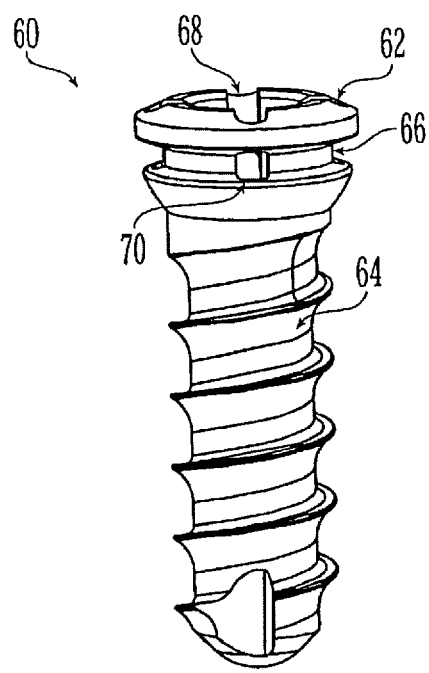
FIG. 4A shows a perspective view of an embodiment of a fastener.
Figure 4B:
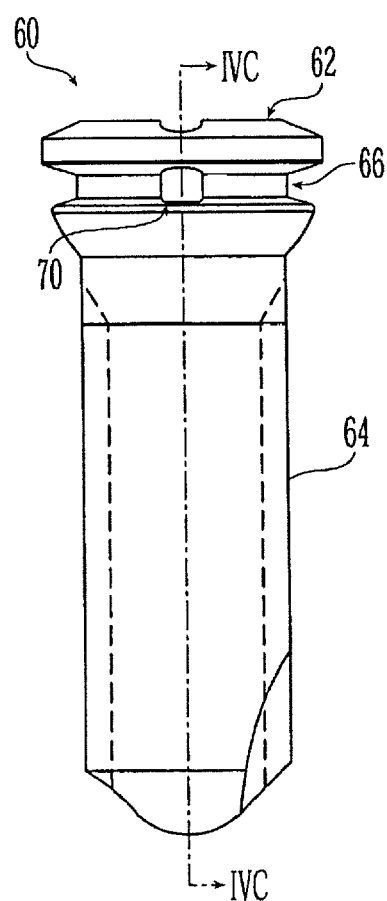
FIG. 4B shows a side view of the fastener of FIG. 4A.
Figure 4C:
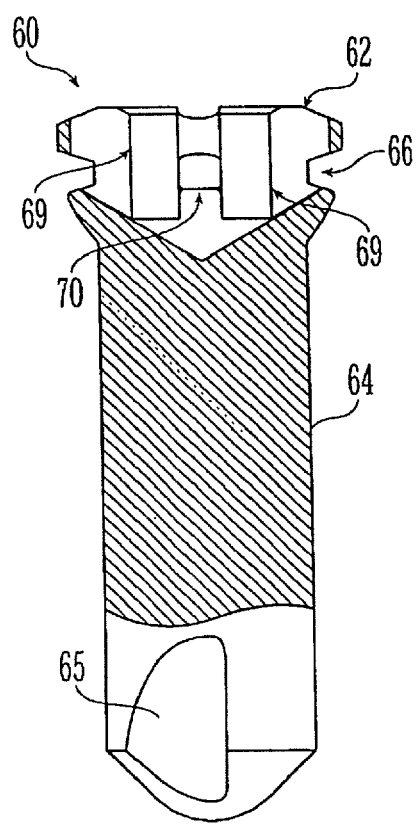
FIG. 4C shows a partial cross-sectional side view taken along line IVC-IVC of the fastener of FIG. 4B.
Figure 5A:
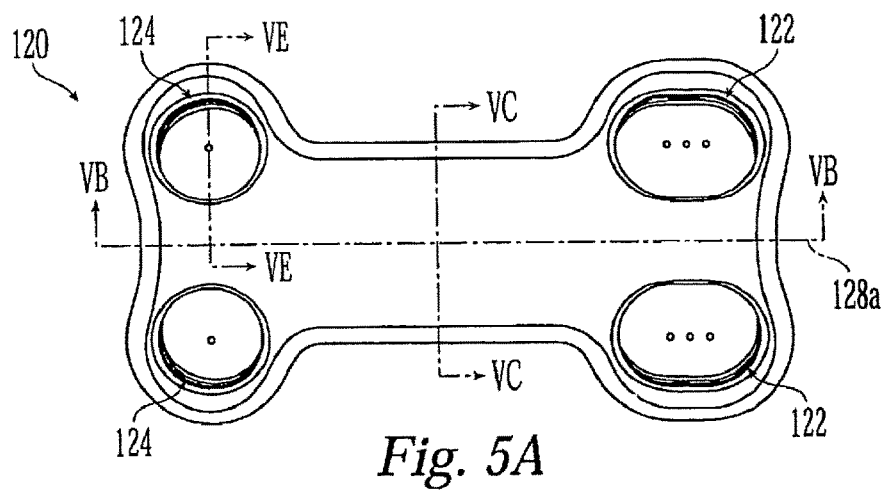
FIG. 5A shows a top view of a plate for use with a different embodiment of a fixation system.
Figure 5B:
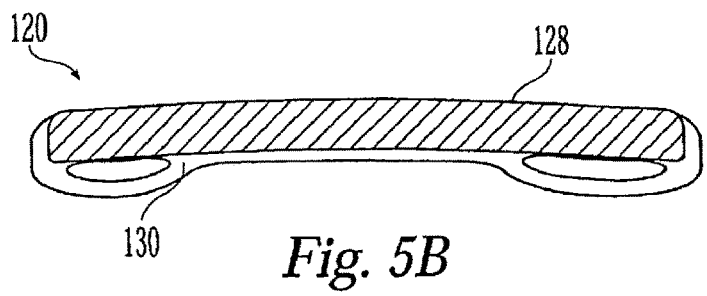
FIG. 5B shows a partial cross-sectional view taken along line VB-VB of the plate of FIG. 5A.
Figure 5C:
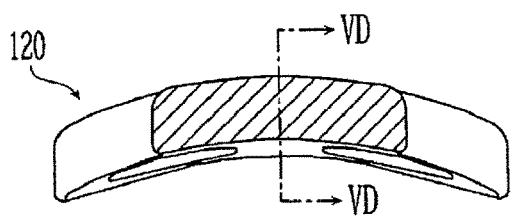
FIG. 5C shows a partial cross-sectional view taken along line VC-VC of the plate of FIG. 5B.
Figures 5D, 5E:
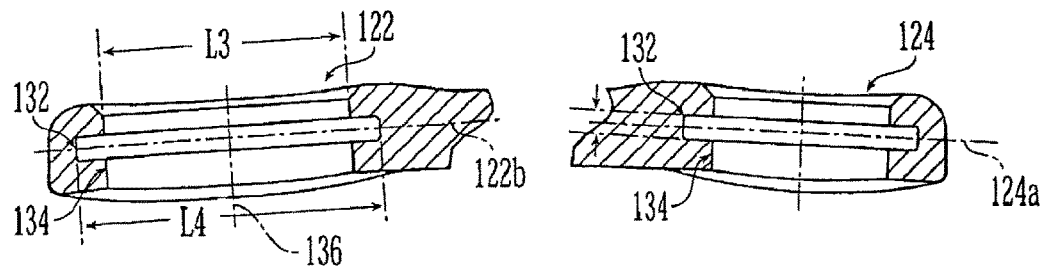
FIG. 5D shows a partial cross-sectional view taken along line VD-VD of the plate of FIG. 5C.
FIG. 5E shows another partial cross-sectional view taken along line VE-VE of the plate of FIG. 5A.

Referring to FIG. 3, plate 20 is shown with a fastener 60 in each of fixation holes 22, 24. A captive clip 50 is provided for each fastener 60 around head 62. Preferably, a clip 50 is pre-installed in each fixation hole 22, 24, and snap-fits around a head 62 of a fastener 60 such that post-operative back-out of a fastener 60 from a hole 22, 24 is resisted. Preferably, a captive clip 50 disposed in an undercut 32 of an elongated, oblong hole 22 is permitted to travel (slide) along a longitudinal axis 22a of the hole, as shown in FIGS. 1A and 1E. Thus, a fastener 60 on a captive clip 50 and disposed in an oblong hole 22 can slide across the length of hole 22. However, a captive clip 50 disposed in an undercut 32 of a circular hole 24 is not permitted to travel (slide) along a longitudinal axis 24a of hole 24, a shown in FIGS. 1A and 1D.

As will be described in detail herein, various embodiments of fasteners are contemplated. In particular, two main types of fasteners for "variable angle" and "fixed angle" applications are provided.

"Variable angle" refers to fasteners and/or plates for which: (1) the trajectory of insertion of the fastener into bone (through a fixation hole in the plate) may be selected by the surgeon (although only a limited range of motion may be permitted); and/or (2) the trajectory of the fastener with respect to the plate is allowed to change following insertion into bone, for example to toggle to accommodate any translational and/or rotational settling that occur post-operatively between the plate and the fastener that has been rigidly placed into a vertebral body (although only a limited range of motion may be permitted).

"Fixed angle" refers to fasteners and/or plates for which: (1) the trajectory of insertion of the fastener into bone (through a fixation hole in the plate) is pre-selected and thus fixed; and/or (2) the trajectory of the fastener with respect to the plate is not allowed to change following insertion into bone.

Each of the two main types of fasteners may be provided with features for use preferably with either cancellous or cortical bone. Moreover, each of the two main types of fasteners may be provided preferably with either self-tapping or self-drilling features. Finally, the diameters of the fasteners may be varied as well as the lengths. In selecting a fastener for a given application, therefore, a surgeon must decide which type of fastener and which combination of features are appropriate. A the minimum, the surgeon must select among eight categories of fasteners: (1) variable-angle, cancellous, self-tapping, (2) variable-angle, cancellous, self-drilling, (3) variable-angle, cortical, self-tapping, (4) variable-angle, cortical, self-drilling, (5) fixed-angle, cancellous, self-tapping, (6) fixed-angle, cancellous, self-drilling, (7) fixed-angle, cortical, self-tapping, and (8) fixed-angle, cortical, self-drilling.

As shown in FIGS. 4A-4G, an exemplar fastener 60 includes a head 62 with a self-tapping, threaded shaft 64 with a flute 65 provided proximate the bottom of the threading. In an alternate embodiment, as described above, a self-drilling, threaded shaft 64 instead may be provided. Head 62 includes a perimetral groove 66 extending around at least a portion thereof, and an instrument receiving portion 68 that at least partially intersects groove 66 at one or more openings 70. Instrument receiving portion 68 preferably includes an internal, unthreaded, cylindrical, annular wall 69, although in an alternate embodiment wall 69 may be threaded. In the exemplar embodiment of FIG. 4E, instrument receiving portion 68 is cross-shaped and thus intersects groove 66 at four openings 70. A pair of slots 70a, 70b (similar to the look of a Phillips-head screw) form instrument receiving portion 68. However, in alternate embodiments, only one opening 70, two openings 70, or any number of openings 70 may be provided. Fastener 60 preferably is used with a plate 20 such that fastener 62 may toggle in the fixation holes. In addition, fastener 60 preferably is used for fixation to cancellous bone. However, threading appropriate for cortical bone instead may be provided.

In one preferred exemplary embodiment, perimetral groove 66 includes an upper surface 66a and a lower surface 66b disposed at an angle δ of between about 10° and about 70° with respect to each other. More preferably, upper surface 66a and lower surface 66b are disposed at an angle δ of between about 30° and about 50° with respect to each other, and most preferably, they are an angle δ of about 40° with respect to each other. The angulation of surfaces 66a, 66b with respect to each other permits toggling of fastener 60 when coupled to a captive clip 50.

Head 62 preferably is partially spherical and includes a bottom section 68 extending to the top end 70 of shaft 64, with bottom section 68 tapering inward toward longitudinal axis 72 from perimetral groove 66 to top end 70. Advantageously, such tapering permits angulation of fastener 60 when disposed in a fixation hole 22, 24.

In use, a fastener 60 is received in a captive clip 50. The shaft 64 is initially screwed into bone until the partial-spherical head 62 of fastener 60 reaches captive clip 50. Upon further insertion of fastener 60 into captive clip 50, the partial-spherical head 62, particularly bottom section 68, bears against the inside edge 56 of captive clip 50 and expands captive clip 50. Once fastener 60 is inserted far enough, captive clip 50 contracts so that it "snaps" into perimetral groove 66 in head 62, thereby preventing fastener 60 from backing out of plate 20, as previously described.

In addition, captive clip 50 subsequently may be elastically expanded to permit removal of fastener 60. When a screwdriver tip is inserted in the slots 70a, 70b of instrument receiving portion 68, the screwdriver tip protrudes into the perimetral groove 66 through openings 70. Inserting the screwdriver tip thus elastically expands captive clip 50 to allow fastener 60 to be unscrewed from bone without interference from captive clip 50.

A second embodiment of a fixation system is shown in FIGS. 5A-8G. The fixation system includes a plate 120 with two pairs of fixation holes 122, 124. Fixation holes 122 are oblong in shape so as to have a different length than width (i.e., the hole is non-circular), while fixation holes 124 are circular in shape. Although plate 120 is provided with two pairs of fixation holes 122, 124, more than two pairs may instead be provided, for example so that plate 120 may span a greater length and thus be fastened to multiple locations along the spine.

Plate 120 is not provided with a slot for receiving a drill/screw guide or for graft visualization. However, in alternate embodiments, one or more slots may be provided, and the slot or slots may be disposed transverse to central longitudinal axis 128a.

Each of fixation holes 122, 124 extends between top and bottom surfaces 128, 130 and includes an undercut 132. In one embodiment, undercut 132 is disposed closer to top surface 128 than bottom surface 130 while in another embodiment, undercut 132 is disposed closer to bottom surface 130 than top surface 128. Undercut 132 also may be disposed intermediate top and bottom surfaces 128, 130, or transverse to the surfaces. Preferably, an undercut 132 extends completely around each of fixation holes 122, 124. A lower portion 134 of each fixation hole 122, 124 may be disposed between bottom surface 128 and undercut 132. Lower portion 134 optionally may taper toward a central axis 136 of the respective fixation hole as shown for example in FIG. 5D. Preferably, lower portion 134 has a first maximum inner dimension L3 and the undercut has a second maximum inner dimension L4, wherein the first maximum inner dimension L3 is less than the second maximum inner dimension L4.

Figure 6A:
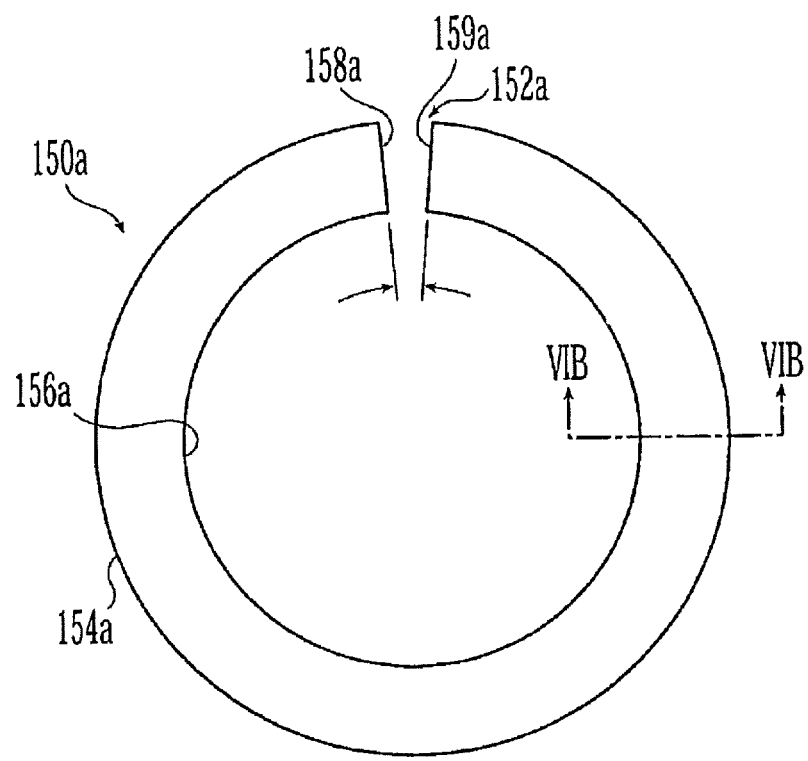
FIG. 6A shows a circular captive clip for use with the plate of FIG. 5A.
Figure 6B:
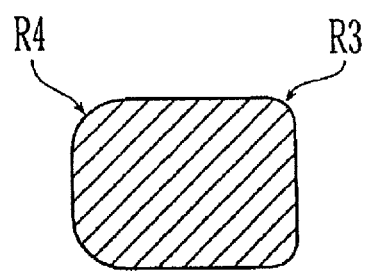
FIG. 6B shows a cross-sectional view taken along line VIB-VIB of the circular captive clip of FIG. 6A.
Figure 7A:
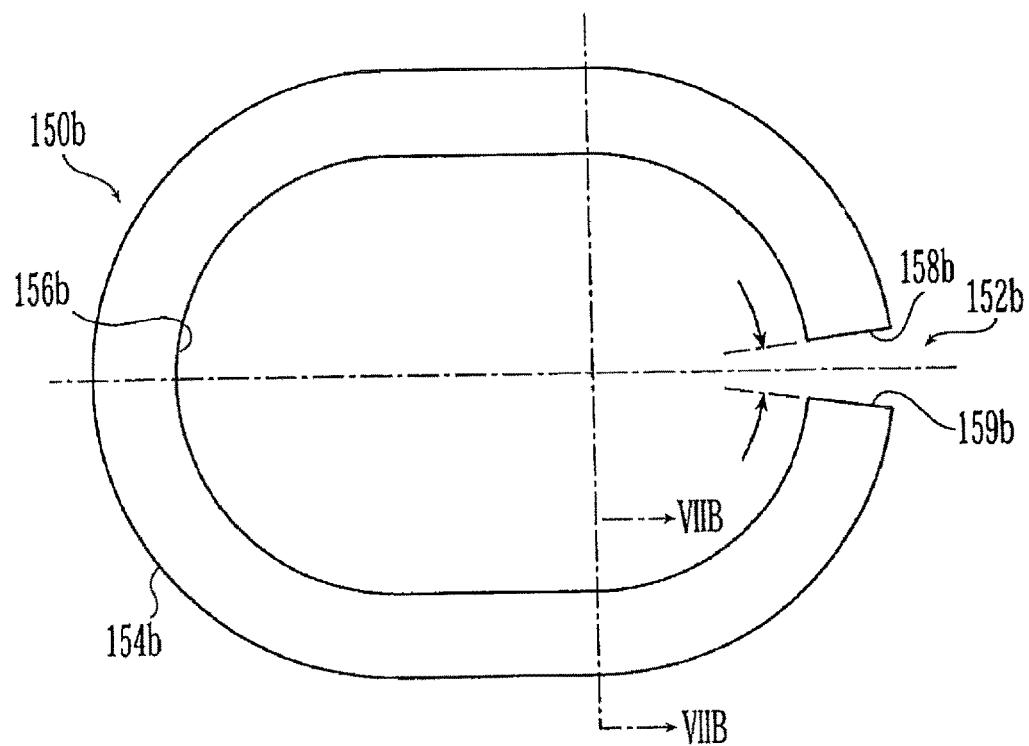
FIG. 7A shows an oblong captive clip for use with the plate of FIG. 5A.
Figure 7B:
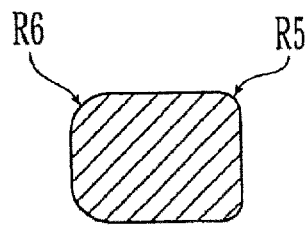
FIG. 7B shows a cross-sectional view taken along line VIIB-VIIB of the circular captive clip of FIG. 7A.
Figure 8A:
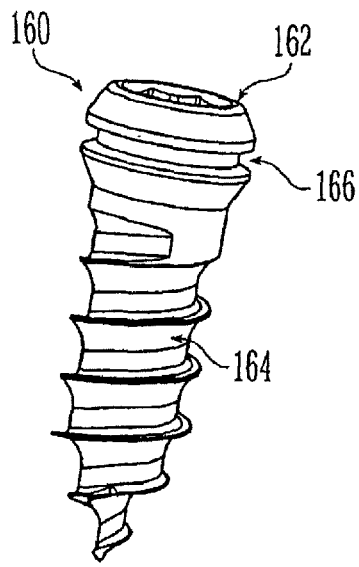
FIG. 8A shows a perspective view of an embodiment of a self-drilling fastener.
Figure 8B:
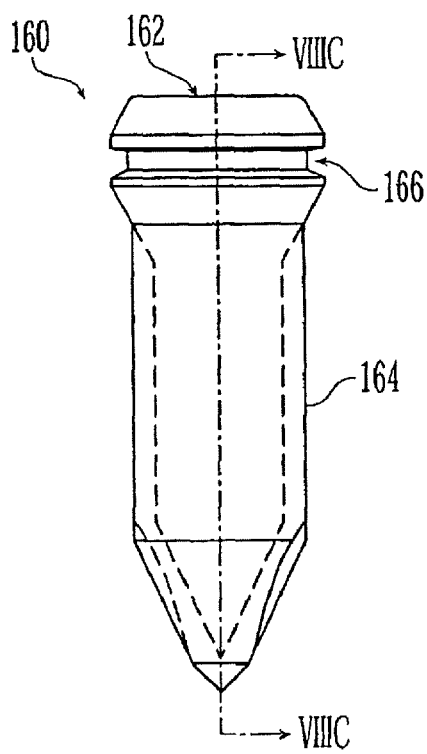
FIG. 8B shows a side view of the fastener of FIG. 8A.
Figure 8C:
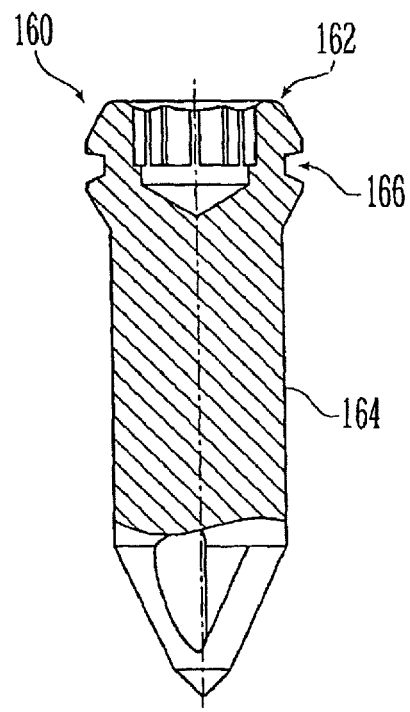
FIG. 8C shows a partial cross-sectional side view taken along line VIIIC-VIIIC of the fastener of FIG. 8B.
Figure 8D:
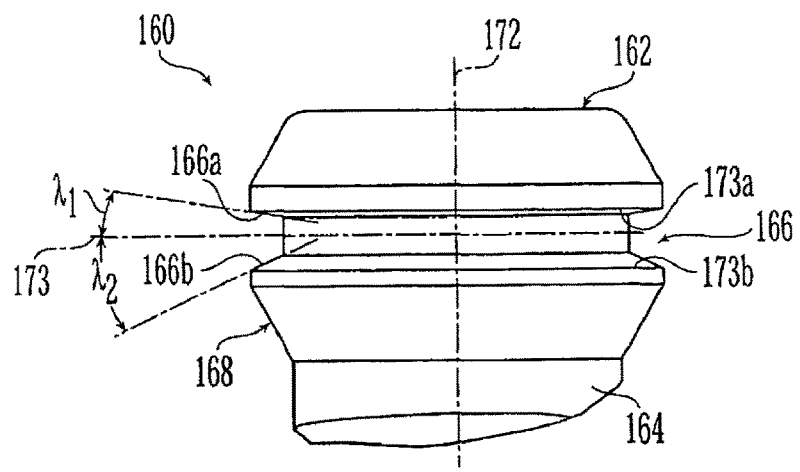
FIG. 8D shows a partial side view of the head of the fastener of FIG. 8A.
Figure 8E:
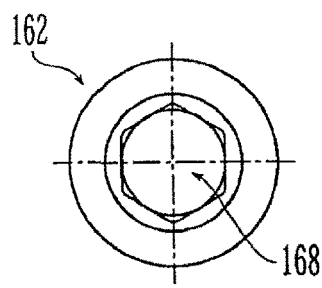
FIG. 8E shows a top view of the fastener of FIG. 8A.
Figure 8F:
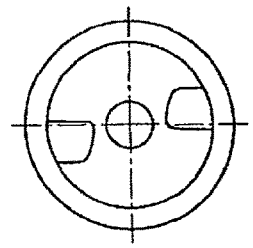
FIG. 8F shows a bottom view of the fastener of FIG. 8A.
Figure 8G:
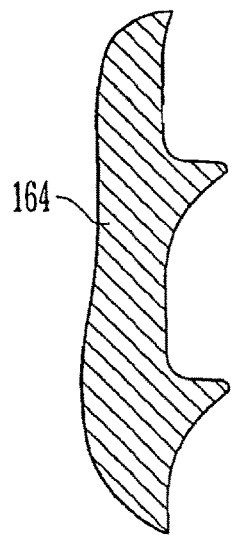
FIG. 8G shows a partial cross-sectional side view of the shaft and threads of the fastener of FIG. 8A.
Figure 9E:
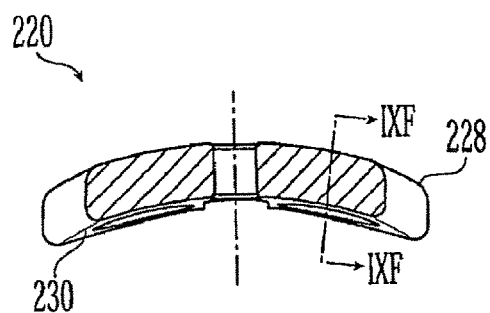
FIG. 9E shows a partial cross-sectional view taken along line IXE-IXE of the plate of FIG. 9B.
Figure 9F:
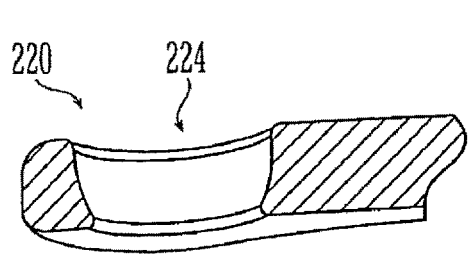
FIG. 9F shows a partial cross-sectional view taken along line IXF-IXF of the plate of FIG. 9E.
Figure 9G:
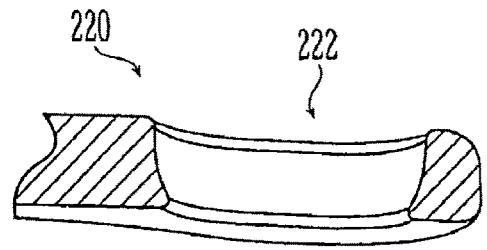
FIG. 9G shows another partial cross-sectional view taken along line IXF-IXF of the plate of FIG. 9E.

Plate 120 may be provided with two types of captive clips. First, a circular captive clip 150a is shown in FIGS. 6A and 6B with a slit 152a that permits elastic expansion/compression of clip 150a as previously explained, as well as an outer edge 154a and an inner edge 156a. Clip 150a includes a generally rectangular cross-section, and in one embodiment, is provided with a radius R3 on outer edge 154a of about 0.1 mm and a second radius R4 on inner edge 156a of about 0.2 mm. In a relaxed state, ends 158a, 159a forming slit 152a of clip 150a preferably are angled at between about 5° and about 15° with respect to each other, and more preferably at about 10°. Clip 150a is sized to be received in fixation hole 124. Second, an oblong captive clip 150b is shown in FIGS. 7A and 7B with a slit 152b that permits elastic expansion/compression of clip 150b as previously explained, as well as an outer edge 154b and an inner edge 156b. Clip 150b includes a generally rectangular cross-section, and in one embodiment, is provided with a radius R5 at outer edge 154b of about 0.1 mm and a second radius R6 at inner edge 156b of about 0.2 mm. Clip 150b is sized to be received in a fixation hole 122. In a relaxed state, ends 158b, 159b forming slit 152b of clip 150b preferably are angled at between about 5° and about 15° with respect to each other, and more preferably at about 10°.

In an exemplary preferred embodiment, a captive clip 150a or 150b is provided for each fastener 160 around head 162, based on whether the fastener 160 is disposed in an oblong fixation hole 122 or a circular fixation hole 124.

Preferably, a clip 150 is pre-installed in each fixation hole 122, 124, and snap-fits around at least part of a head 162 of a fastener 160 during installation of the fastener such that post-operative back-out of a fastener 160 from a hole 122, 124 is resisted. Preferably, when a captive clip 150b is disposed in undercut 132 of elongated, oblong hole 122, captive clip 150b serves as a rail upon which a fastener 160 is permitted to travel (slide) along a longitudinal axis 122b of the hole. Thus, a fastener 160 on a captive clip 150b and disposed in an oblong hole 122 can slide across the length of the hole. However, neither captive clip 150a disposed in an undercut 132 of a circular hole 124, nor a fastener captured by the captive clip 150a, is permitted to travel (slide) along a longitudinal axis 124a of the hole.

Turning to FIGS. 8A-8G, an exemplar fastener 160 according to the present invention includes a head 162 with a self-drilling, threaded shaft 164. In an alternate embodiment, a self-tapping, threaded shaft 164 instead may be provided. Head 152 includes a perimetral groove 166 extending around at least a portion thereof, and an instrument receiving portion 168. Although instrument receiving portion 168 is not shown to at least partially intersect groove 166 at one or more openings, provision for such may be made as described previously. In the exemplar embodiment of FIG. 8E, instrument receiving portion 168 is hexagonal-shaped. However, in alternate embodiments, other shapes may be provided. Fastener 160 preferably is used with a plate 120 such that fastener 160 may toggle in the fixation holes. In addition, fastener 160 preferably is used for fixation to cancellous bone.

In one preferred exemplary embodiment, perimetral groove 166 includes an upper surface 166a and a lower surface 166b that are disposed at between about 5° and about 50° with respect to each other. Preferably, upper surface 166a is disposed at an angle $\lambda_1$ of between about 5° and about 15° with respect to a line 173 disposed approximately intermediate upper inside edge 173 and lower inside edge 173b and perpendicular to longitudinal axis 172. Most preferably, angle $\lambda_1$ is about 10°. In addition, lower surface 166b preferably is disposed at an angle $\lambda_2$ of between about 15° and about 35° with respect to line 173. Most preferably, angle $\lambda_2$ is about 25°. Thus, most preferably, angles $\lambda_1$, $\lambda_2$ total about 35°. The angulation of surfaces 166a, 166b with respect to each other permits toggling of fastener 160 when coupled to a captive clip 150a, 150b.

Head 162 preferably is partially spherical and includes a bottom section 168 extending to the top 170 of shaft 164, with bottom section 168 tapering inward toward longitudinal axis 172 from perimetral groove 166 to top 170. Advantageously, such tapering permits angulation of fastener 160 when disposed in a fixation hole 122, 124.

In use, a fastener 160 is received in a captive clip 150a or 150b. The shaft 164 is initially screwed into bone until the partial-spherical head 162 of fastener 160 reaches captive clip 150a or 150b. Upon further insertion of fastener 160 into captive clip 150, the partial-spherical head 162, particularly bottom section 168, bears against the inside edge 156a, 156b of captive clip 150a, 150b, respectively, and expands the clip. Once fastener 160 is inserted far enough, captive clip 150a or 150b contracts so that it "snaps" into perimetral groove 166 in head 162, thereby preventing fastener 160 from backing out of plate 120, as previously described.

A third embodiment of a fixation system is shown in FIGS. 9A-12. The fixation system includes a plate 220 with two pairs of fixation holes 222, 224. Fixation holes 222 are oblong in shape, while fixation holes 224 are circular in shape. Although plate 220 is provided with two pairs of fixation holes 222, 224, more than two pairs may instead be provided, for example so that plate 220 may span a greater length and thus be fastened to multiple locations along the spine.

A slot 226 is aligned along central longitudinal axis 228a for receiving a drill/screw guide and for graft visualization. Preferably, slot 226 does not receive any fasteners. In alternate embodiments, more than one slot may be provided, and the slot or slots may be disposed transverse to central longitudinal axis 228a. Preferably, slot 226 includes straight portions 226a and semicircular portions 226b.

Each of fixation holes 222, 224 extends between top and bottom surfaces 228, 230. As shown in particular in FIGS. 9C and 9D, each pair of the fixation holes is partially intersected by a common slot 232.

Figure 10A:
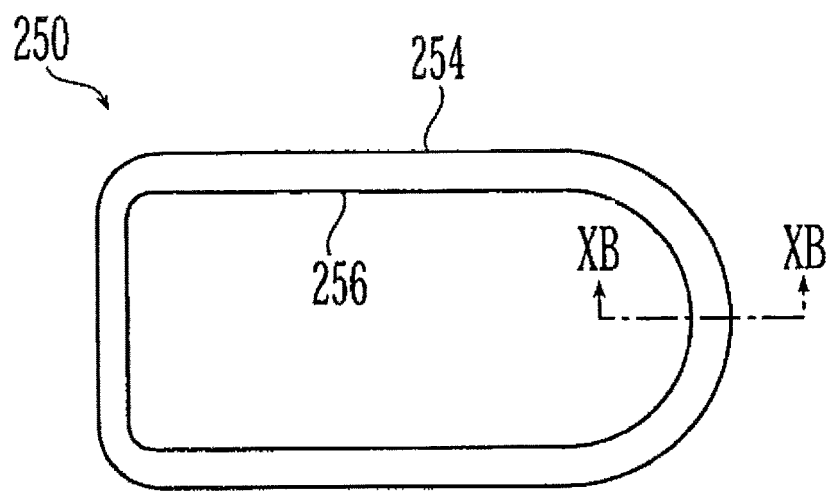
FIG. 10A shows a captive clip for use with the plate of FIG. 9A.
Figure 10B:
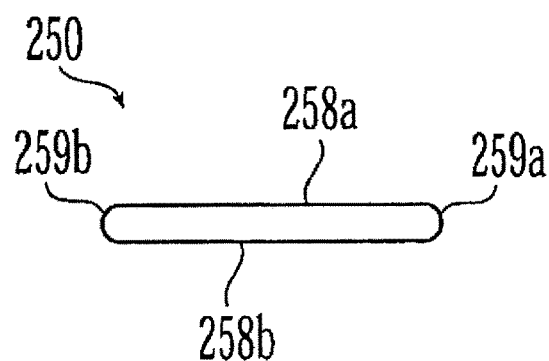
FIG. 10B shows a cross-sectional view taken along line XB-XB of the captive clip of FIG. 10A.

Turning to FIGS. 10A and 10B, an unslitted captive clip 250 is shown. Preferably, captive clip 250 is elastically flexible to permit expansion and contraction, although such flexibility is not necessary. Clip 250 has an outer edge 254 and an inner edge 256. Clip 250 also has a generally rectangular cross-section, and in one embodiment, has flat upper and lower surfaces 258a, 258b, as well as rounded sides 259a, 259b.

Figure 11:
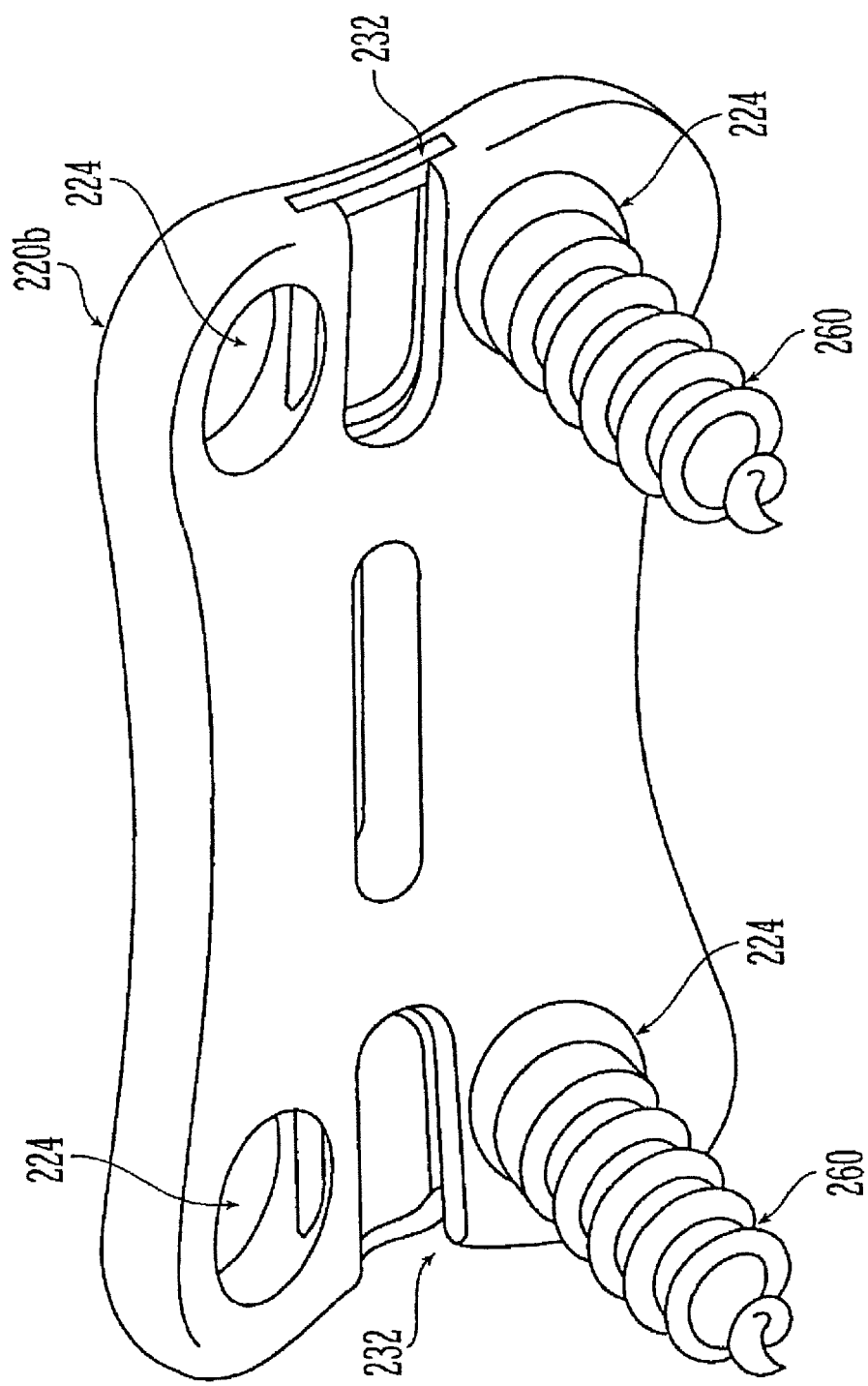
FIG. 11 shows a perspective view of another plate with fasteners installed therewith along with the captive clip of FIG. 10A.

In another embodiment of a plate 220b, shown in FIG. 11, two pairs of circular fixation holes 224 are provided. As explained with respect to plate 220, each pair of fixation holes 224 is partially intersected by a common slot 232. A captive clip 250 is inserted into each slot 232, and is sized such that it protrudes into each fixation hole 224. Preferably, a clip 250 is pre-installed in each slot 232. Once a fastener, such as one of the fasteners previously described with a perimetral groove in its head, is inserted far enough in the fixation hole, captive clip 250 bears against the perimetral groove, thereby locking the fastener in place and preventing the fastener from backing out of plate 220b. In order to permit removal of a fastener, a captive clip 250 may be removed from either the cephalad or caudal side of plate 220b where the fastener is located, thereby unlocking that fastener from plate 220b. Plate 220b is similar to plate 220 as shown in FIGS. 9A-9G, with a clip 250 assembled therewith.

Figure 12:
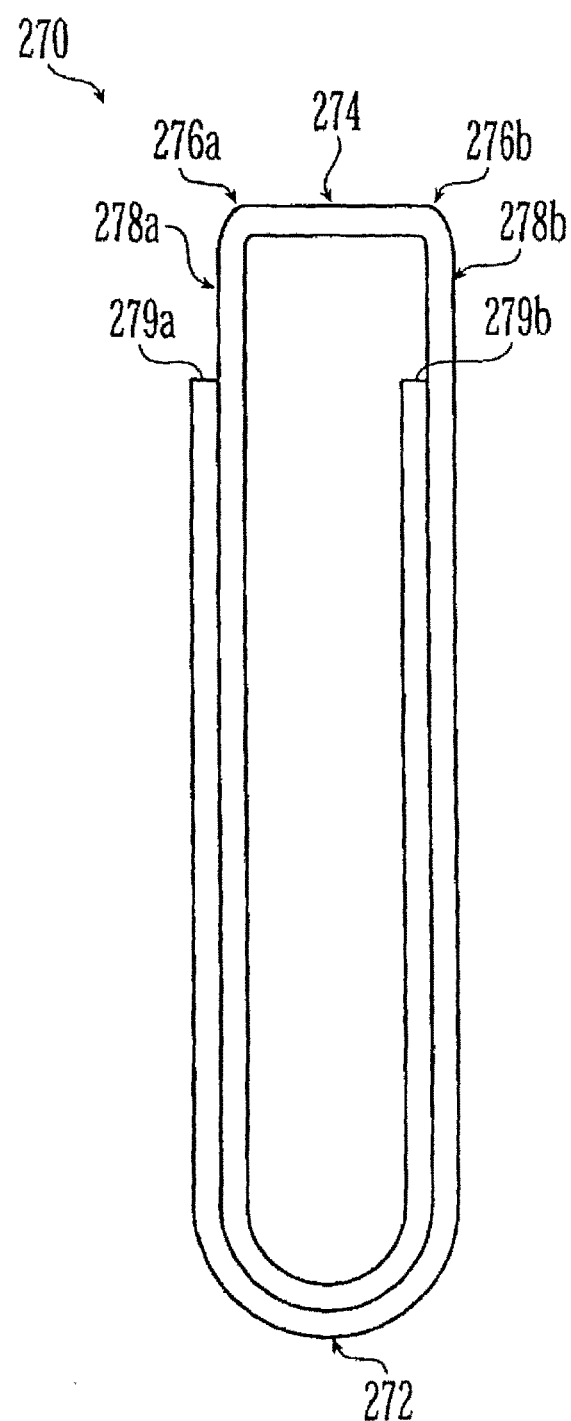
FIG. 12 shows an alternate captive clip for use with the plate of FIG. 9A or 11.
Figure 13:
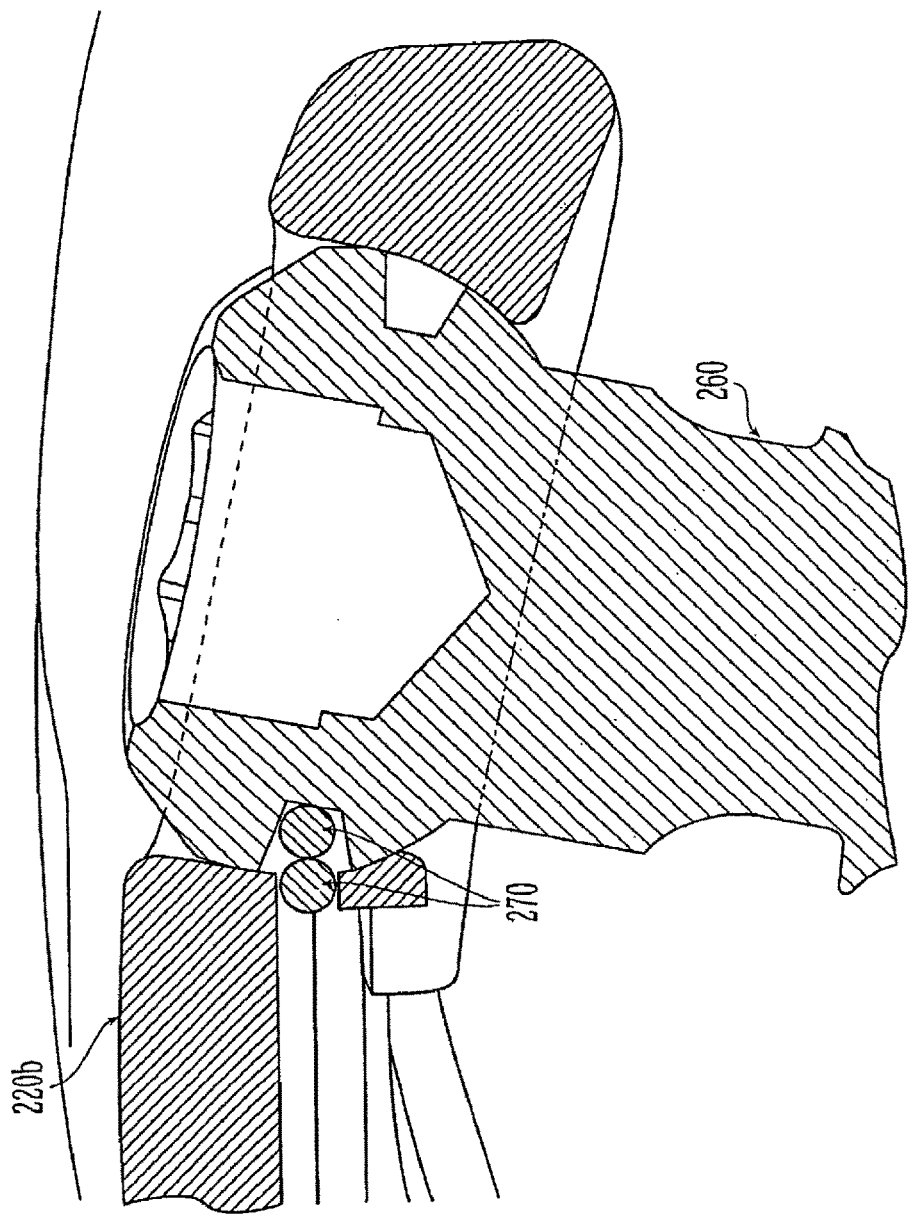
FIG. 13 shows a partial cross-sectional side view of the captive clip of FIG. 12 installed in the plate of FIG. 11.

An alternate embodiment of a clip 270 is shown in FIGS. 12-13. Clip 270 is generally shaped like a paper clip, and thus may confer spring-like behavior. As with the embodiment of plate 220b, clip 270 may be inserted in, and/or removed from, a slot 232 from either the cephalad or caudal side of plate 220b. Preferably, a first end 272 of clip 270 is arcuate, while a second end 274 is straight. The corners 276a, 276b of end 274 may be rounded, beveled, or provide a sharp transition from side edges 278a, 278b such as a right-angle transition between side edges 278a, 278b and end 274. Second end 274 is straight for stability, and preferably is disposed toward the outer edge of the plate. In some embodiments, one or more edge surfaces may be straight to allow for a flush resting surface with a greater surface area for abutting a surface of a plate in which clip 270 is installed. Two free ends 279a, 279b may be provided.

Figure 14:
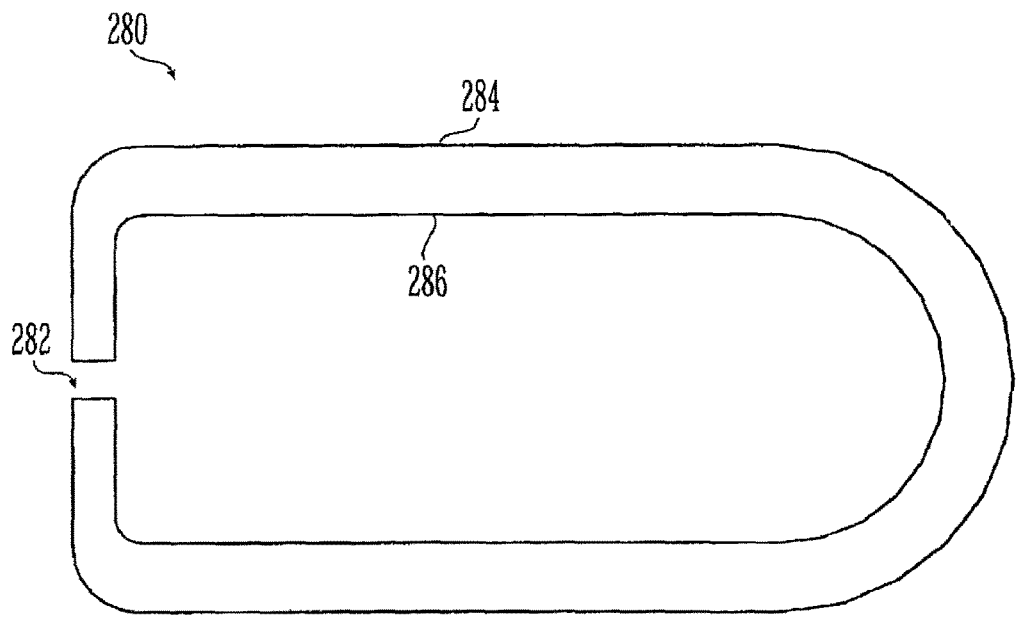
FIG. 14 shows another alternate captive clip.
Figure 15:
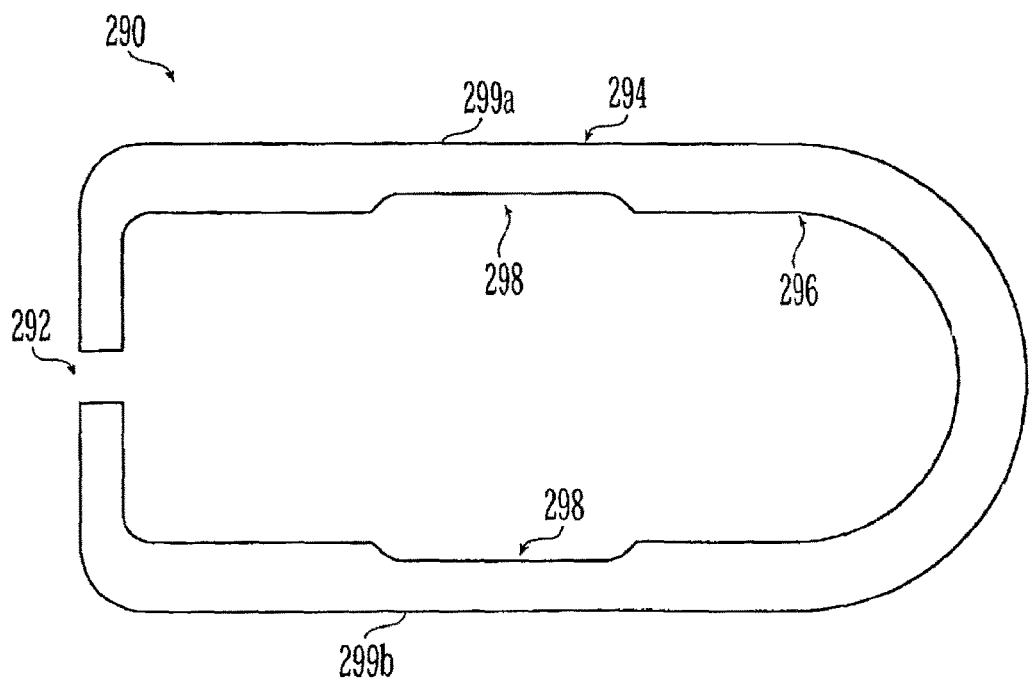
FIG. 15 shows yet another alternate captive clip.

Additional alternate embodiments of captive clips are shown in FIGS. 14 and 15. A clip 280, shown in FIG. 14, includes a slit 282 that permits elastic expansion/compression of clip 280 as previously explained. Clip 280 has an outer edge 284 and an inner edge 286. Clip 290, as shown in FIG. 15, includes a slit 292 that permits elastic expansion/compression, an outer edge 294, an inner edge 296, and further includes opposing recesses 298 the potential use of which will be explained below. Captive clip 290 further includes a pair of generally parallel sides 299a, 299b.

Figure 16A:
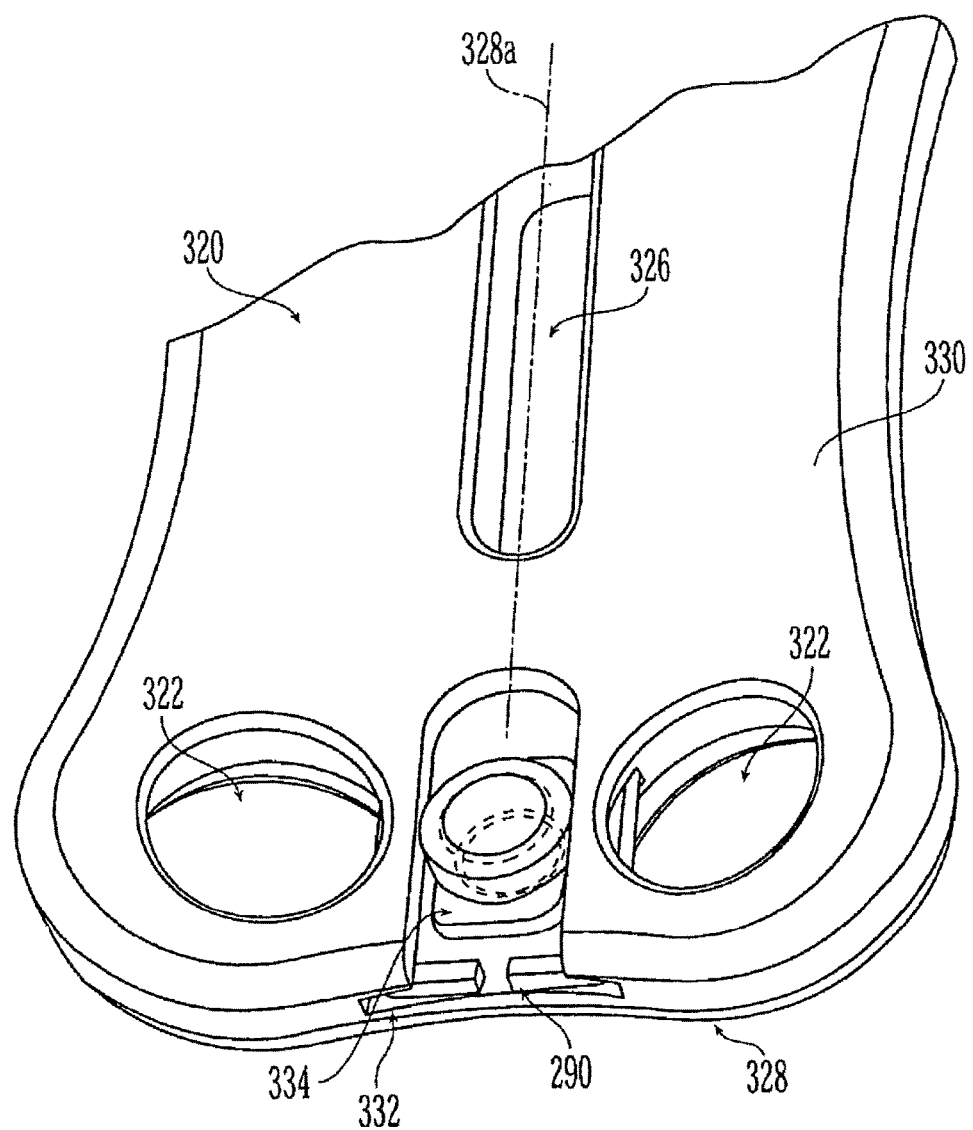
FIG. 16A shows a bottom perspective view of a plate and cam element used in a fourth embodiment of a fixation system.
Figure 16B:
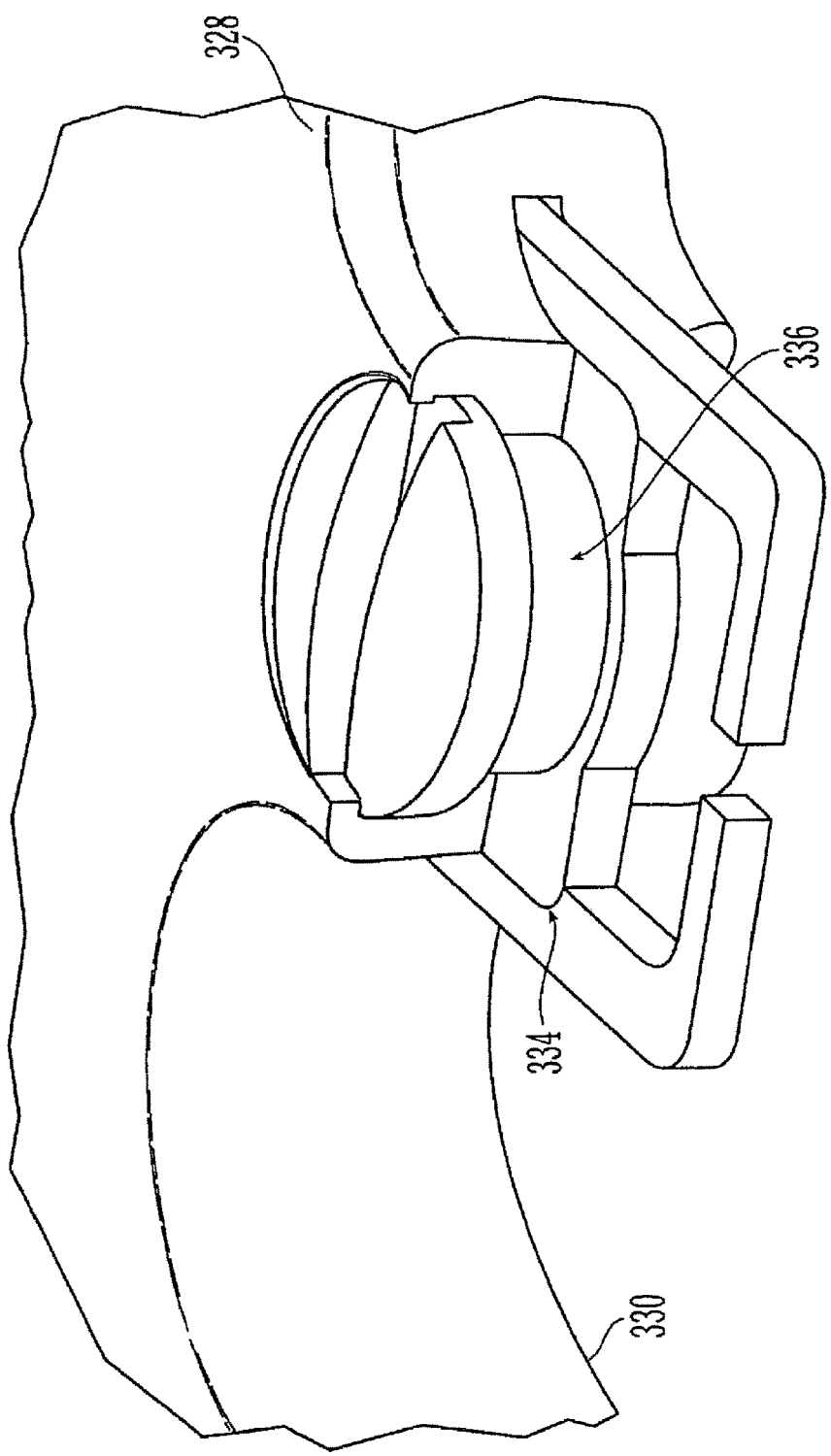
FIG. 16B shows a partial cross-sectional perspective view of the plate and cam element of FIG. 16A with the cam element in a locked position with respect to a captive clip.
Figure 16C:
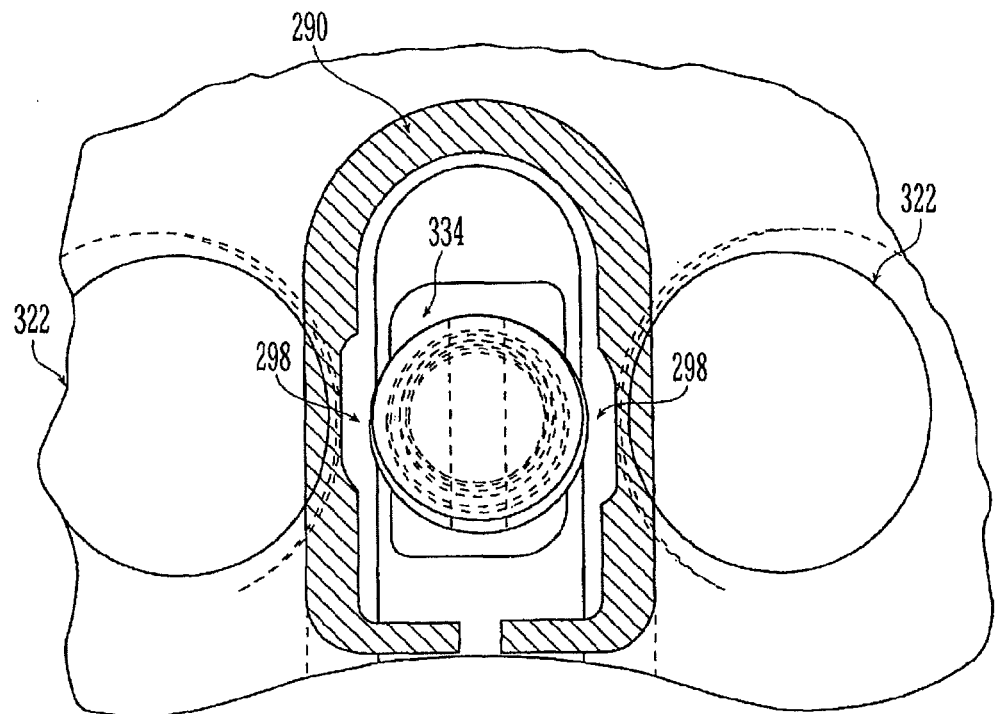
FIG. 16C shows a bottom view of the plate and cam element of FIG. 16A with the cam element in an unlocked position with respect to a captive clip.
Figure 16D:
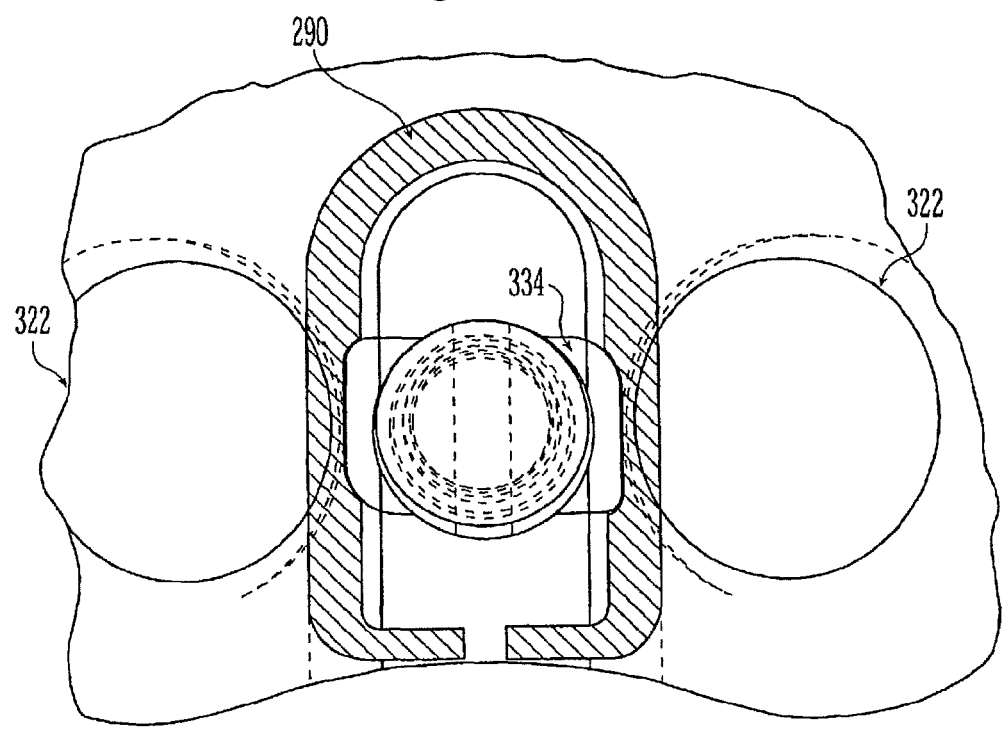
FIG. 16D shows a bottom view of the plate and cam element of FIG. 16A with the cam element in a locked position with respect to a captive clip.
Figure 17A:
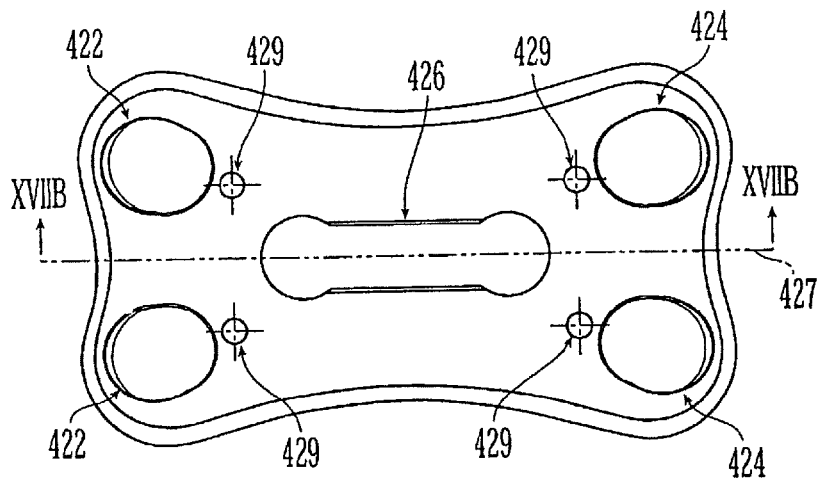
FIG. 17A shows a top view of a plate for use with a fifth embodiment of a fixation system.
Figure 17B:
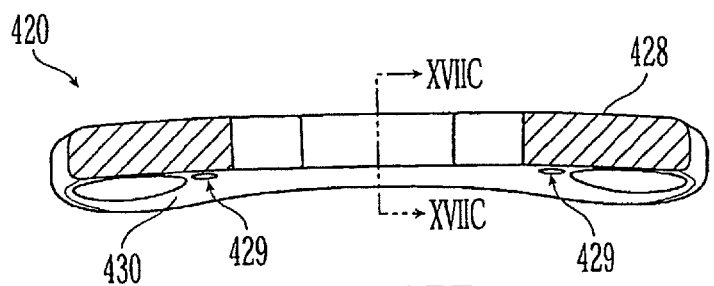
FIG. 17B shows a partial cross-sectional view taken along line XVIIB-XVIIB of the plate of FIG. 17A.
Figure 17C:
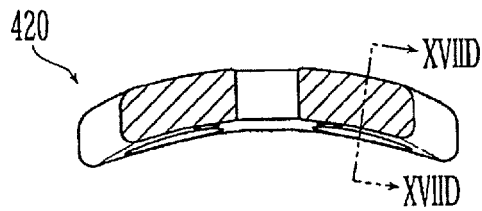
FIG. 17C shows a partial cross-sectional view taken along line XVIIC-XVIIC of the plate of FIG. 17B.
Figures 17D, 17E:
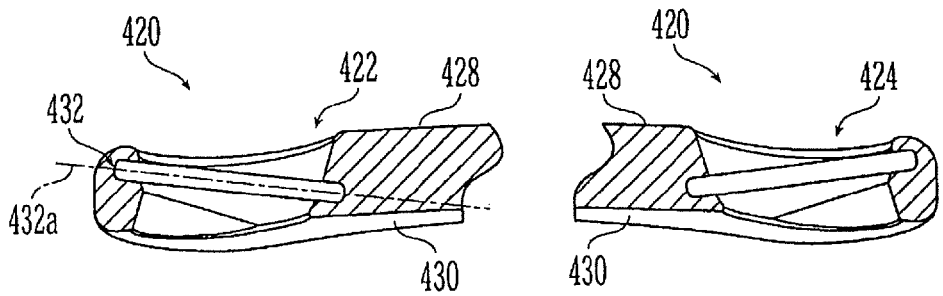
FIG. 17D shows a partial cross-sectional view taken along line XVIID-XVIID of the plate of FIG. 17C.
FIG. 17E shows another partial cross-sectional view taken along line XVIID-XVIID of the plate of FIG. 17C.

Turning to FIGS. 16A-16D, a fourth embodiment of a fixation system is shown. The fixation system includes a plate 320 with two pairs of circular fixation holes 222 (only one pair is shown in FIG. 16A). A slot 326 is aligned along central longitudinal axis 328a for receiving a drill/screw guide and for graft visualization. Preferably, slot 326 does not receive any fasteners. Each of fixation holes 322 extends between top and bottom surfaces 328, 330. Each pair of fixation holes 322 is partially intersected by a common slot 332. As shown in each of FIGS. 16A-16D, a captive clip 290 is inserted in slot 332 from a side, preferably cephalad or caudal, of plate 320. In an alternate embodiment, slot 332 is disposed transverse to central longitudinal axis 328a and such that it opens on a side of plate 320, preferably the cephalad and/or caudal sides. In addition, slot 332 alternatively may open on a side of plate 320 that extends between the cephalad and caudal sides of plate 320.

A cam element 334 is inserted from the bottom 330 of plate 320, and is received in recesses 298 of captive clip 290 to govern expansion and contraction thereof. Cam element 334 is turned using a locking screw 336 fastened thereto. In its unlocked position, shown in FIGS. 16A and 16C, captive clip 290 can freely expand and contract, and thus a fastener is not captured as securely by the clip. In its locked position, shown in FIGS. 168 and 16D, cam element 334 engages recesses 298, and thus compression of captive clip 290 is prevented by cam element 334 thereby permitting captive clip 290 to securely capture one or more fasteners inserted in fixation holes 322. In an exemplary preferred embodiment, cam element 334 has four rounded corners to facilitate engagement with recesses 298.

Turning to FIGS. 17A-20B, a fifth embodiment of a fixation system is shown. The fixation system includes a plate 420 with two pairs of fixation holes 422, 424. Fixation holes 422, 424 are circular in shape. Although plate 420 is provided with two pairs of fixation holes 422, 424, more than two pairs may instead be provided, for example so that plate 420 may span a greater length and thus be fastened to multiple locations along the spine. A "dogbone" shaped slot 426 is aligned along central longitudinal axis 427 for receiving a drill/screw guide and for graft visualization. Preferably, slot 426 does not receive any fasteners.

Each of fixation holes 422, 424 extends between top and bottom surfaces 428, 430 and includes an undercut 432. In one embodiment, undercut 432 is disposed transverse to top and bottom surfaces 428, 430, respectively, along line 432a, but other orientations are also possible as previously described with respect to other embodiments. Preferably, an undercut 432 extends completely around each of fixation holes 422, 424. At least one passage 429 extends transverse to each of the fixation holes 422, 424, preferably from bottom surface 428, and intersects an undercut 432 associated with the hole 422 or 424. Passages 429 are used for alignment of captive clips, as will be described shortly.

Figure 18A:
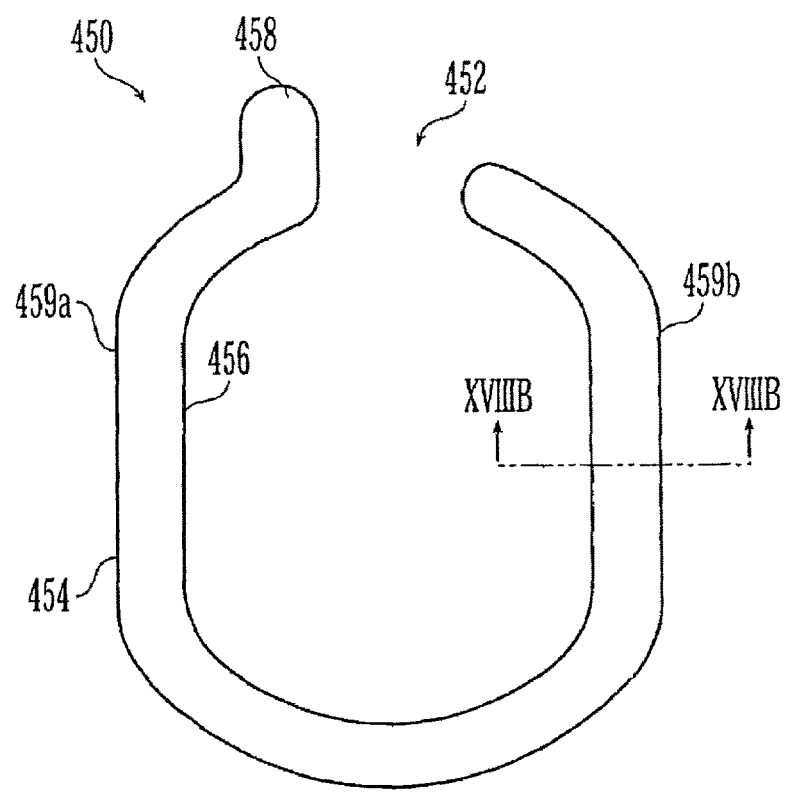
FIG. 18A shows a captive clip for use with the plate of FIG. 17A.
Figure 18B:
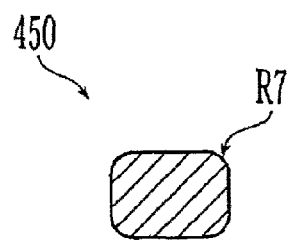
FIG. 18B shows a cross-sectional view taken along line XVIIIB-XVIIIB of the captive clip of FIG. 18A.
Figure 19A:
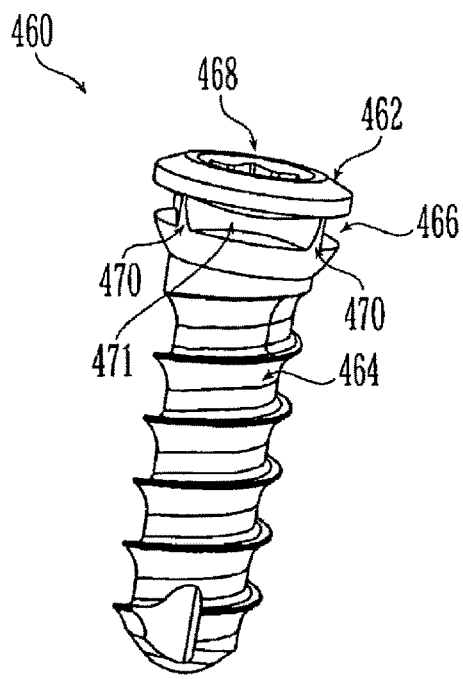
FIG. 19A shows a perspective view of another embodiment of a fastener.
Figure 19B:
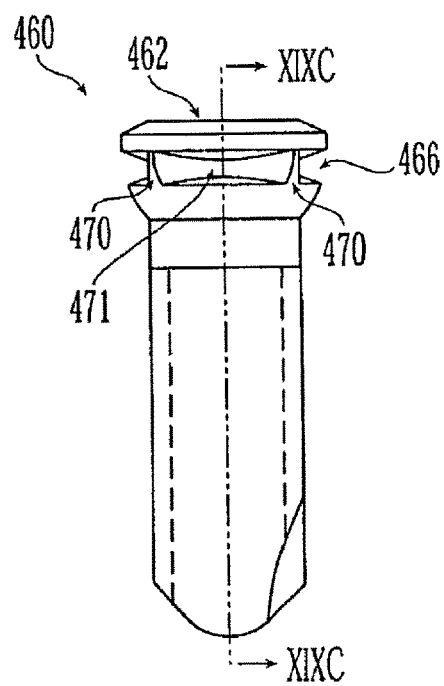
FIG. 19B shows a side view of the fastener of FIG. 19A.
Figure 19C:
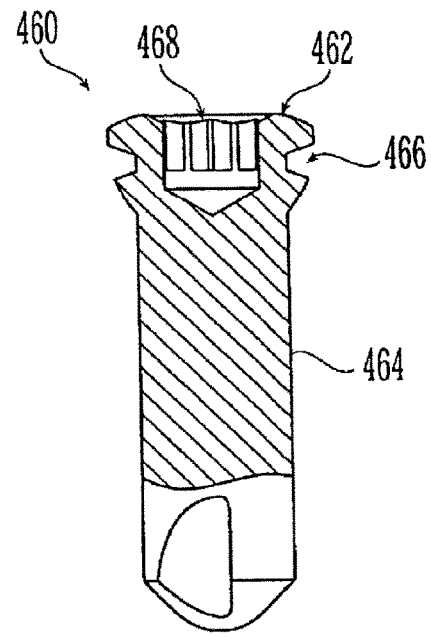
FIG. 19C shows a partial cross-sectional side view taken along line XIXC-XIXC of the fastener of FIG. 19B.
Figure 19D:
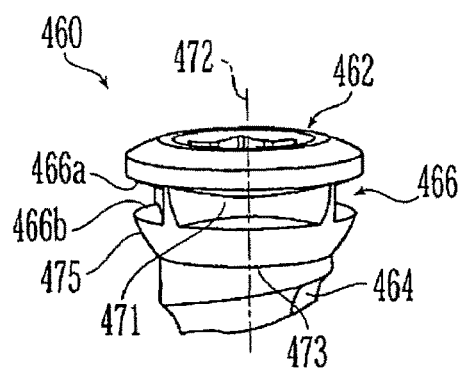
FIG. 19D shows a partial side view of the head of the fastener of FIG. 19A.
Figure 19E:
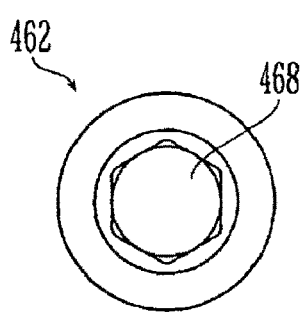
FIG. 19E shows a top view of the fastener of FIG. 19A.
Figure 19F:
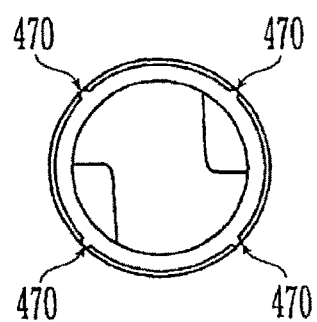
FIG. 19F shows a bottom view of the fastener of FIG. 19A.
Figure 19G:
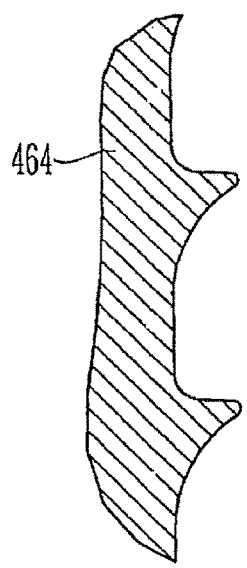
FIG. 19G shows a partial cross-sectional side view of the shaft and threads of the fastener of FIG. 19A.

Turning to FIGS. 18A and 18B, a generally U-shaped captive clip 450 is shown with a slit 452 that permits elastic expansion/compression of clip 450, as well as an outer edge 454, an inner edge 456, and generally parallel sides 459a, 459b. Clip 450 includes a generally rectangular cross-section, and in one embodiment, is provided with a radius R7 at edges 454 and 456 of between about 0.1 mm and about 0.2 mm. An end tab 458 extends from side 459a, preferably transverse to the plane of the page. In some embodiments, end tab 458 extends generally parallel to the plane of the page. When a captive clip 450 is installed in a fixation hole 422, 424, end tab 458 extends into a passage 429 so that captive clip 450 may be aligned and properly placed in undercut 432 in the fixation hole. In an exemplary preferred embodiment, captive clips 450 are pre-installed in fixation holes 422, 424 in plate 420 prior to installation of fasteners therein.

A captive clip 450 is provided for each fastener 460 around head 462. Preferably, clip 450 snap-fits around head 462 of a fastener 460 such that post-operative back-out of a fastener 460 from a hole 422, 424 is resisted. A fastener 460 retained on a captive clip 450 disposed in an undercut 432 of a circular hole 422, 424 may be permitted to toggle along a central axis of the hole.

As shown in FIGS. 19A-19G, an exemplar fastener 460 includes a head 462 with a self-tapping, threaded shaft 464. In an alternate embodiment, a self-drilling, threaded shaft 464 may be provided. Head 462 includes a perimetral groove 466 that is interrupted by four corners 470 separating back wall 471. In the exemplar embodiment of FIG. 19E, an instrument receiving portion 468 is hexagonal-shaped. However, in alternate embodiments, other shapes may be provided. Fastener 460 preferably is used for fixation to cancellous bone, although threading appropriate for fixation to cortical bone instead may be provided. In one preferred exemplary embodiment, perimetral groove 466 includes an upper portion 466a and a lower portion 466b that are disposed generally parallel to each other.

Head 462 preferably is partially spherical and includes a bottom section 475 extending to the top end 473 of shaft 464, with bottom section 475 tapering inward toward longitudinal axis 472 from perimetral groove 466 to top end 473. Advantageously, such tapering permits angulation of fastener 460 when disposed in a fixation hole 422, 424.

In use, fastener 460 is received in captive clip 450. The shaft 464 is initially screwed into bone until the partial-spherical head 462 of fastener 460 reaches captive clip 450. Upon further insertion of fastener 460 into captive clip 450, the partial-spherical head 462, particularly bottom section 475, bears against the inside edge 456 of captive clip 450 and expands captive clip 450. Once fastener 460 is inserted far enough, captive clip 450 contracts so that it "snaps" into perimetral groove 466 in head 462, thereby preventing fastener 460 from backing out of plate 420, as previously described.

Figure 20A:
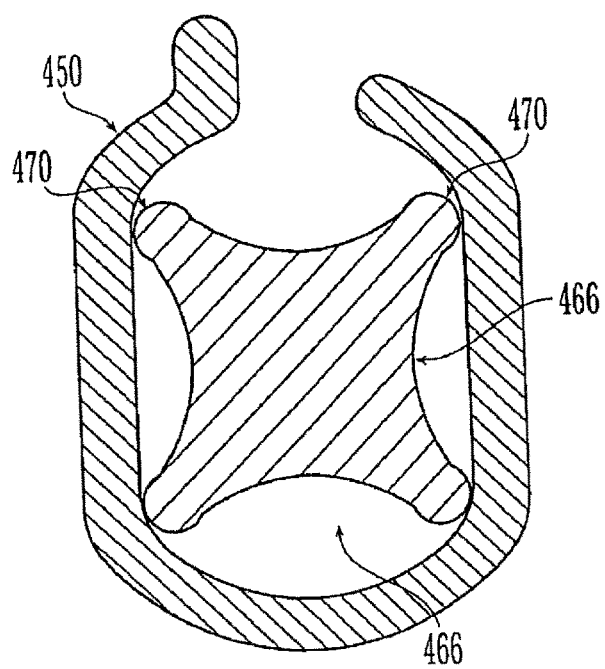
FIG. 20A shows a schematic of the captive clip of FIG. 18A in an unexpanded state with a cross-section of a screw head inserted through the clip.
Figure 20B:
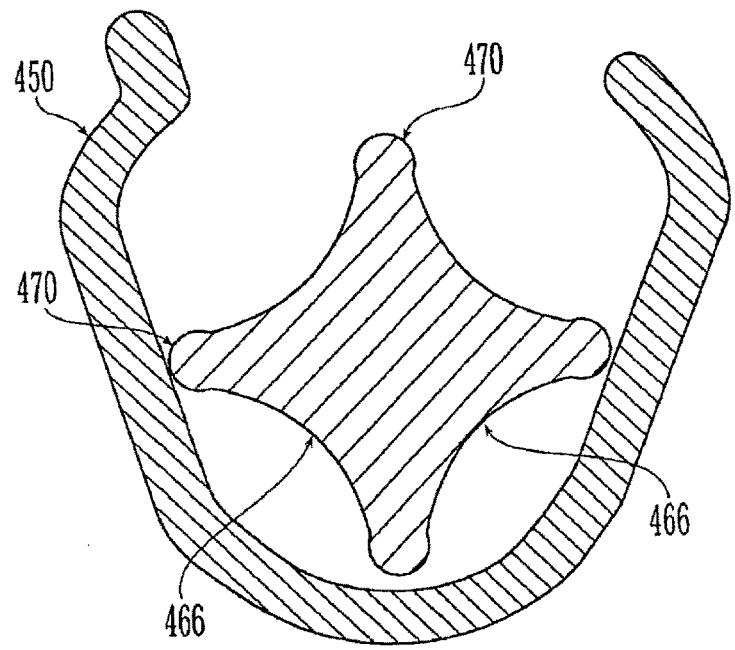
FIG. 20B shows a schematic of the captive clip of FIG. 18A in an expanded state with a cross-section of a screw head inserted through the clip.

As evident from FIGS. 20A and 20B, in some orientations, the four corners 470 of fastener 460 may be retained on captive clip 450 while the clip is in an unexpanded state. In other orientations, two of the corners act as cams on the inner wall 456 of the clip to elastically expand it such that the fastener is no longer locked by captive clip 450. Thus, it is possible to remove a fastener by turning the fastener to engage the cams with the clip to expand the clip.

A fastener 460, retained on captive clip 450, can toggle on captive clip 450 in a fixation hole 422, 424, because of the geometry of the perimetral groove 466 in head 462 of fastener 460 and the geometry of the fixation hole 422, 424. During toggling, captive clip 450 remains essentially fixed in place, while the axis of fastener 460 is allowed to angulate with respect to the central axis of the fixation hole 422, 424. In embodiments in which surfaces 466a, 466b of groove 466 are generally parallel to each other, toggling may be substantially limited.

Figure 21A:
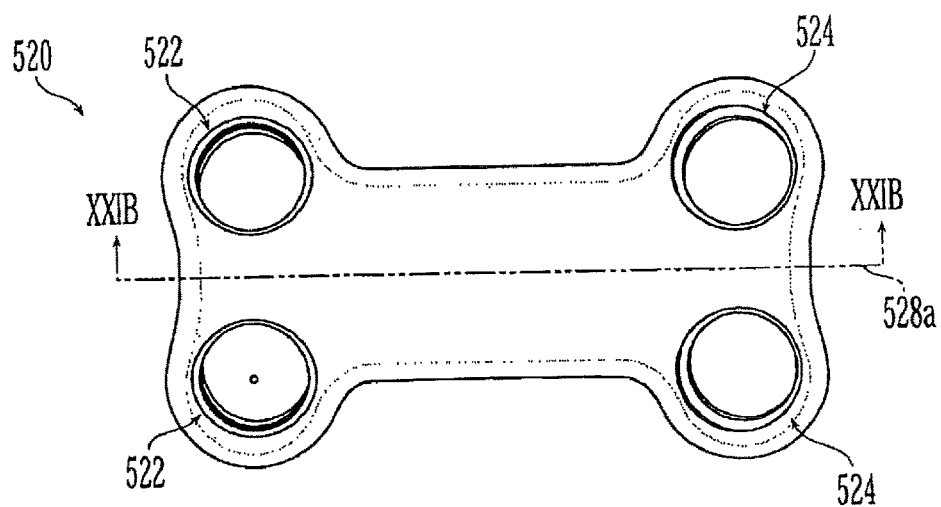
FIG. 21A shows a top view of a plate for use with a sixth embodiment of a fixation system.
Figure 21B:
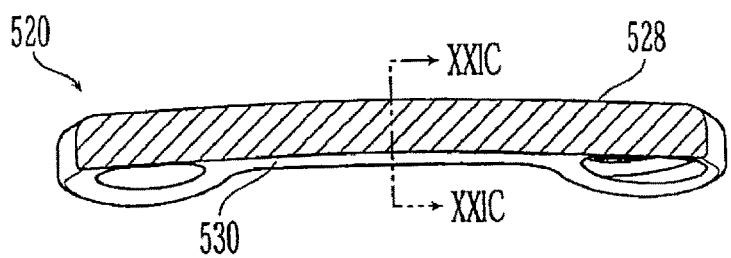
FIG. 21B shows a partial cross-sectional view taken along line XXIB-XXIB of the plate of FIG. 21A.
Figure 21C:
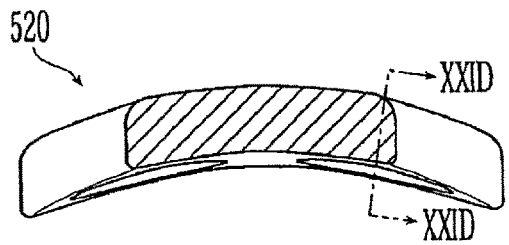
FIG. 21C shows a partial cross-sectional view taken along line XXIC-XXIC of the plate of FIG. 21B.
Figures 21D, 21E:
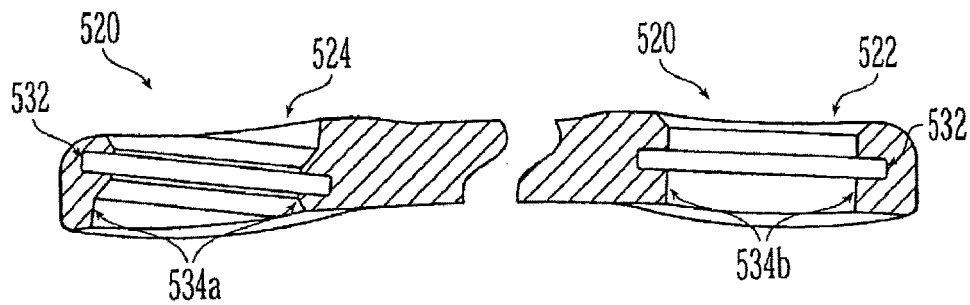
FIG. 21D shows a partial cross-sectional view taken along line XXID-XXID of the plate of FIG. 21C.
FIG. 21E shows another partial cross-sectional view taken along line XXID-XXID of the plate of FIG. 21C.
Figure 22:
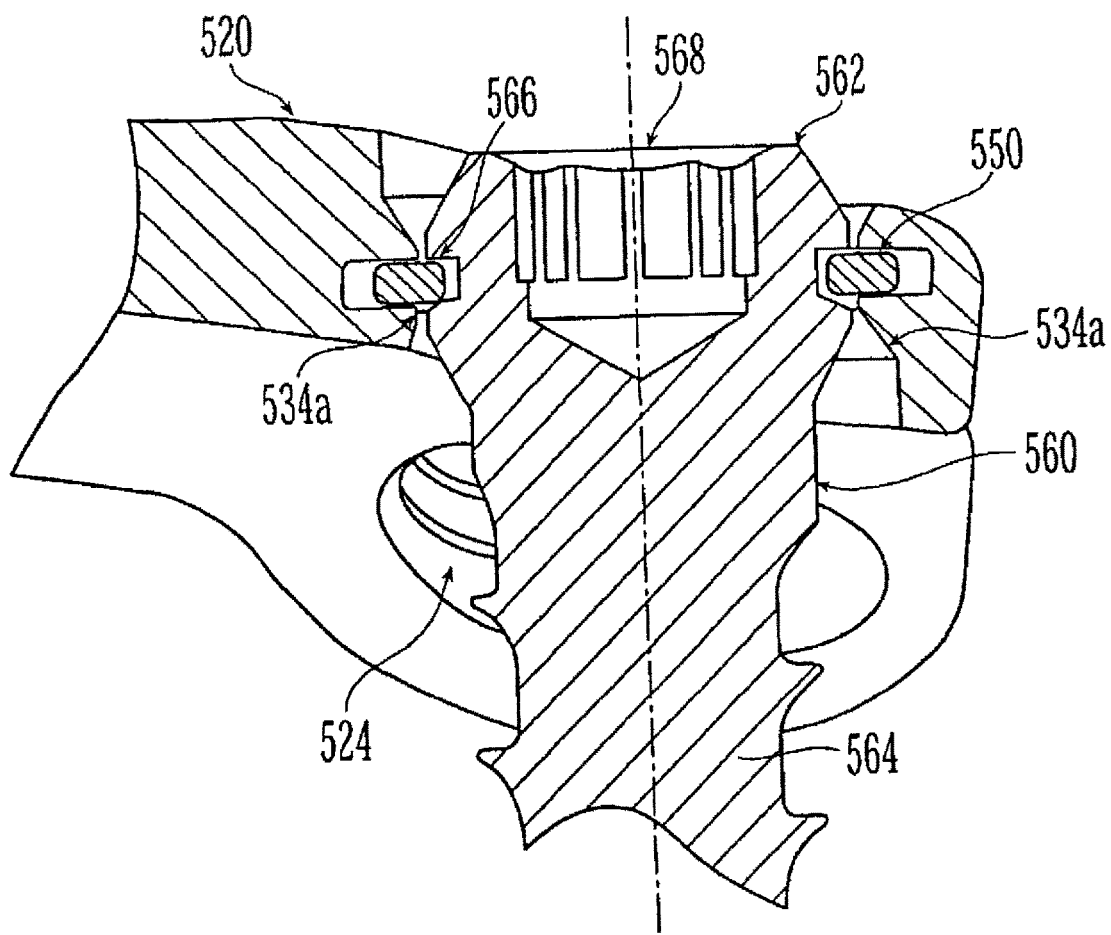
FIG. 22 shows a partial cross-sectional perspective view of the plate of FIG. 21A with a fastener and captive clip installed therein.

A sixth embodiment of a fixation system is shown in FIGS. 21A-22. The fixation system includes a plate 520 with two pairs of fixation holes 522, 524. Fixation holes 522, 524 are circular in shape. Although plate 520 is provided with two pairs of fixation holes 522, 524, more than two pairs may instead be provided, for example so that plate 520 may span a greater length and thus be fastened to multiple locations along the spine. Although no slot is provided along central longitudinal axis 528a for receiving a drill/screw guide and for graft visualization, one may be provided as described previously with respect to other embodiments.

Each of fixation holes 522, 524 extends between top and bottom surfaces 528, 530, respectively, and includes an undercut 532. In one embodiment, undercut 532 is disposed transverse to top and bottom surfaces 528, 530, respectively, but other orientations are also possible as previously described with respect to other embodiments. Preferably, an undercut 532 extends completely around each of fixation holes 522, 524.

The geometry of one pair of fixation holes 522, preferably the caudal pair of holes, is sized such that movement of a fastener 560 therein is very limited. The geometry of the remaining pair of fixation holes 524 allows a fastener 560 to toggle between about 5° and about 30°, and more preferably between about 15° and about 20°, as shown in FIG. 22. In particular, a fastener 560, shown in FIG. 22, is retained on a captive clip 550. The fastener 560 may toggle on captive clip 550 in fixation hole 524 because of the geometry of perimetral groove 566 in the head 562 of the fastener and the geometry of fixation hole 524. In particular, lower portion 534a widens proximate bottom surface 530 of plate 520. The captive clip 550 preferably remains fixed in place, while the axis of fastener 560 is allowed to angulate with respect to the axis of fixation hole 524.

With reference to FIGS. 23A-29, a seventh embodiment of a fixation system is shown. Plates 620, 720, 820, 920 represent "one level," "two level," "Three level," and "four level" constructions, respectively. Each "level" is provided by one or more fixation holes, and preferably pairs of adjacent fixation holes, bridging two vertebrae. Thus, a first level plate bridges two vertebrae and includes at least one fixation hole, preferably two adjacent fixation holes for each vertebrae, while a second level plate bridges three vertebrae and includes at least one fixation hole, preferably two adjacent fixation holes for each vertebrae. For example, plate 620 has two pairs of fixation holes 622, 624, and thus only represents one level; in contrast, plate 720 has three pairs of fixation holes, and thus the middle pair of fixation holes is adjacent two other pairs thus forming a two level construction.

As can be seen from FIGS. 23A-29, the construction of plates 620, 720, 820, 920 is very similar, and thus although plate 620 will be described in detail herein, the description of plate 620 applies also to plates 720, 820, 920.

Referring to FIGS. 23A and 27A-27E, the fixation system includes a plate 620 with two pairs of fixation holes 622, 624. Fixation holes 622, 624 are circular in shape. A "figure eight" shaped slot 626 is aligned along central longitudinal axis 628a for receiving a drill/screw guide and for graft visualization. Preferably, slot 626 does not receive any fasteners, and is beveled along upper inner edge 626a at an angle α between about 30° and about 60°, and more preferable about 45°. It should be noted that as the length of plates 620, 720, 820, 920 increases along the central longitudinal axis, slot 626 becomes elongated and generally "dog-bone" shaped as shown for example in FIGS. 25A and 26A.

Each of fixation holes 622, 624 extends between top and bottom surfaces 628, 630 and includes an undercut 632. In one embodiment, undercut 632 is disposed transverse to top and bottom surfaces 628, 630, respectively, but other orientations are also possible as previously described with respect to other embodiments. Preferably, an undercut 632 extends completely around each of fixation holes 622, 624. At least one passage 629 extends transverse to each of the fixation holes 622, 624, preferably from bottom surface 628, and intersects undercut 632 associated with the hole 622 or 624. In some embodiments, passage 629 may extend generally parallel to each of the fixation holes 622, 624, preferably from bottom surface 628, and intersects undercut 632 associated with the hole 622 or 624. Passages 629 are used for alignment of captive clips, as will be described shortly. In the preferred exemplary embodiment, holes 629 are disposed along lines generally parallel to central longitudinal axis 628a, for example along line 628b.

Figure 28A:
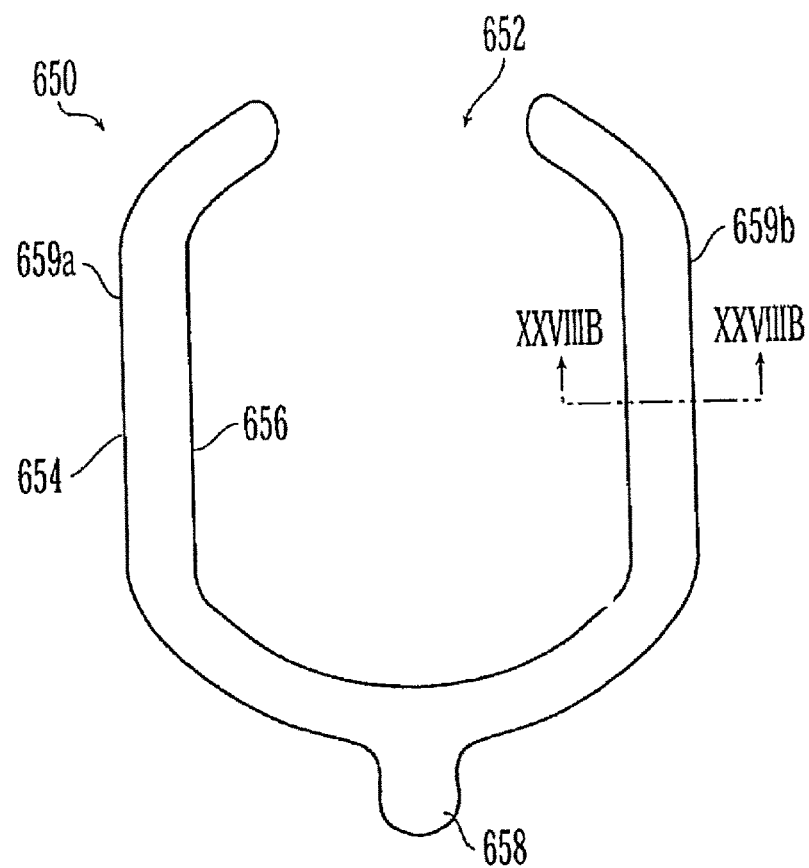
FIG. 28A shows a captive clip for use with the plates of FIGS. 23A, 24A, 25A, and 26A.
Figure 28B:
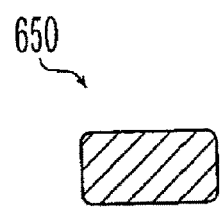
FIG. 28B shows a cross-sectional view taken along line XXVIIIB-XXVIIIB of the captive clip of FIG. 28A.

As shown in FIGS. 28A and 28B, a generally "wishbone-shaped" captive clip 650 includes a slit 652 that permits elastic expansion/compression of clip 650, as well as an outer edge 654, an inner edge 656, and generally parallel sides 659a, 659b. Clip 650 also includes a generally rectangular cross-section, as shown in FIG. 28B. In a preferred exemplary embodiment, an end tab 658 extends between, and preferably halfway between, sides 659a, 659b and transverse to the plane of the page. In some embodiments, end tab 658 extends generally parallel to the plane of the page. When a captive clip 650 is installed in a fixation hole 622, 624, end tab 658 extends into passage 629 so that captive clip 650 may be aligned and properly placed in the fixation hole. Preferably, captive clips 650 are pre-installed in fixation holes 622, 624 in plate 620 prior to installation of fasteners therein.

Referring to FIG. 29, a captive clip 650 is provided for fastener 660 around head 662. Preferably, clip 650 snap-fits around head 662 of fastener 660 such that post-operative back-out of fastener 660 from hole 622, 624 is resisted. Preferably, captive clip 650 is disposed in an undercut 632 of a fixation hole 622, 624 and is permitted to toggle along a central axis of the hole, as shown for example in FIG. 29 as indicated for example by arrows A.

Figure 30A:
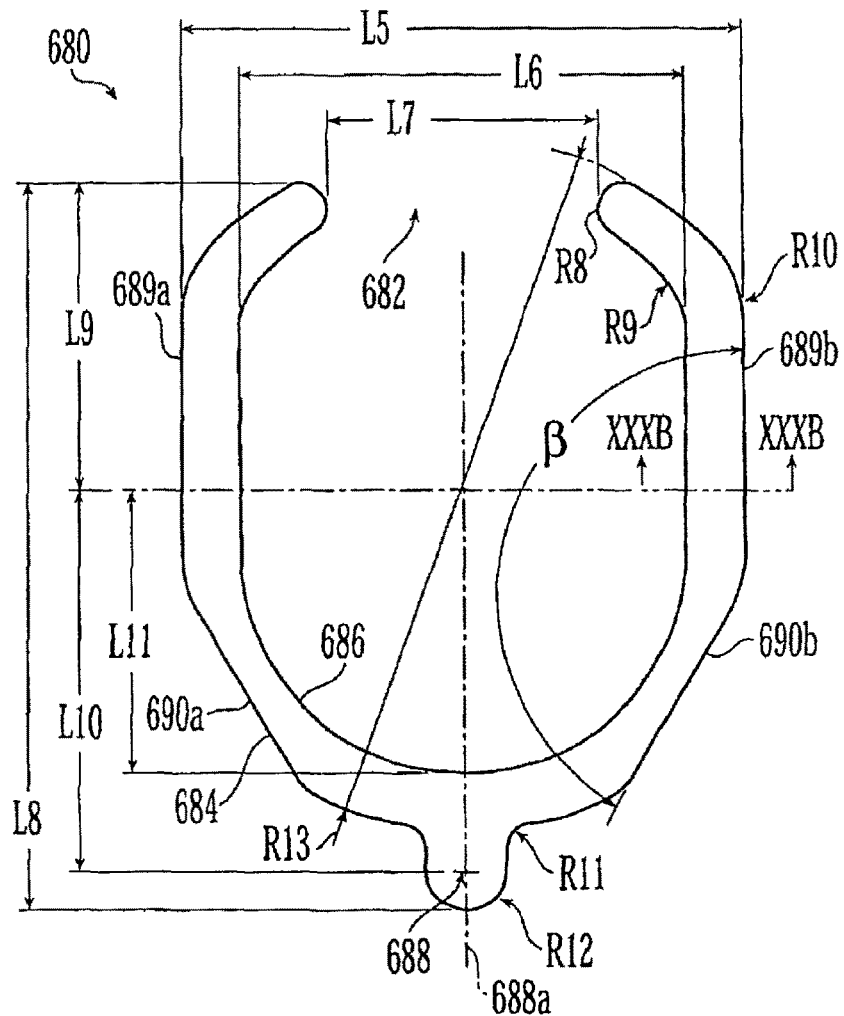
FIG. 30A shows another embodiment of a captive clip.
Figure 30B:
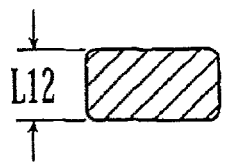
FIG. 30B shows a cross-sectional view taken along line XXXB-XXXB of the captive clip of FIG. 30A.
Figure 30C:
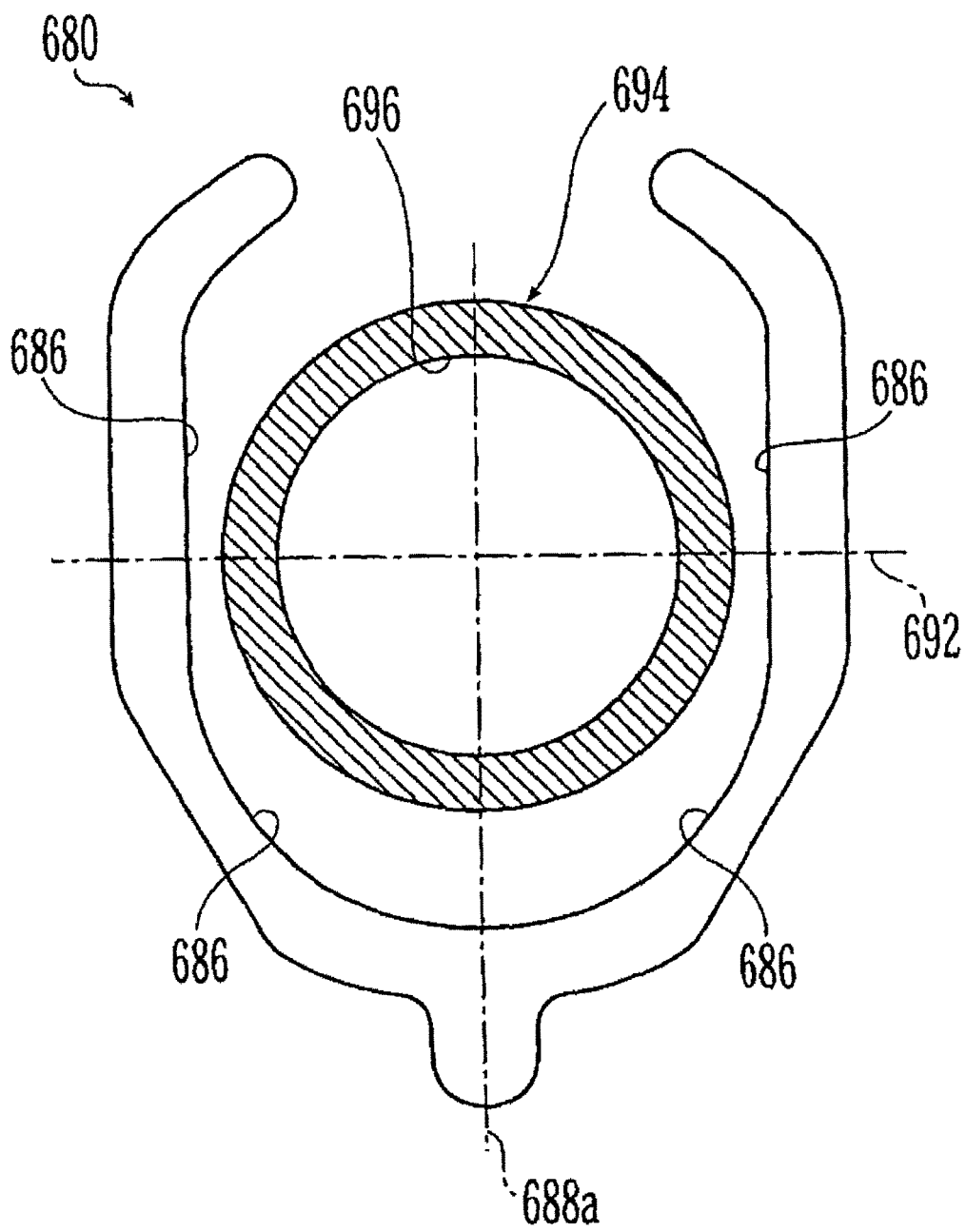
FIG. 30C shows another view of the captive clip of FIG. 30A along with a cross-section of a fastener head taken along the minor diameter of a perimetral groove in the fastener head.

Another preferred embodiment of a "wishbone-shaped" captive clip 680 is shown in FIGS. 30A to 30C. Similar to the captive clip 650 shown in FIGS. 28A and 28B, captive clip 680 includes a slit 682 that permits elastic expansion/compression of clip 680, as well as an outer edge 684, an inner edge 686, and generally parallel sides 689a, 689b. Clip 680 also includes a generally rectangular cross-section, as shown in FIG. 30B. In a preferred exemplary embodiment, an end tab 688 extends between, and preferably halfway between, sides 689a, 689b, along clip central longitudinal axis 688a and transverse to the plane of the page. In some embodiments, end tab 688 extends generally parallel to the plane of the page. When captive clip 680 is installed in fixation hole 622, 624, end tab 688 extends into a passage 629 so that captive clip 680 may be aligned and properly placed in the fixation hole. Preferably, captive clips 680 are pre-installed in fixation holes 622, 624 in plate 620 prior to installation of fasteners therein. Preferably, the captive clips 680 are sized and configured so that once installed in the bone plate they are fixed in position. In the embodiment of the clip shown in FIG. 30A, the corners of the clip are wedged into the undercut so that movement of the clip in the undercut is prevented. In addition, once the fastener is inserted in the captive clip, the captive clip is even more securely wedged into position to prevent movement in the undercut.

A preferred exemplary embodiment of captive clip 680 includes the following dimensions: L5 of about 5.5 mm, L6 of about 4.4 mm, L7 of about 2.5 mm, L8 of about 7.2 mm, L9 of about 3 mm, L10 of about 3.8 mm, and L11 of about 2.85 mm. Captive clip 680 also has a thickness L12 of between about 0.3 mm and about 0.4 mm, more preferably about 0.37 mm. Preferred radii of curvature include: R8 of about 0.25 mm, R9 of about 2.8 mm, R10 of about 1 mm, R11 of about 0.3 mm, R12 of about 0.4 mm, and R13 of about 6.8 mm. A preferred angle β between outer edges of straight portions 689a, 689b and adjacent outer edges of straight portions 690a, 690b, respectively, is about 150°. Preferably, captive clip 680 is symmetric about central longitudinal axis 688a.

Advantageously, as shown for example in FIG. 30C, captive clip 680 is sized such that a fastener has a greater freedom to toggle in some directions as compared to other directions. For example, axis 688a is oriented parallel to the cephalad-caudal direction of a plate, while central axis 692 may be oriented perpendicular to axis 688 and parallel to the medial-lateral direction of the plate. A cross-section of an exemplary fastener head 694 is also shown, with the cross-section taken through the center of a perimetral groove in head 694 as described in the embodiments of fasteners disclosed herein. An outer edge 696 of the perimetral groove in head 694 is relatively close to edge 686 of captive clip 680 proximate central axis 692, while outer edge 696 is spaced a greater amount from edge 686 of captive clip 680 proximate axis 688a. Thus, toggling of the fastener is more limited in the direction of axis 692 because fastener head 694 may only be angulated until it contacts edge 686 which serves as a stop. In one preferred exemplary embodiment, a fastener inserted in captive clip 680 is permitted to toggle through between about 0° and about 32° along the plane extending perpendicular to the page through line 688a, while only being permitted to toggle through between about 0° and about 20° along the plane extending perpendicular to the page through line 692. Preferably, a fastener is permitted a greater freedom to toggle in the cephalad-caudal direction of a plate.

The preferred exemplary embodiment of captive clip 680, as well as each of the other captive clips described herein, preferably is formed of Elgiloy® (Cobalt-Chromium-Nickel alloy), ASTM F-1058 Grade I, burr free and electropolished. Preferably, each of the captive clips of the present invention may have high strength, ductility and good mechanical properties including an ultimate tensile strength between about 250,000 psi and about 350,000 psi (about 1,700 MPa and 2,000 MPa, respectively), a hardness (HRC) of between about 45 and about 60, an elastic modulus of up to about 30,000,000 psi (about 270 GPa), excellent fatigue life, and corrosion resistance. Alternatively, each of the captive clips described herein may be formed of another elastic material such as Nitinol superelastic alloy memory material per ASTM-2063.

Referring to FIGS. 31A to 31D, an eighth embodiment of a fixation system is shown. A plate 1020 is provided with one or more pair(s) of fixation holes 1022 that are generally "keyhole-shaped" and oblong, and one or more pair(s) of fixation holes 1024 that are generally circular. Each of the circular and keyhole-shaped holes includes an undercut 1026 that receives an "omega-shaped" captive clip 1028. Captive clip 1028 includes a pair of generally parallel sides 1030a, 1030b and two end tabs 1032a, 1032b protruding from each side 1030a, 1030b, respectively.

The geometry of fixation holes 1022, 1024 and their associated undercuts 1026 is sized such that movement of a captive clip 1028 once seated in an undercut 1026 is prevented, except that the undercuts 1026 accommodate elastic expansion of captive clip 1028 as previously explained. One tab 1032a, 1032b of captive clip 1028 is received in a hole 1034 that extends from undercut 1026 to a side of plate 1020, while the other tab 1032a, 1032b is received in a hole 1036 that extends from undercut 1026 toward the midline 1036 of plate 1020. Tabs 1032a, 1032b are used to align the "omega-shaped" captive clip 1028 in plate 1020. Preferably, captive clip 1028 is symmetrical about clip central axis 1029. Captive clip 1028 also preferably is installed in plate 1020 such that central axis 1029 is parallel midline 1036 of plate 1020 with intermediate portion 1031 of clip 1028 oriented so as to not interfere with movement of a fastener 1040 along the length of fixation hole 1022.

The "keyhole" shaped fixation holes 1022 include a rounded portion 1038 in which a head 1040a of a fastener 1040 is received, and a straight portion 1042 with an integrally formed ridge 1044 that may extend about the length of straight portion 1042 and under which the head 1040a is permitted to move. Captive clips 1028 are disposed in each rounded portion.

In use, the shaft 1040b of fastener 1040 is initially screwed into bone through the rounded portion 1038 of fixation hole 1022 until the partial-spherical head 1040a of fastener 1040 reaches captive clip 1028. Upon further insertion of fastener 1040 into captive clip 1028, the partial-spherical head 1040a bears against the inside edge 1046 of captive clip 1028 and expands the captive clip. Once fastener 1040 is inserted far enough, captive clip 1028 contracts so that it "snaps" into the perimetral groove 1050 in the head 1040a, thereby preventing fastener 1040 from backing out of plate 1020, as previously described. Fastener 1040 is then allowed to travel along the length of fixation hole 1022, for example under integrally formed ridge 1044 of the plate which provides additional resistance to back-out of fastener 1040. However, in order to allow shaft 1040b to be removed from the bone without interference from ridge 1044 on the straight portion 1042 of the "keyhole-shaped" fixation holes 1022, fastener 1040 must be moved so that head 1040a is disposed proximate the "omega-shaped" captive clip 1028. As described previously, captive clip 1028 may then be elastically expanded to permit removal of fastener 1040. With respect to the pair of circular holes 1024, again, the screw may be removed by expansion of the captive clip 1028.

Thus, a fastener 1040 disposed in a "keyhole-shaped" fixation hole 1022 is permitted to travel (slide) along the longitudinal axis of the hole 1022. The fastener 1040 can slide along the parallel sides 1030a, 1030b of the "omega-shaped" captive clip 1028 or under the integrally formed ridge 1044. A fastener disposed in a circular hole may be permitted to toggle but remains relatively stationary also as previously described.

Figure 31A:
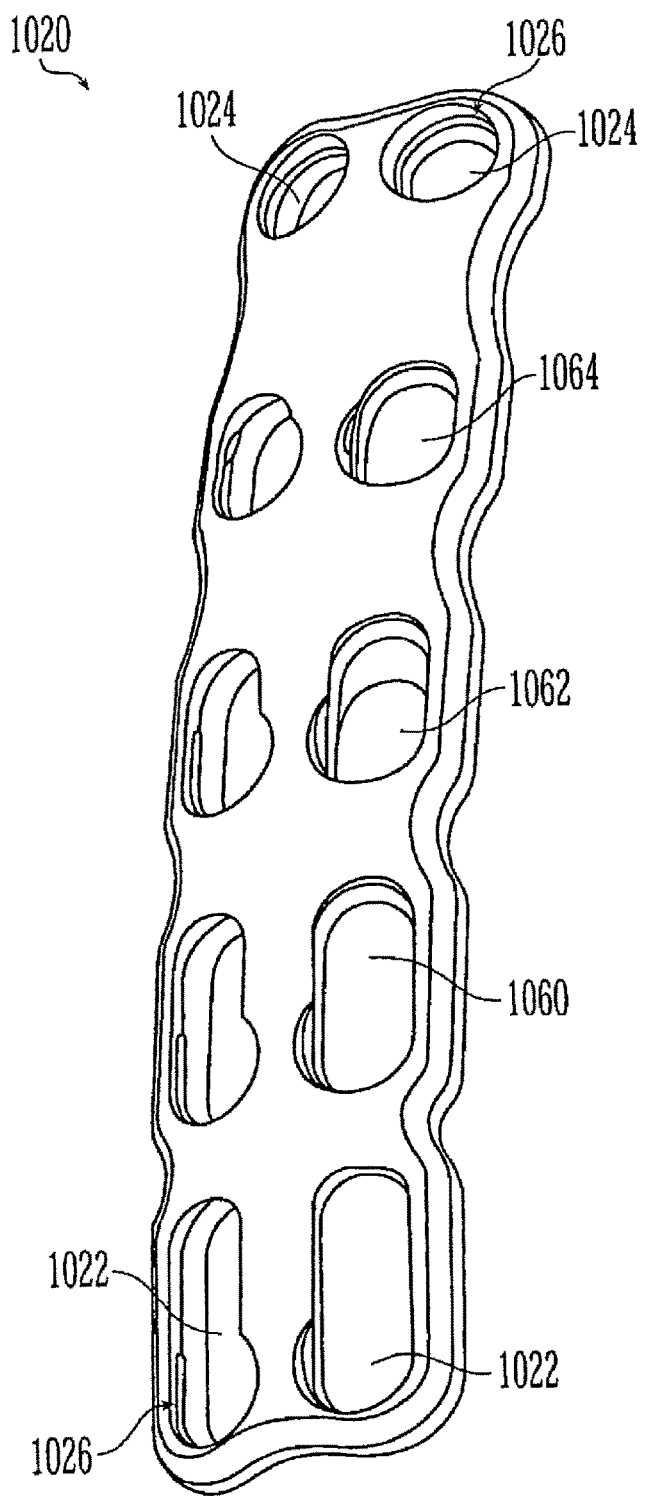
FIG. 31A shows a perspective view of a four level plate for use with an eighth embodiment.
Figure 31B:
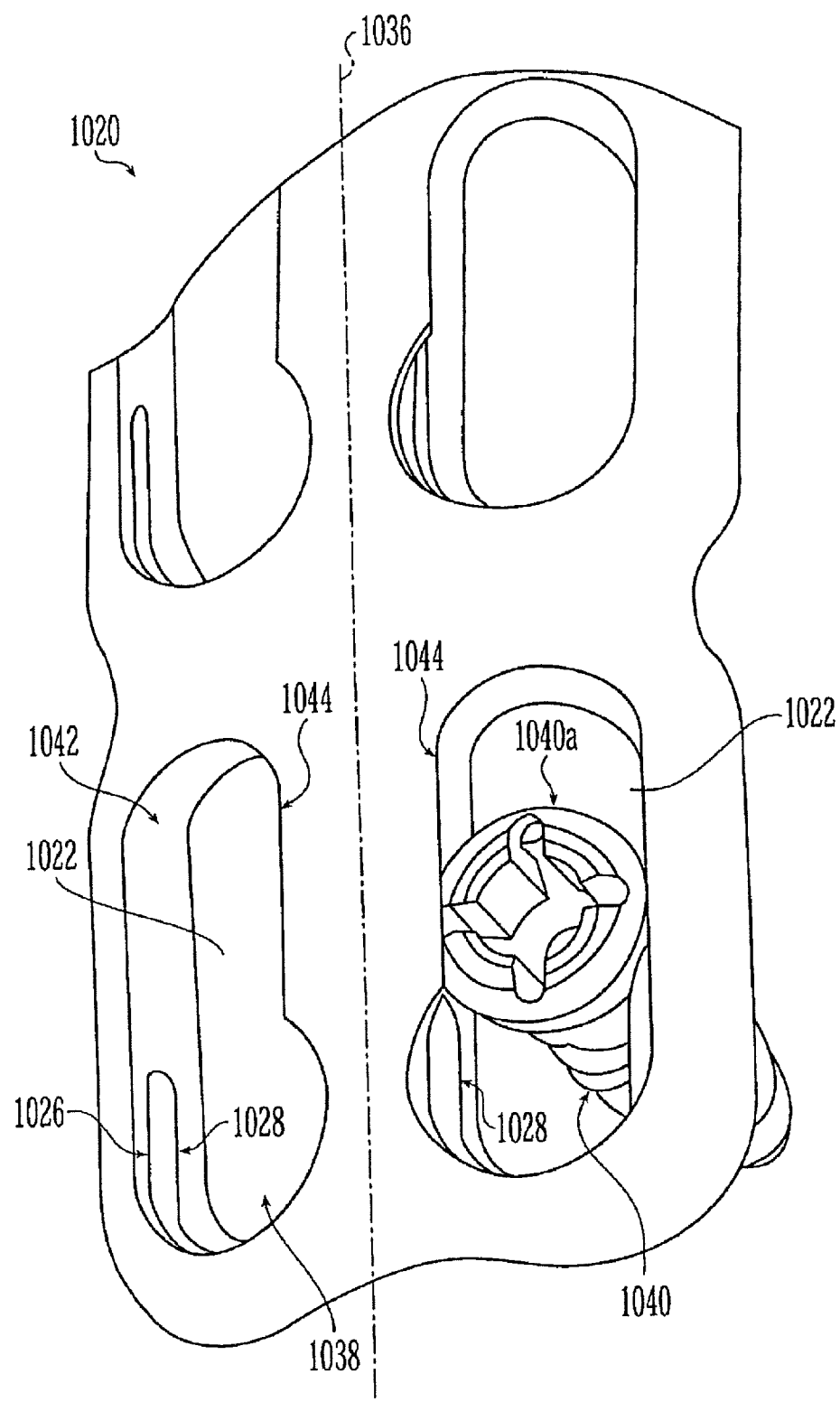
FIG. 31B shows a partial perspective view of the plate of FIG. 31A with captive clips and a fastener installed therein.
Figure 31C:
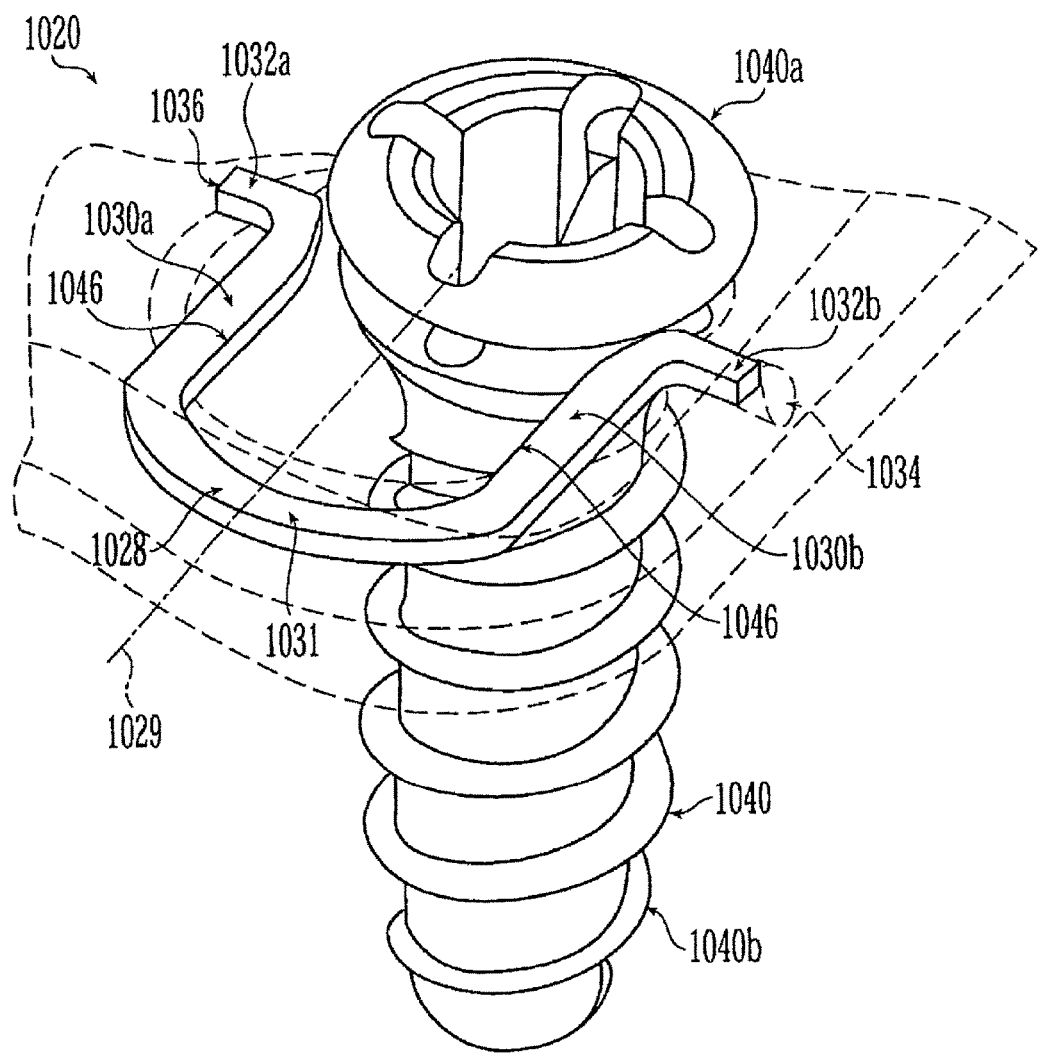
FIG. 31C shows a partial cross-sectional perspective view of the plate of FIG. 31A with a captive clip and a fastener installed therein.
Figure 31D:
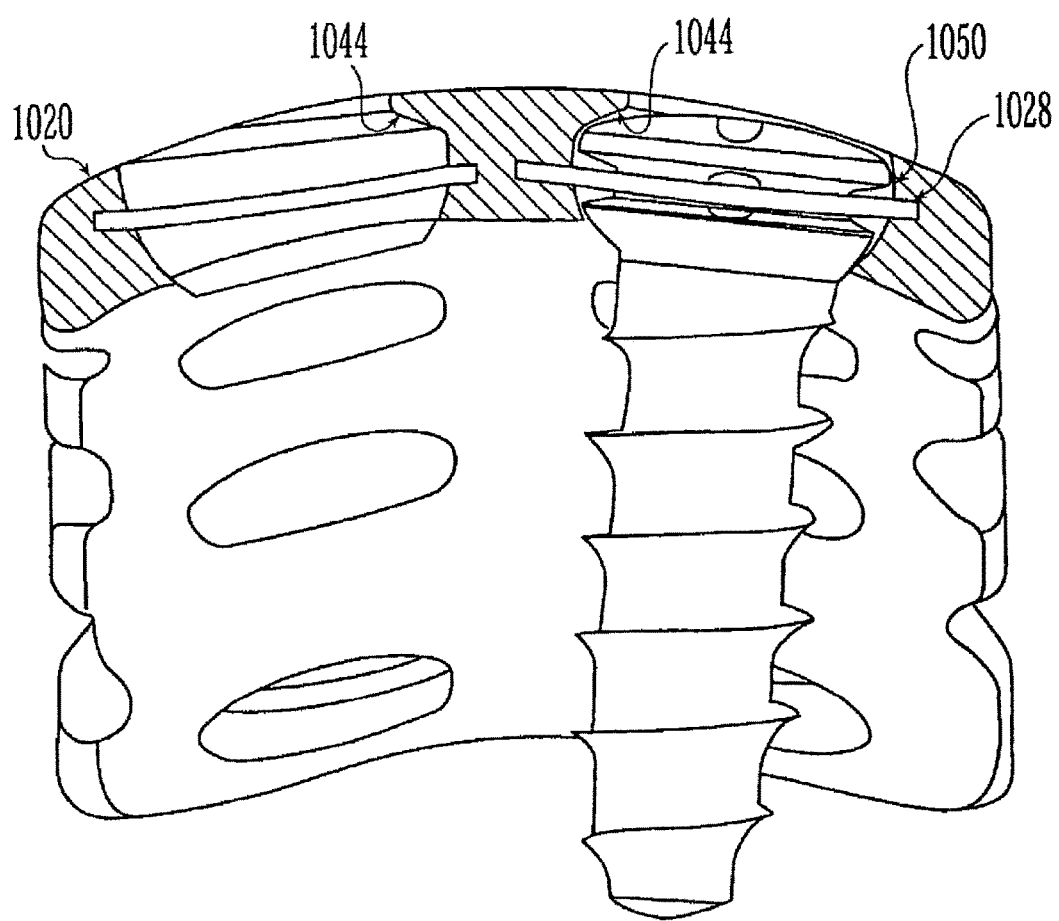
FIG. 31D shows another partial cross-sectional perspective view of the plate of FIG. 31A with captive clips and fasteners installed therein.

It should be noted that plate 1020 shown in FIG. 31A is a four level construct, and includes five pairs of holes. Plate 1020 thus includes three additional pairs of "keyhole-shaped" fixation holes 1060, 1062, 1064. In alternate embodiments of plate 1020, more than one pair of circular fixation holes may be provided, or as few as one "keyhole-shaped" fixation hole may be provided. While no slots are provided along midline 1036 of plate 1020, slots may be included as described with respect to other plate embodiments.

Figure 31E:
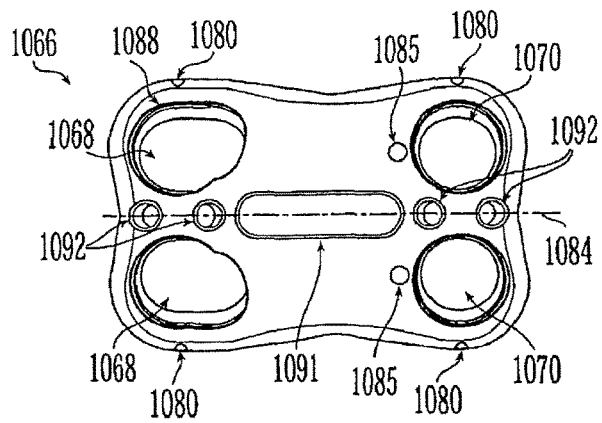
FIG. 31E shows a top view of another embodiment of a plate.
Figure 31F:
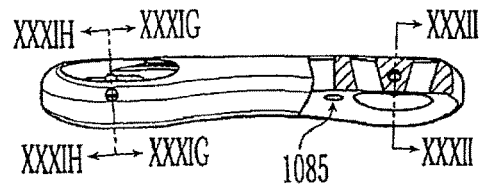
FIG. 31F shows a partial cross-sectional side view of the plate of FIG. 31E.
Figure 31G:
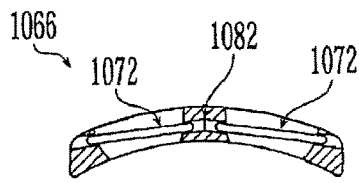
FIG. 31G shows a cross-sectional view taken along line XXXIG-XXXIG of the plate of FIG. 31E.
Figure 31H:
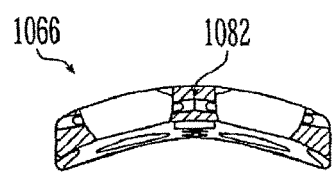
FIG. 31H shows a cross-sectional view taken along line XXXIH-XXXIH of the plate of FIG. 31E.
Figure 31I:
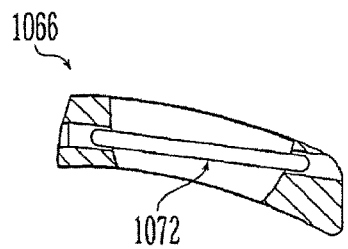
FIG. 31I shows a cross-sectional view taken along line XXXII-XXXII of the plate of FIG. 31E.
Figure 31J:
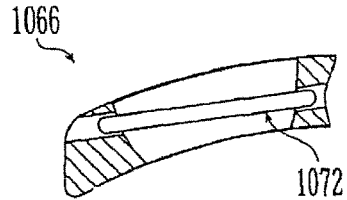
FIG. 31J shows a cross-sectional view of a keyhole-shaped fixation hole of the plate of FIG. 31E taken in the circular portion of the fixation hole along line XXXIG-XXXIG.
Figure 31K:
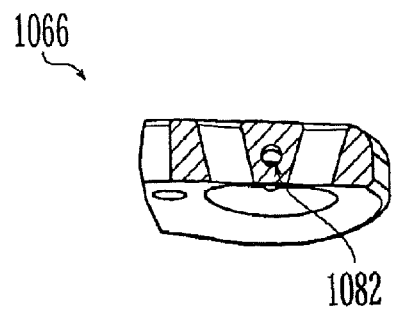
FIG. 31K shows a partial cross-sectional side view taken along the midline 1084 of the plate of FIG. 31E proximate a circular fixation hole.
Figure 31L:
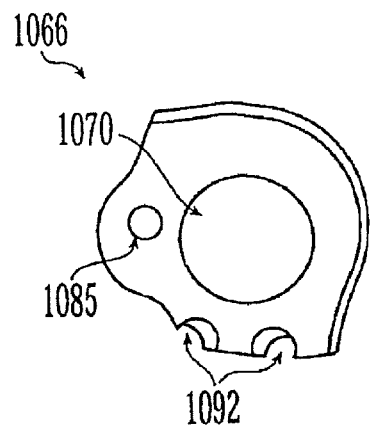
FIG. 31L shows a partial bottom view of a circular fixation hole of the plate of FIG. 31E.
Figure 31M:
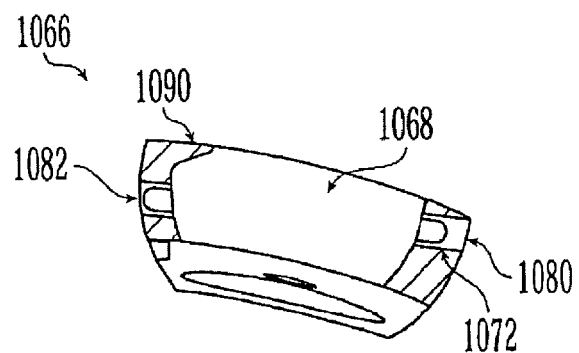
FIG. 31M shows a partial cross-sectional side view of a keyhole-shaped fixation hole of the plate of FIG. 31E taken in the straight portion of the fixation hole along line XXXIH-XXXIH.
Figure 31N:
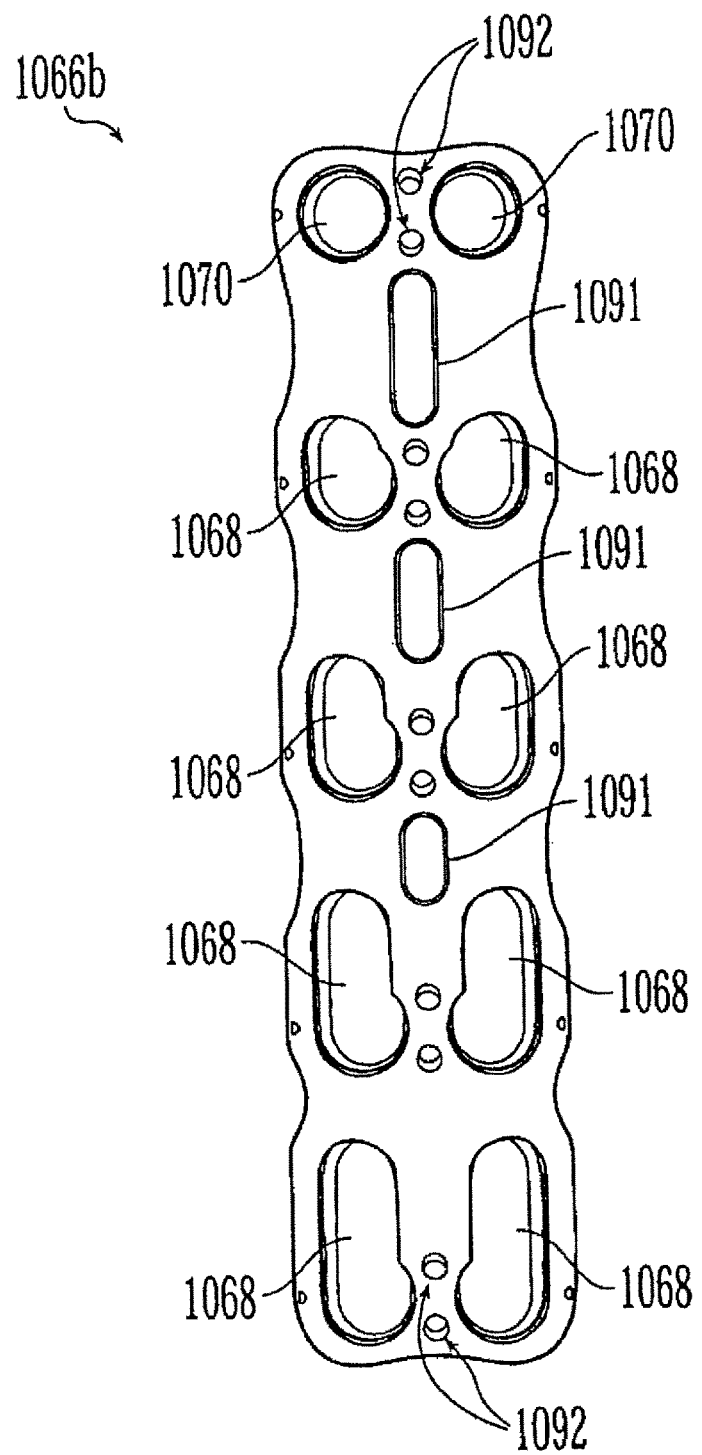
FIG. 31N shows a top view of another multi-level fixation plate.
Figure 31O:
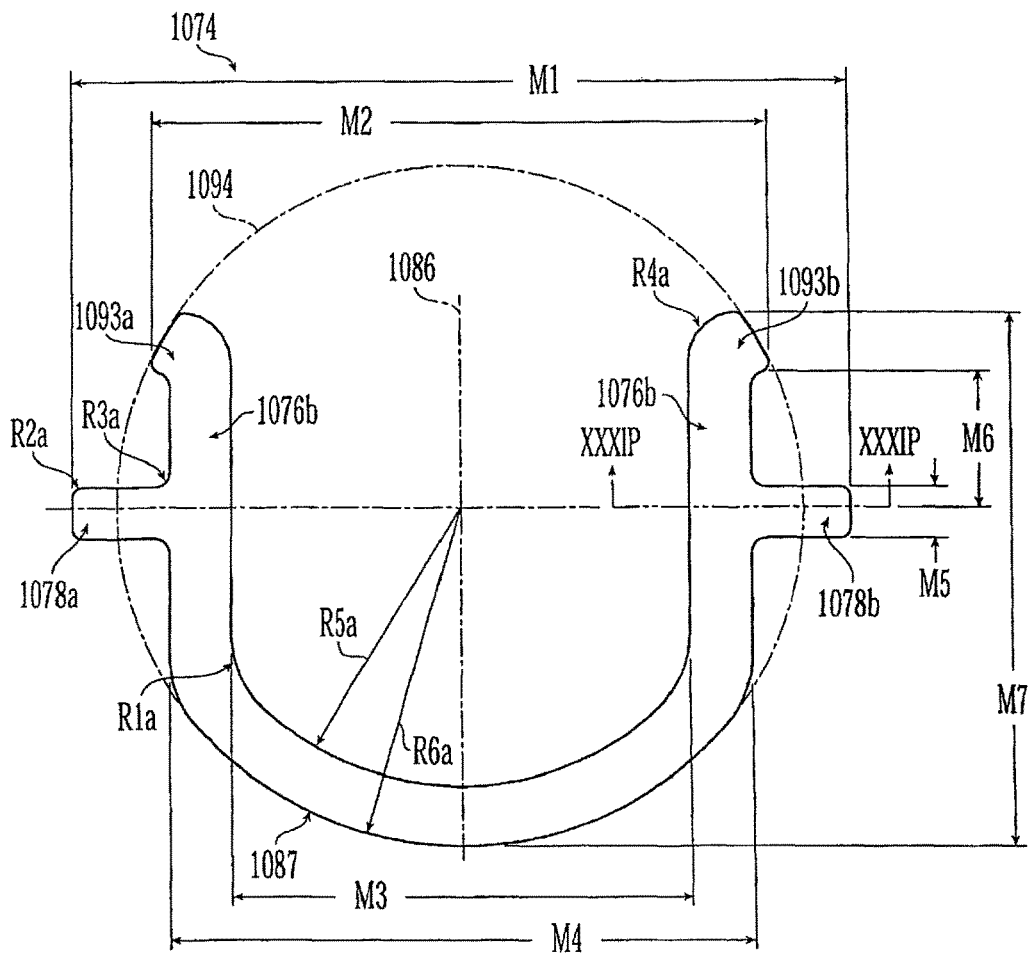
FIG. 31O shows a top view of another embodiment of a captive clip.
Figure 31P:
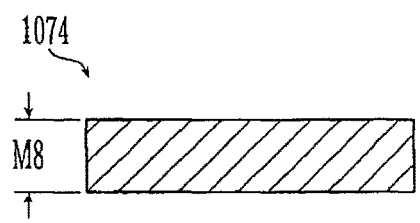
FIG. 31P shows a cross-sectional side view taken along line XXXP-XXXP of the plate of FIG. 31E.

Another embodiment of a fixation system similar to that shown in FIGS. 31A to 31D is shown in FIGS. 31E to 31P. In the "one-level" embodiment shown, a plate 1066 is provided with a pair of fixation holes 1068 that are generally "keyhole-shaped" and oblong, and a pair of fixation holes 1070 that are generally circular. An embodiment of a plate 1066b with four pairs of fixation holes 1068 and one pair of fixation holes 1070 also is shown in FIG. 31N. Thus, as described herein with respect to other embodiments, each plate may be provided with one or more pairs of oblong fixation holes and one or more pairs of circular fixation holes. Each of the circular and keyhole-shaped holes includes an undercut 1072 that receives an "omega-shaped" captive clip such as captive clip 1074, shown in FIGS. 31O to P. Captive clip 1074 includes a pair of generally parallel sides 1076a, 1076b and two end tabs 1078a, 1078b protruding from each side 1076a, 1076b, respectively. Also, captive clip 1074 includes extensions 1093a, 1093b for additional stability. As can be seen from FIG. 31O, the periphery of captive clip 1074 lies entirely within circle 1094 except portions of end tabs 1078a, 1078b, and thus captive clip 1074 is interchangeably useable with keyhole-shaped and circular holes 1068, 1070, respectively. Advantageously, captive clip 1074 may be used both with plates in which fasteners are not permitted to travel along the length of any of the holes, as well as with plates in which fasteners are allowed to move across the fixation holes.

In addition, as shown for example in FIGS. 31E and 31L, at least one passage 1085 optionally may be provided, and are used for alignment of captive clips as previously described. Thus, for example, wishbone-shaped captive clip 650 optionally may be used in at least one fixation hole 1070 in plate 1066, while "omega-shaped" captive clip 1074 optionally at the same time or instead may be used in at least one fixation hole 1068, 1070 in plate 1066. Plate 1066 therefore accommodates use of more than one design of captive clip.

A preferred exemplary embodiment of captive clip 1074 includes the following dimensions: M1 of about 7.5 mm, M2 of about 5.96 mm, M3 of about 4.4 mm, M4 of about 5.6 mm, M5 of about 0.5 mm, M6 of about 1.4 mm, and M7 of about 5.2 mm. Captive clip 1074 also has a thickness M8 of between about 0.3 mm and about 0.4 mm, more preferably about 0.35 mm. Preferred radii of curvature include: R1a of about 1 mm, R2a of about 0.1 mm, R3a of about 0.15 mm, R4a of about 0.5 mm, R5a of about 2.7 mm, and Rha of about 3.3 mm.

The geometry of fixation holes 1068, 1070 and their associated undercuts 1072 is sized such that movement of a captive clip 1074 once seated in an undercut 1072 is prevented, except that the undercuts 1072 accommodate elastic expansion of captive clip 1074 as previously explained. One tab 1078a, 1078b of captive clip 1074 is received in a hole 1080 that extends from undercut 1072 to a side of plate 1066, while the other tab 1078a, 1078b is received in a hole 1082 that extends from undercut 1072 toward the midline 1084 of plate 1066. As shown for example in FIGS. 31G and 31H, holes 1082 from adjacent undercuts of adjacent fixation holes preferably communicate with each other and may be circular in cross-section. Tabs 1078a, 1078b are used to align the "omega-shaped" captive clip 1074 in plate 1066. Preferably, captive clip 1074 is symmetrical about clip central axis 1086. Captive clip 1074 also preferably is installed in plate 1066 such that central axis 1086 is parallel to midline 1084 of plate 1066 with intermediate portion 1087 of clip 1074 oriented so as to not interfere with movement of a fastener along the length of fixation hole 1068.

The "keyhole" shaped fixation holes 1068 include a rounded portion 1088 in which a head of a fastener is received such as head 1040a of a fastener 1040. Fixation holes 1068 also include a straight portion 1089 with an integrally formed ridge 1090 that may extend about the length of straight portion 1089 and under which the head 1040a is permitted to move. Captive clips 1074 are disposed in each rounded portion.

Plate 1066 further may be provided with a slot 1091 for visualization and instrument-receiving holes 1092 for receiving a suitably configured drill guide. Slots 1091 may be any suitable shape including other shapes disclosed herein such as dog-bone shapes. In addition, for multi-level plates, the length and/or spacing of the slots may vary as shown in FIG. 31N.

The general operation of captive clip 1074 and plate 1066 is as described above with respect to FIGS. 31A to 31D.

Figure 32A:
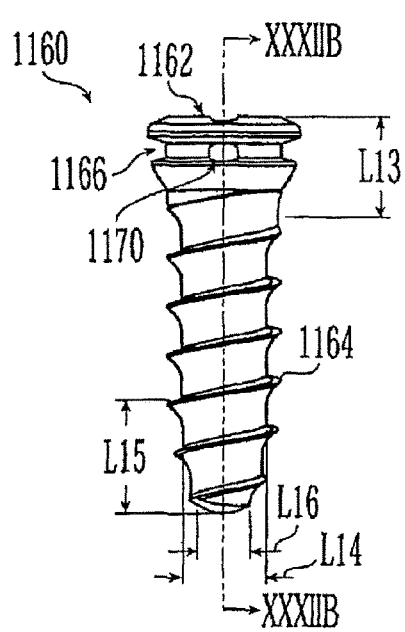
FIG. 32A shows a side view of an embodiment of a variable angle, self-tapping fastener.
Figure 32B:
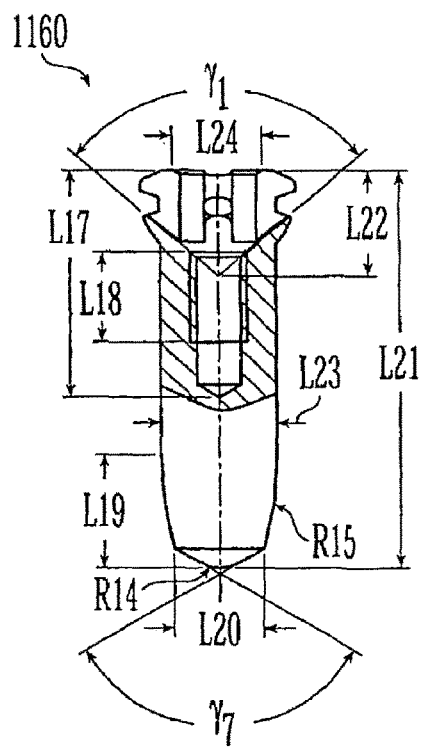
FIG. 32B shows a partial cross-sectional side view taken along line XXXIIB-XXXIIB of the fastener of FIG. 32A.
Figure 32C:
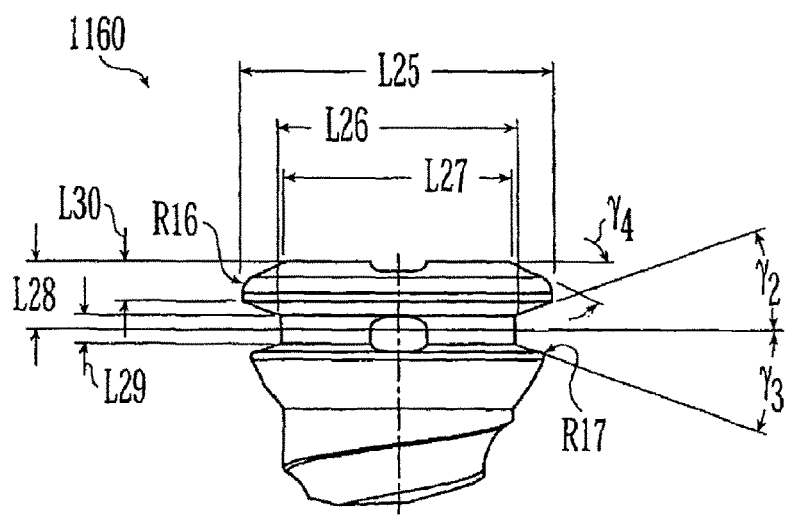
FIG. 32C shows a partial side view of the head of the fastener of FIG. 32A.
Figure 32D:
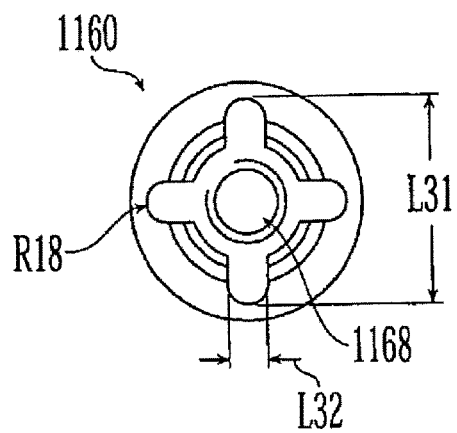
FIG. 32D shows a top view of the fastener of FIG. 32A.
Figure 32E:
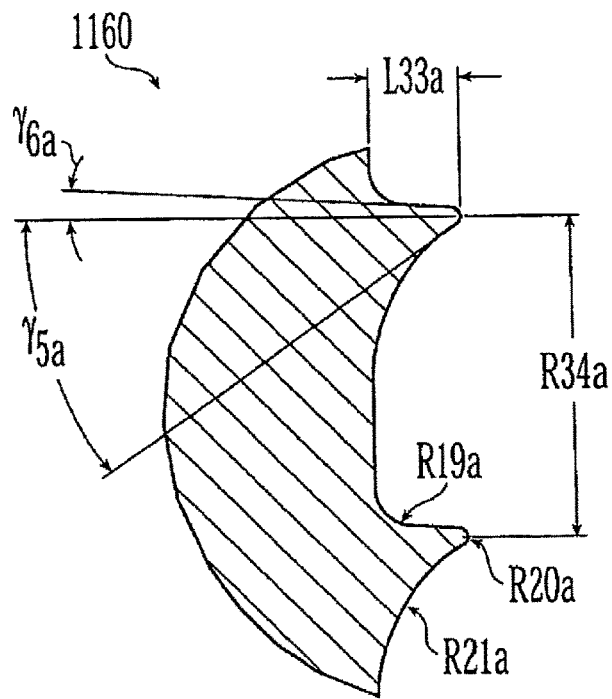
FIG. 32E shows a partial cross-sectional side view of the shaft and threads of the fastener of FIG. 32A configured and dimensioned for use with cancellous bone.
Figure 32F:
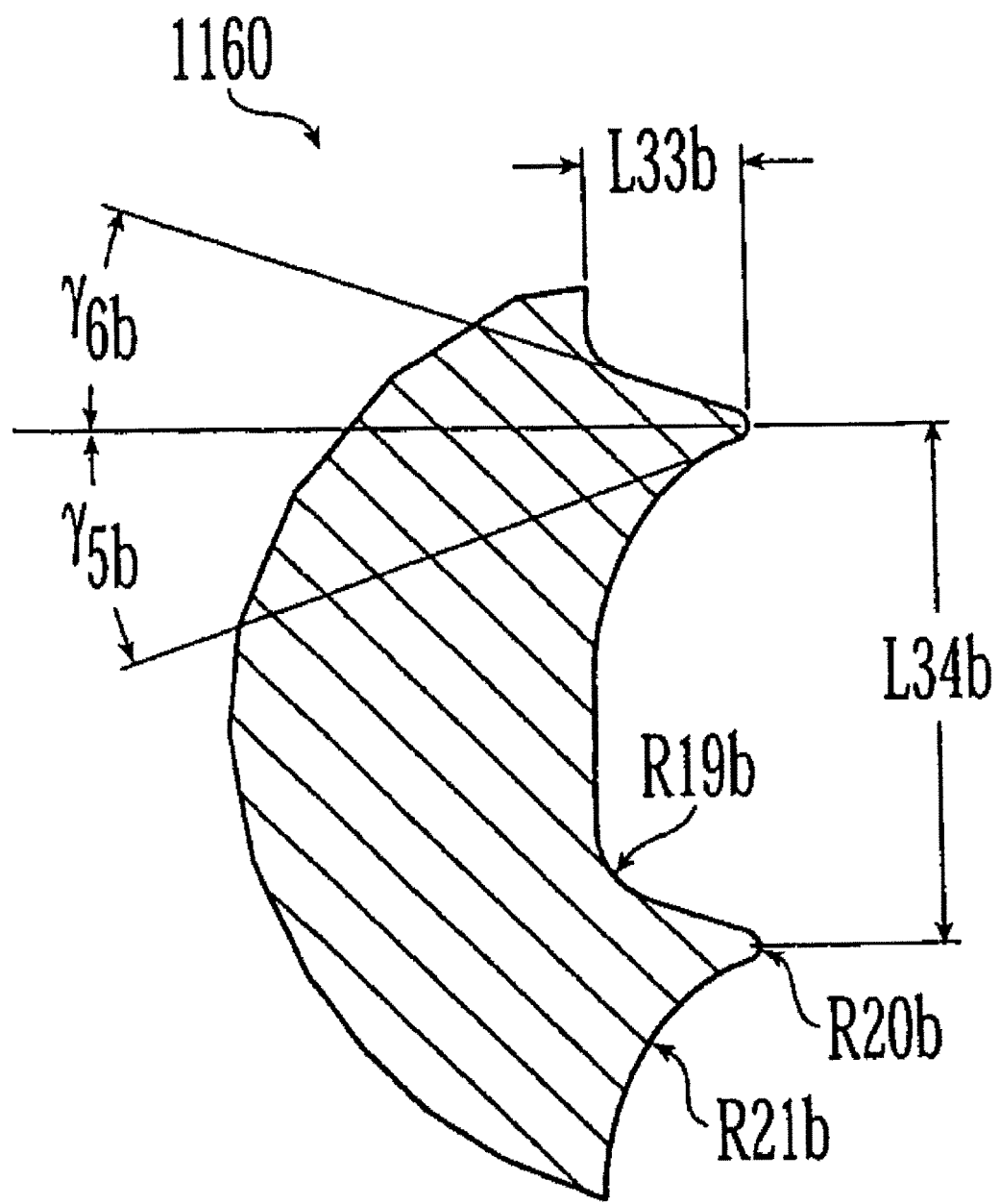
FIG. 32F shows another partial cross-sectional side view of the shaft and threads of the fastener of FIG. 32A configured and dimensioned for use with cortical bone.
Figure 33D:
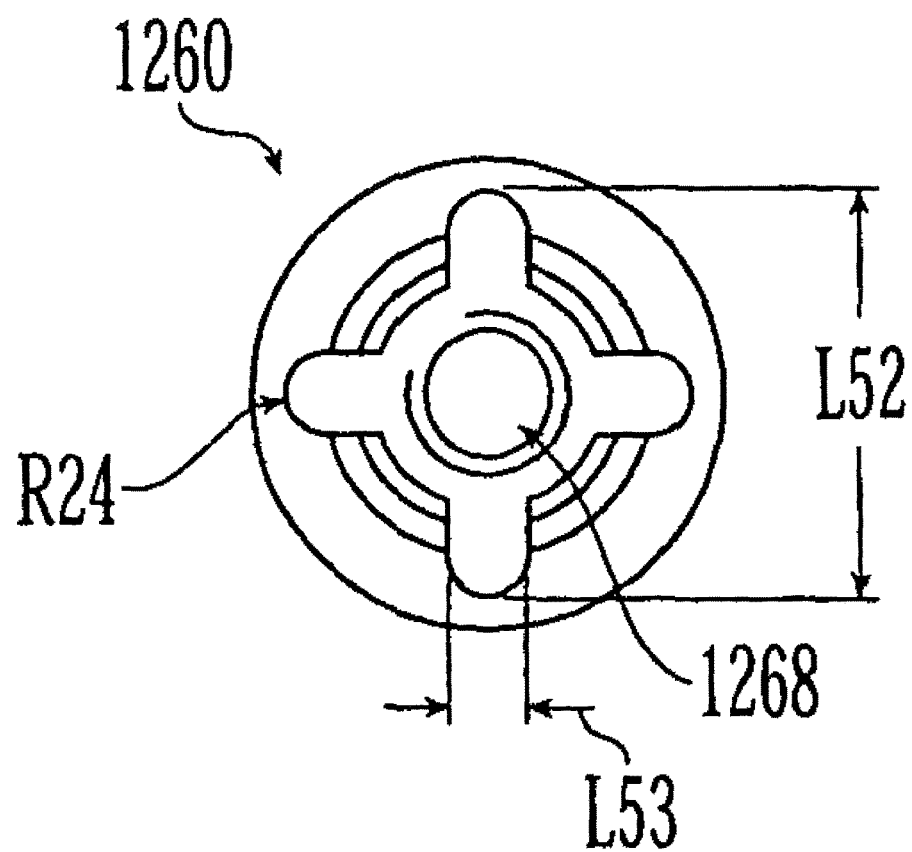
FIG. 33D shows a top view of the fastener of FIG. 33A.

Turning to FIGS. 32A to 32F, an exemplar preferred self-tapping fastener 1160 is shown preferably for use in variable angle applications. Fastener 1160 includes a head 1162 with a self-tapping, threaded shaft 1164 ending in a blunt tip 1164a. Head 1162 includes a perimetral groove 1166 extending around at least a portion thereof, and an instrument receiving portion 1168 that preferably at least partially intersects groove 1166 at one or more openings 1170. In the exemplar embodiment of FIG. 32D, instrument receiving portion 1168 is cross-shaped and thus intersects groove 1166 at four openings 1170. As shown in the figures, exemplar preferred dimensioning for self-tapping fasteners is listed in Tables I-III below. Because fasteners for use with cancellous bone differ from fasteners for use with cortical bone particularly with respect to the threads on shaft 1164, FIGS. 32E and 32F are provided for cancellous bone and cortical bone, respectively, along with appropriate dimensions in the tables below.

TABLE I

| Dimension (a-cancellous; b-cortical) | 4.0 mm and 4.5 mm Self-Tapping Fastener (°) |
| --- | --- |
| $\gamma_1$ | about 100 |
| $\gamma_2$ | about 20 |
| $\gamma_3$ | about 20 |
| $\gamma_4$ | about 25 |
| $\gamma_{5a}$ | about 35 |
| $\gamma_{5b}$ | about 20 |
| $\gamma_{6a}$ | about 3 |
| $\gamma_{6b}$ | about 20 |
| $\gamma_7$ | about 120 |

TABLE II

| Dimension (a-cancellous; b-cortical) | 4.0 mm and 4.5 mm Self-Tapping Fastener (mm) |
| --- | --- |
| R14 | about 1.4 |
| R15 | about 12.75 |
| R16 | about 0.3 |
| R17 | about 0.1 |
| R19a | about 0.2 |
| R19b | about 0.15 |
| R20a | about 0.05 |
| R20b | about 0.05 |
| R21a | about 1 |
| R21b | about 0.7 |

TABLE III

| Dimension (a-cancellous; b-cortical) | 4.0 mm Self-Tapping Fastener (mm) | 4.5 mm Self-Tapping Fastener (mm) |
| --- | --- | --- |
| L13 | about 3.9 | about 3.9 |
| L14 | about 3 | about 3 |
| L15 | about 4 | about 4 |
| L16 | about 1.84 | about 1.84 |
| L17 | about 6 | about 6 |
| L18 | about 2.6 | about 2.6 |
| L19 | about 4 | about 4 |
| L20 | about 3.1 | about 3.71 |
| L22 | about 3.67 | about 3.67 |
| L23 | about 4 | about 4.5 |
| L24 | about 3.3 | about 3.3 |
| L25 | about 5.5 | about 5.5 |
| L26 | about 4.2 | about 4.2 |
| L27 | about 4 | about 4 |
| L28 | about 1.2 | about 1.2 |
| L29 | about 0.5 | about 0.5 |
| L30 | about 0.7 | about 0.7 |
| L31 | about 5.5 | about 5 |
| L32 | about 0.8 | about 0.8 |
| L33a | about 0.5 | about 0.75 |
| L33b | about 0.5 | about 0.75 |
| L34a | about 1.75 | about 1.75 |
| L34b | about 1.25 | about 1.25 |

Dimensions particularly important for self-tapping fasteners include L15, L16, L19, L20, R14, R15, and $\gamma_7$.

Threading dimensions particularly important for fasteners used with cancellous bone include L33a, L34a, R19a, R20a, R21a, V5a, and $\gamma_{6a}$. Threading dimensions particularly important for fasteners used with cortical bone include L33b, L34b, R19b, R20b, R21b, $Y_{5b}$, and $V_{6b}$.

Turning next to FIGS. 33A to 33D, an exemplar preferred self-drilling fastener 1260 is shown preferably for use in variable angle applications. Fastener 1260 includes a head 1262 with a self-drilling, threaded shaft 1264 ending in a sharp tip 1264a. Head 1262 includes a perimetral groove 1266 extending around at least a portion thereof, and an instrument receiving portion 1268 that at least partially intersects groove 1266 at one or more openings 1270. In the exemplar embodiment of FIG. 33D, instrument receiving portion 1268 is cross-shaped and thus intersects groove 1266 at four openings 1270. As shown in the figures, exemplar preferred dimensioning for self-drilling fasteners is listed in Tables IV-VI below. As discussed previously, fasteners for use with cancellous bone differ from fasteners for use with cortical bone particularly with respect to the threads on shaft 1264. Thus, the threads and dimensions shown in FIG. 32E and provided for cancellous bone and cortical bone, respectively, also may be used with fastener 1260, along with appropriate dimensions in the tables below

TABLE IV

| Dimension (a-cancellous; b-cortical) | 4.0 mm and 4.5 mm Self-Tapping Fastener (°) |
| --- | --- |
| $\gamma_8$ | about 100 |
| $\gamma_9$ | about 50 |
| $\gamma_{10}$ | about 90 |
| $\gamma_{11}$ | about 20 |
| $\gamma_{12}$ | about 20 |
| $\gamma_{13}$ | about 25 |
| $\gamma_{16}$ | about 50 |

TABLE VI

| Dimension (a-cancellous; b-cortical) | 4.0 mm Self-Drilling Cancellous Fastener (mm) | 4.5 mm Self-Drilling Cancellous Fastener (mm) |
| --- | --- | --- |
| L35 | about 3.9 | about 3.9 |
| L36 | about 3 | about 3 |
| L37 | about 3.5 | about 3.5 |
| L38 | about 6 | about 6 |
| L39 | about 2.6 | about 2.6 |
| L40 | about 3.5 | about 3.5 |
| L41 | about 0.7 | about 1.2 |
| L42 | about 4 | about 4.5 |
| L44 | about 3.67 | about 3.67 |
| L45 | about 3.3 | about 3.3 |
| L46 | about 5.5 | about 5.5 |
| L47 | about 4.2 | about 4.2 |
| L48 | about 4 | about 4 |
| L49 | about 1.2 | about 1.2 |
| L50 | about 0.5 | about 0.5 |
| L51 | about 0.7 | about 0.7 |
| L52 | about 5 | about 5 |
| L53 | about 0.8 | about 0.8 |

Dimensions particularly important for self-drilling fasteners include L37, L40, L41, $\gamma_9$, $\gamma_{10}$, and $\gamma_{16}$.

With respect to the threaded portion of shaft 1264, the threads preferably are provided in accordance with the dimensions described previously with respect to fastener 1160 as shown in FIGS. 32E and 32F.

Turning to FIGS. 34A to 34E, another exemplar preferred self-tapping fastener 1360 is shown preferably for use in fixed-angle applications. Fastener 1360 includes a head 1362 with a self-tapping, threaded shaft 1364. Head 1362 includes a perimetral groove 1366 extending around at least a portion thereof, and an instrument receiving portion 1368 that preferably at least partially intersects groove 1366 at one or more openings 1370. In the exemplar embodiment of FIG. 34E, instrument receiving portion 1368 is cross-shaped and thus intersects groove 1366 at four openings 1370. Preferably, fastener 1360 is provided for cancellous bone.

As shown in FIGS. 34A to 34E, in one exemplary preferred embodiment, fastener 1360 is provided with dimensioning as listed in Table VII below:

TABLE VII

| Dimension | 4.0 mm Fixed Angle, Self-Tapping, Cancellous Fastener |
| --- | --- |
| L60 | about 7.5 mm |
| L61 | about 6 mm minimum |
| L62 | about 2 mm (M2 threading) |
| L63 | about 1.6 mm |
| L64 | about 2.84 mm |
| L65 | about 12 mm to about 20 mm |
| L66 | about 4 mm |
| L67 | about 3.1 mm |
| L68 | about 3.3 mm |
| L69 | about 2.8 mm |
| L70 | about 2.5 mm |
| L71 | about 2.7 mm |
| L72 | about 0.38 mm |
| L73 | about 0.7 mm |
| L74 | about 4.2 mm |
| L76 | about 4.4 mm |
| L76 | about 4.68 mm |
| L77 | about 5.12 mm |
| L78 | about 1.15 mm |

Fastener 1360 is disposed about central longitudinal axis 1372 which is oriented perpendicular to a plane that includes uppermost surface 1362a. Head 1362 preferably is provided with a first surface 1362b oriented at an angle $\sigma_4$ with respect to uppermost surface 1362a, as well as a second surface 1362c oriented at an angle $\sigma_5$ with respect to a plane 1374 disposed midway across groove 1366 and perpendicular to axis 1372. Groove 1366 is bounded at its upper and lower ends by second and third surfaces 1362c and 1362d, respectively. Preferably, third surface 1362d is oriented at an angle $\sigma_6$ with respect to a plane 1374 disposed midway across groove 1366 and perpendicular to axis 1372. A transition surface 1362e also may be disposed at an angle $\sigma_7$ with respect to axis 1372. Also, a generally flat surface 1362e connecting surfaces 1362b and 1362c preferably is oriented at an angle $\sigma_S$ with respect to axis 1372. Dimensioning for a preferred exemplary embodiment of FIGS. 34A to 34E is listed in Table VIII below:

TABLE VIII

| Dimension | 4.0 mm Fixed Angle, Self-Tapping, Cancellous Fastener |
| --- | --- |
| $\sigma_1$ | about 100° |
| $\sigma_2$ | about 120° |
| $\sigma_3$ | about 12° |
| $\sigma_4$ | about 20° |
| $\sigma_5$ | about 5° |
| $\sigma_6$ | about 20° |
| $\sigma_7$ | about 45° |
| R28 | about 12.5 mm |
| SR29 | about 1.4 mm |

With respect to the threaded portion of shaft 1364, the threads preferably are provided in accordance with the dimensions described previously with respect to fastener 1160 as shown in FIGS. 32E and 32F.

Figure 34A:
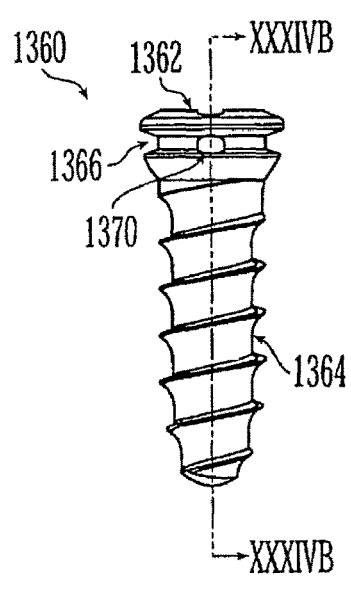
FIG. 34A shows a side view of an embodiment of a fixed angle, self-tapping fastener.
Figure 34B:
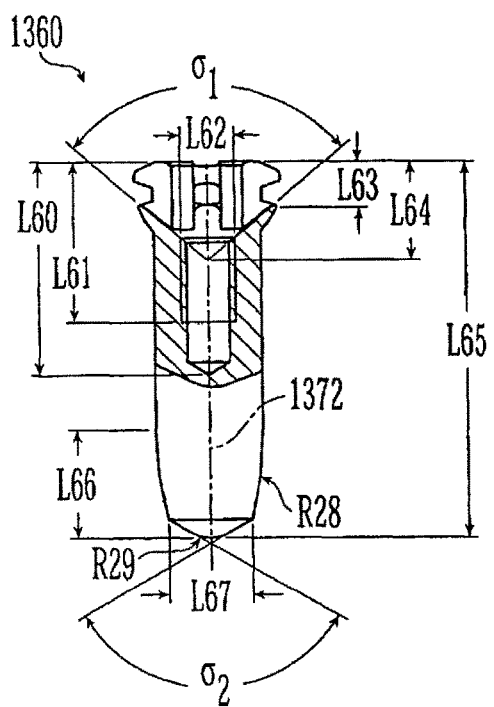
FIG. 34B shows a partial cross-sectional side view taken along line XXXIVB-XXXIVB of the fastener of FIG. 34A.
Figure 34C:
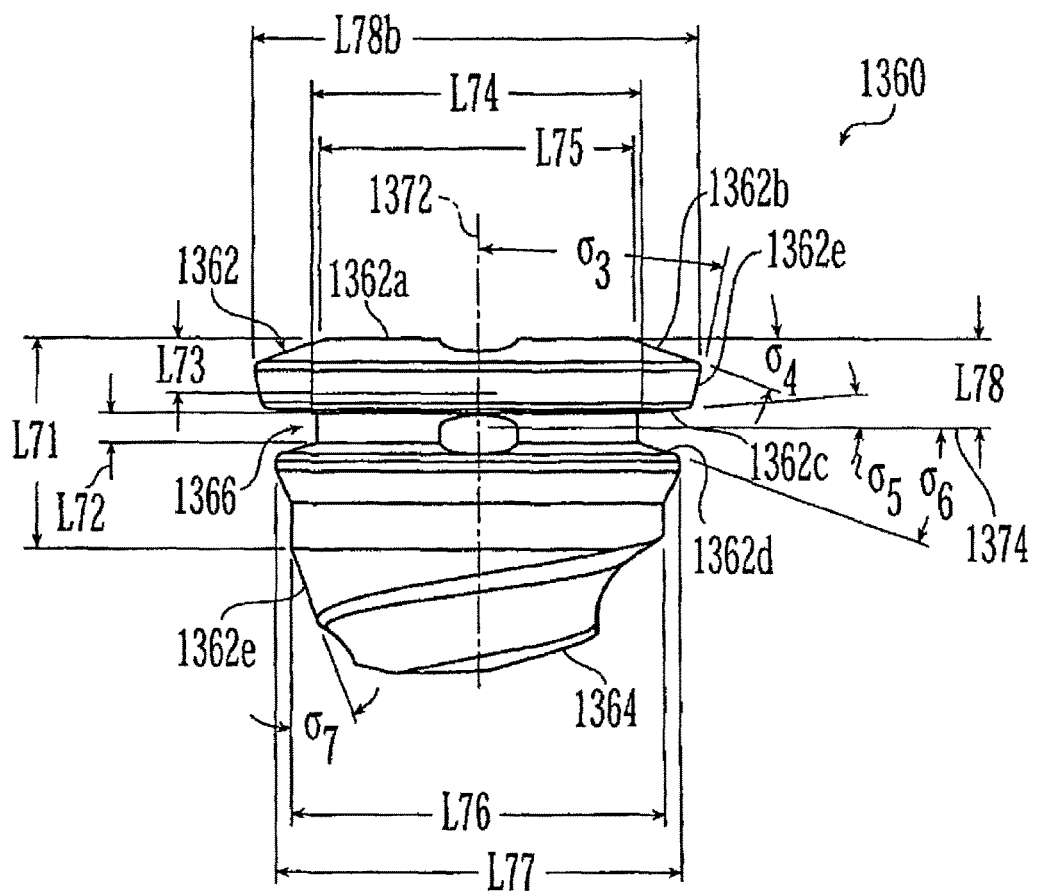
Figure 34D:
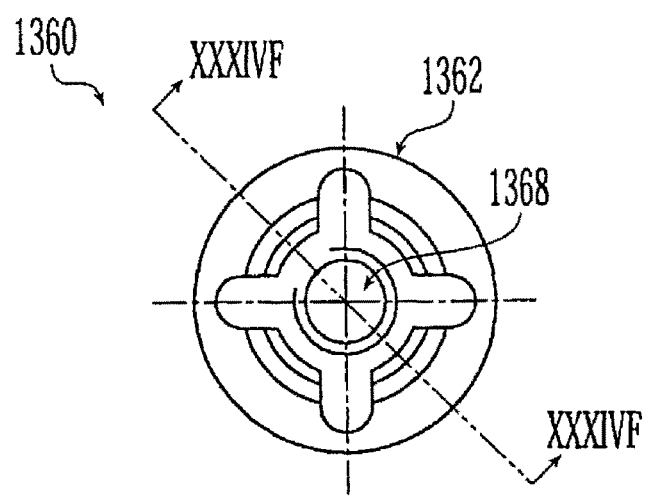
Figure 34E:
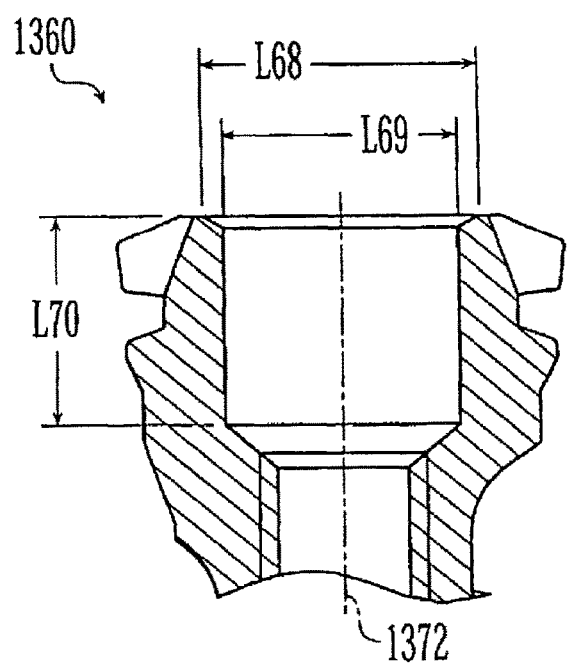

Dimensions particularly important for "fixed-angle" fasteners are shown in FIG. 34C.

As shown in FIGS. 35A to 35E, another exemplar preferred self-drilling fastener 1460 is shown preferably for use in fixed angle applications. Fastener 1460 includes a head 1462 with a self-drilling, threaded shaft 1464. Head 1462 includes a perimetral groove 1466 extending around at least a portion thereof, and an instrument receiving portion 1468 that preferably at least partially intersects groove 1466 at one or more openings 1470. In the exemplar embodiment of FIG. 35E, instrument receiving portion 1468 is cross-shaped and thus intersects groove 1466 at four openings 1470. Preferably, fastener 1460 is provided for cancellous bone.

As shown in FIGS. 35A to 35E, in one exemplary preferred embodiment, a fixed angle, self-drilling fastener 1460 is provided with dimensioning as listed in Table IX below:

TABLE IX

| Dimension | 4.0 mm Fixed Angle, Self-Tapping, Cancellous Fastener |
| --- | --- |
| L79 (internal thread) | about 7.5 mm |
| L80 (internal thread) | about 6 minimum |
| L81 | about 2 mm (M2 threading) |
| L82 | about 1.6 mm |
| L83a | about 2.84 mm |
| L83b | about 12 mm to about 20 mm |
| L84a | about 3.5 mm |
| L84b | about 0.7 mm |
| L86 | about 3.3 mm |

TABLE IX-continued

| Dimension | 4.0 mm Fixed Angle, Self-Tapping, Cancellous Fastener |
|---|---|
| L87 | about 2.8 mm |
| L88 | about 2.5 mm |
| L89 | about 2.7 mm |
| L90 | about 0.38 mm |
| L91 | about 0.7 mm |
| L92 | about 4.4 mm |
| L93 | about 4 mm |
| L94 | about 4.68 mm |
| L95a | about 5.12 mm |
| L95b | about 1.15 mm |

Fastener 1460 is disposed about central longitudinal axis 1472 which is oriented perpendicular to a plane that includes uppermost surface 1462a. Head 1462 preferably is provided with a first surface 1462b oriented at an angle $\sigma_{10b}$ with respect to uppermost surface 1462a, as well as a second surface 1462c oriented at an angle $\sigma_{10c}$ with respect to a plane 1474 disposed midway across groove 1466 and perpendicular to axis 1472. Groove 1466 is bounded at its upper and lower ends by second and third surfaces 1462c and 1462d, respectively. Preferably, third surface 1462d is oriented at an angle $\sigma_{10d}$ with respect to a plane 1474 disposed midway across groove 1466 and perpendicular to axis 1472. Also, a generally flat transition surface 1462e connecting surfaces 1462b and 1462c preferably is oriented at an angle $\sigma_{10a}$ with respect to axis 1472. Dimensioning for a preferred exemplary embodiment of FIGS. 35A to 35E is listed in Table X below:

TABLE X

| Dimension | 4.0 mm Fixed Angle, Self-Tapping, Cancellous Fastener |
|---|---|
| $\sigma_{10a}$ | about 12° |
| $\sigma_{10b}$ | about 20° |
| $\sigma_{10c}$ | about 5° |
| $\sigma_{10d}$ | about 20° |
| $\sigma_{10e}$ | about 45° |

With respect to the threaded portion of shaft 1464, the threads preferably are provided in accordance with the dimensions described previously with respect to fastener 1160 as shown in FIGS. 32E and 32F.

Some surfaces of head 1462 of fastener 1460 may be provided with features such as roughening in the form of grooves, rounded bumps, ridges, steps, serrations, etc., to provide tactile and/or audio feedback when a captive clip interacts therewith. For example, in one preferred exemplary embodiment, surfaces 1462c, 1462d, and 1462f may be provided with such roughening.

When comparing the fixed angle fastener 1360 of FIGS. 34A to 34E with the variable angle fastener 1160 of FIGS. 32A to 32F, preferably the following conditions are met: maximum shaft diameter L76>maximum shaft diameter L23; maximum head diameter L78b>maximum head diameter L25; and groove vertical width L72<groove vertical width L29.

Figure 35A:
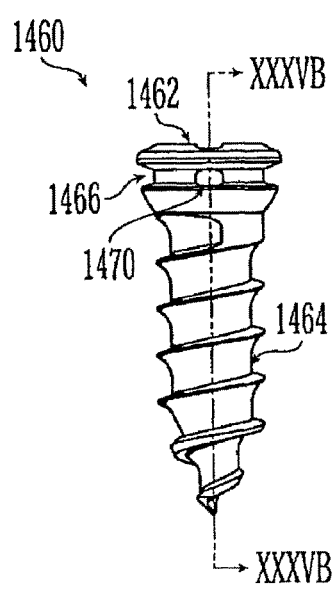
Figure 35B:
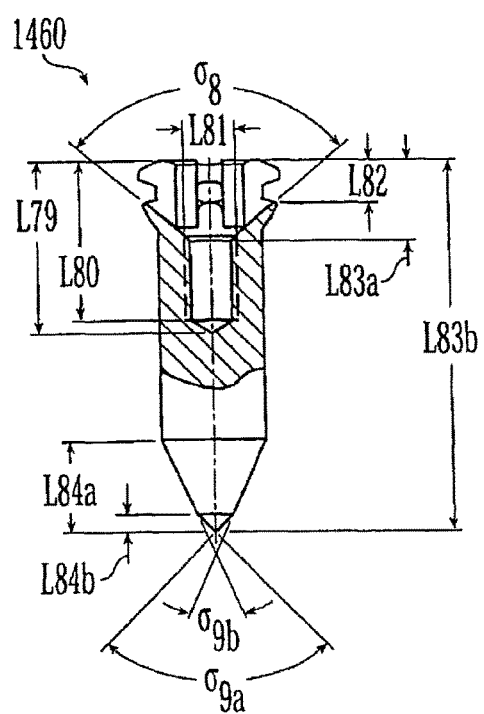
Figure 35C:
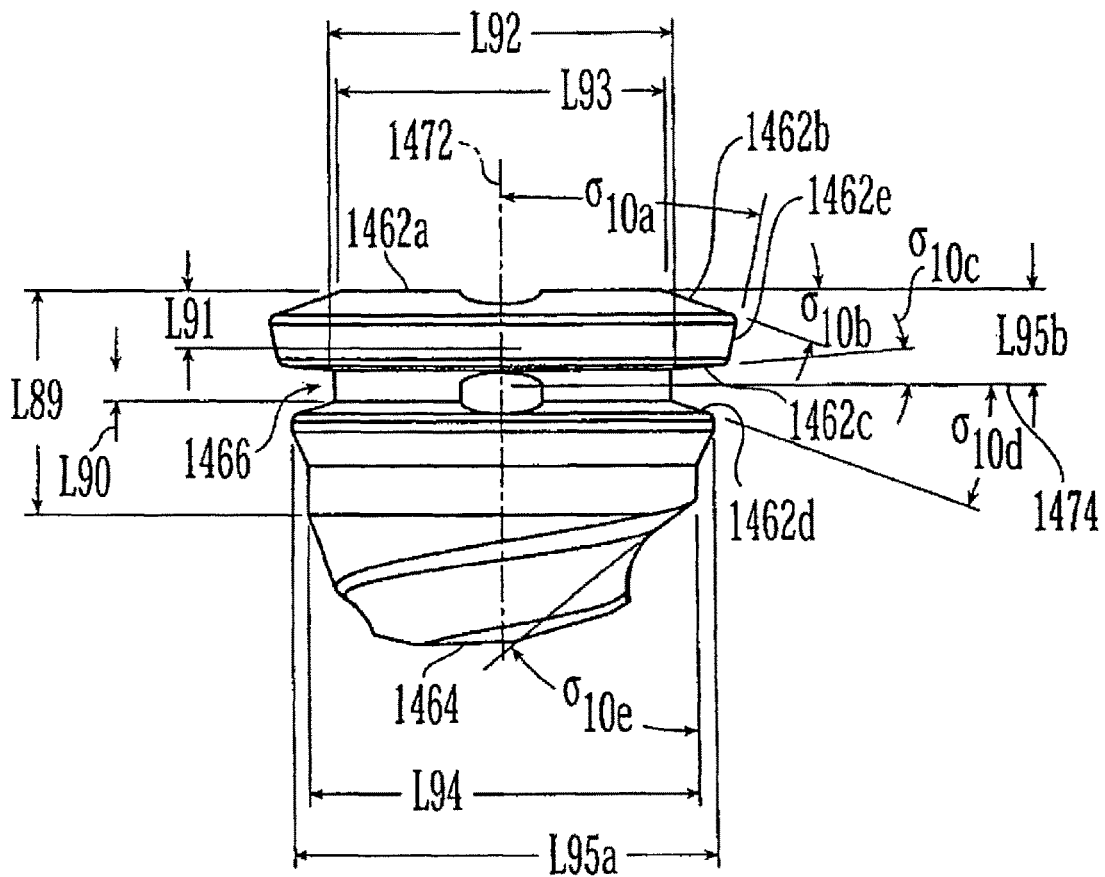

Dimensions particularly important for "fixed angle" fasteners are shown in FIG. 35C.

In yet another exemplary embodiment of an exemplary fastener 1560, shown in FIGS. 36A to 36D, head 1562 is provided with scallops 1563 so that a captive clip 1580 in a fixation plate 1582 may be visualized by a surgeon, thereby allowing the surgeon to confirm that head 1562 has been captured by captive clip 1580 to resist backout from fastener hole 1584. In one embodiment, scallops 1563 are arcuate in shape. However, other shapes may be provided as long as visualization of captive clip 1580 is permitted when fastener 1560 is coupled thereto. Preferably, four equally radially spaced scallops are provided proximate a top peripheral portion of head 1562.

Further details concerning exemplary fastener 1560 are shown in FIGS. 37A to 37F. Fastener 1560 includes a head 1562 with a self-tapping, threaded shaft 1564. Head 1562 includes a perimetral groove 1566 extending around at least a portion thereof, and an instrument receiving portion 1568 that preferably at least partially intersects groove 1566 at one or more openings 1570. In the exemplar embodiment of FIG. 37E, instrument receiving portion 1568 is cross-shaped and thus intersects groove 1566 at four openings 1570. Fastener 1560 is disposed about central longitudinal axis 1572 which is oriented perpendicular to a plane that includes uppermost surface 1562a. Preferably, fastener 1560 is provided for cancellous bone.

Figure 35D:
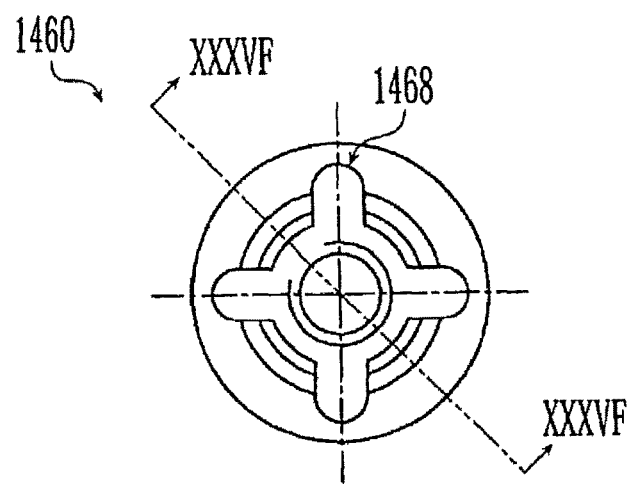
Figure 35E:
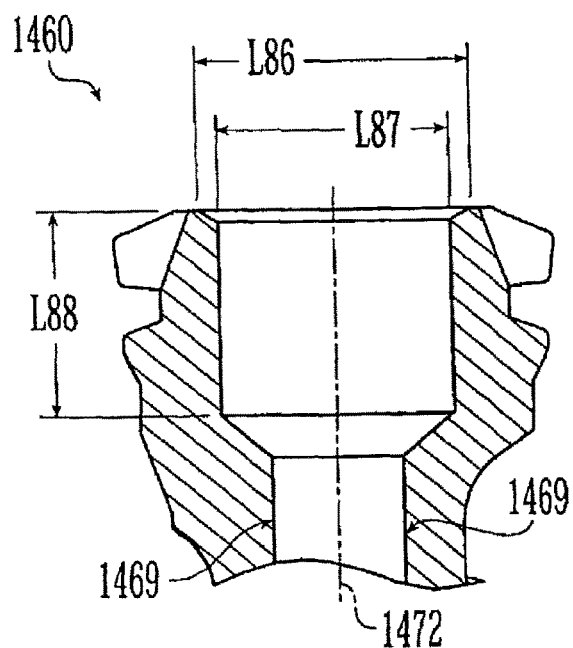
Figure 36A:
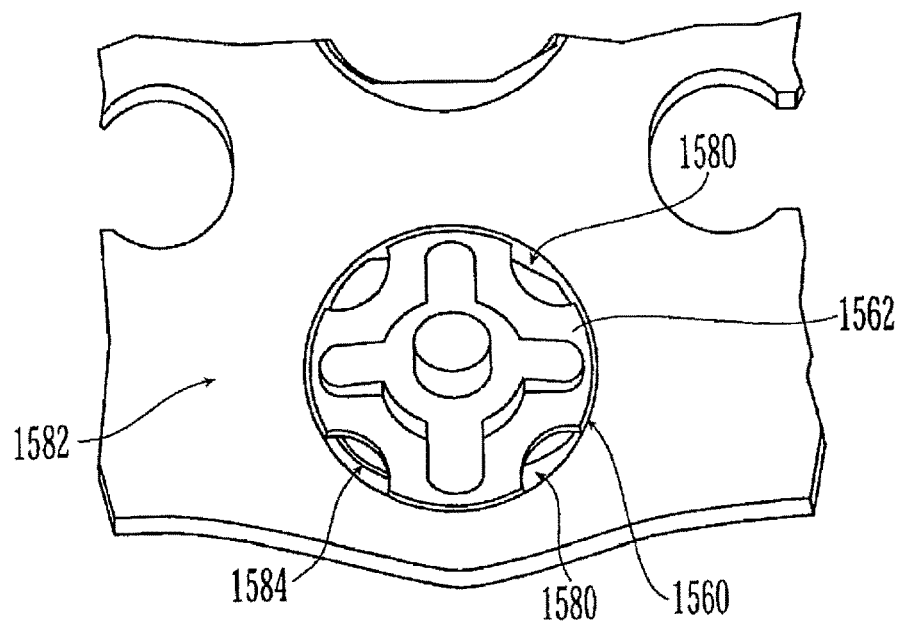
Figure 36B:
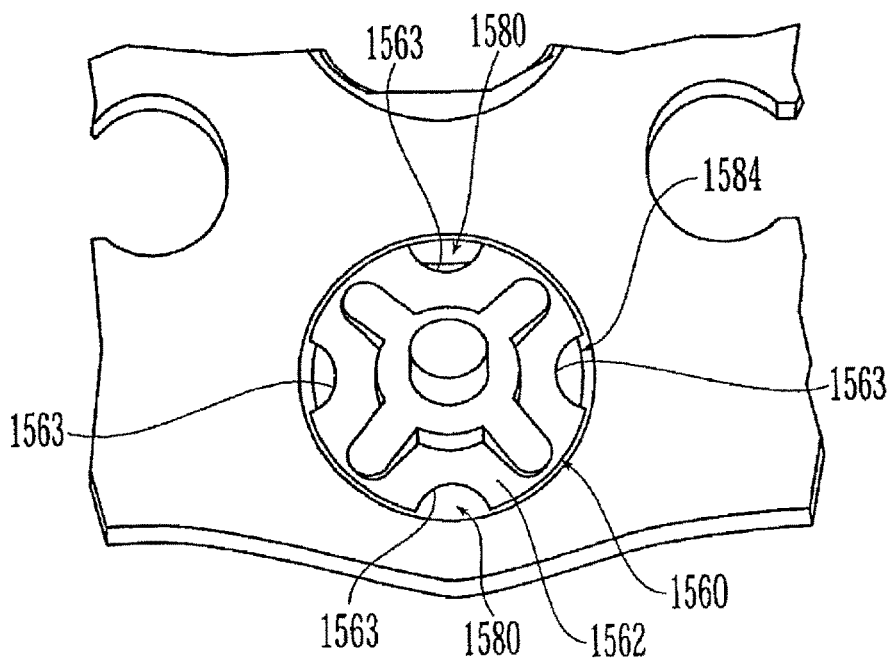
Figure 36C:
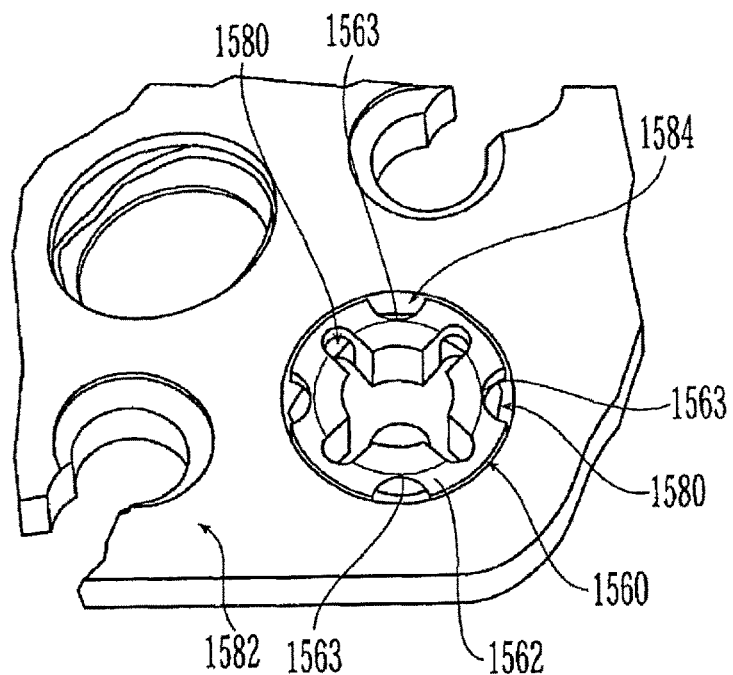
Figure 36D:
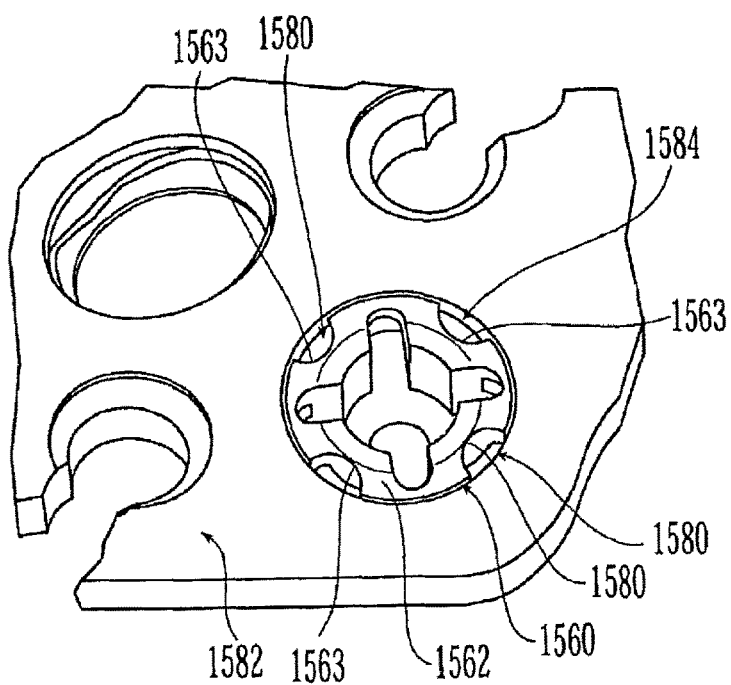

In an exemplary embodiment, the dimensioning listed in Table IX and Table X for fastener 1460, as well as the threads and dimensioning therefor as disclosed for example with respect to FIG. 35D, also are applicable to fastener 1560. As shown in FIG. 37C, however, fastener 1560 is further provided with a generally cylindrical portion 1562g disposed between surface 1562d with rounded transition 1562e and surface 1562f. Cylindrical portion 1562g may be provided with a diameter L96 of about 4.9 mm. In addition, the distance between uppermost surface 1562a and the plane defined at the intersection of rounded transition 1562e and surface 1562g may be provided with a length L97 of about 1.8 mm. Finally, surface 1562e may transition to surface 1562g at an angle $\sigma_{13}$ of between about 0° and about 45°, and more preferably about 20°. Further detail of area S in FIG. 37C is shown in FIG. 37G. Radiuses R37 and R38 of about 0.1 mm may be provided. Thus, in operation, when a fastener abuts a clip while being installed in a plate, the clip crosses from the tapered surface 1562f to the flat cylindrical surface 1562g, and then catches on surface 1562e. Such a configuration permits tactile feedback while the fastener is interacting with the clip.

As shown in FIGS. 37E and 37F, instrument receiving portion 1568 preferably has a maximum width L98 of about 5 mm and a width L99 of each section 1568a of about 1 mm. Preferably, the midway points of adjacent scallops 1563 are disposed about 90° from each other. Moreover, the midway point of each scallop 1563 is disposed at an angle $\sigma_{14}$ of about 45° from a line extending through the midway points of opposing outermost portions 1570. Tangents from rounded corners 1563a, 1563b of each scallop 1563 preferably are disposed at about 50° with respect to each other, with corners 1563a, 1563b being provided with a radius R35 of about 0.1 mm. Each scallop preferably has a radius R36 of about 0.75 mm and extends inward toward central longitudinal axis 1472 so that the radial distance L99 between the innermost portion of scallop 1563 and the central longitudinal axis 1572 may be about 2.1 mm.

Turning to FIGS. 37H to 37I, a variation of the fastener head shown in FIG. 37E is shown. In particular, scallops 1563B are each provided with a central portion 1580 having a radius R39 that is bordered by adjacent portions 1582 having a radius R40. Also, each of the portions of cross-shaped instrument receiving portion 1568B may extend to the periphery of the screw head and thus open along the upper portion thereof as shown at openings 1584.

In an exemplary preferred embodiment, each of the fasteners and fixation plates disclosed herein may be formed of a titanium alloy such as titanium-aluminum-niobium, preferably anodized. One preferred material for use with each of the plates and screws described herein is Ti-6Al-7Nb, with a density of about 4.52 gm/cc, a modulus of elasticity of about 105 GPa, an ultimate tensile strength of about 900 MPa, and a yield strength of about 800 MPa. Surfaces of the fasteners preferably also are burr free, with all sharp edges broken to a maximum of 0.1 mm.

Figure 23A:
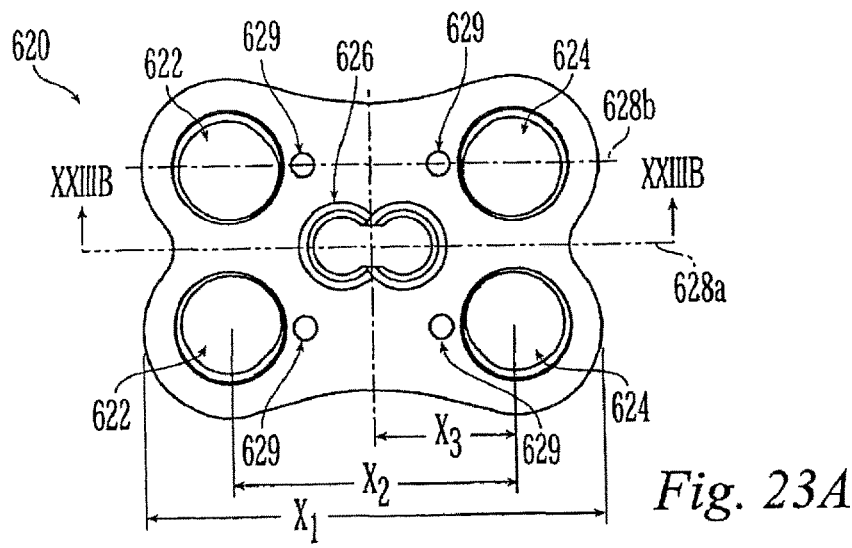
FIG. 23A shows a top view of a one level plate for use with a seventh embodiment.
Figure 23B:
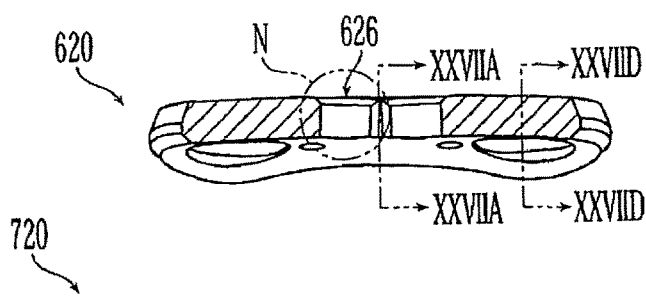
FIG. 23B shows a partial cross-sectional side view taken along line XXIIIB-XXIIIB of the plate FIG. 23A.

Each of the embodiments of plates, fasteners, and clips disclosed herein may be provided in sets or kits. For example, as shown in FIG. 23A, each of the exemplary "one-level" plates according to the present invention may be provided with maximum lengths $X_1$, lengths $X_2$ between the centers of cephalad and caudal holes, and lengths $X_3$ between the center of the plate along longitudinal axis 628a and the center of a fastener hole, as follows:

TABLE XI

| Exemplary Plate | $X_1$ | $X_2$ | $X_3$ |
|---|---|---|---|
| 1 | about 22.5 mm | about 14.0 mm | about 7.0 mm |
| 2 | about 24.5 mm | about 16.0 mm | about 8.0 mm |
| 3 | about 26.5 mm | about 18.0 mm | about 9.0 mm |
| 4 | about 28.5 mm | about 20.0 mm | about 10.0 mm |
| 5 | about 30.5 mm | about 22.0 mm | about 11.0 mm |
| 6 | about 32.5 mm | about 24.0 mm | about 12.0 mm |
| 7 | about 34.5 mm | about 26.0 mm | about 13.0 mm |

Thus, kits of plates may be provided including two or more plates, such as plates selected from exemplary plates 1-7 as listed in Table XI. For example, plates may be provided with lengths $X_1$ that differ by about 2 mm each, lengths $X_2$ that differ by about 2 mm each, and lengths $X_3$ that differ by about 1 mm each.

Figure 24A:
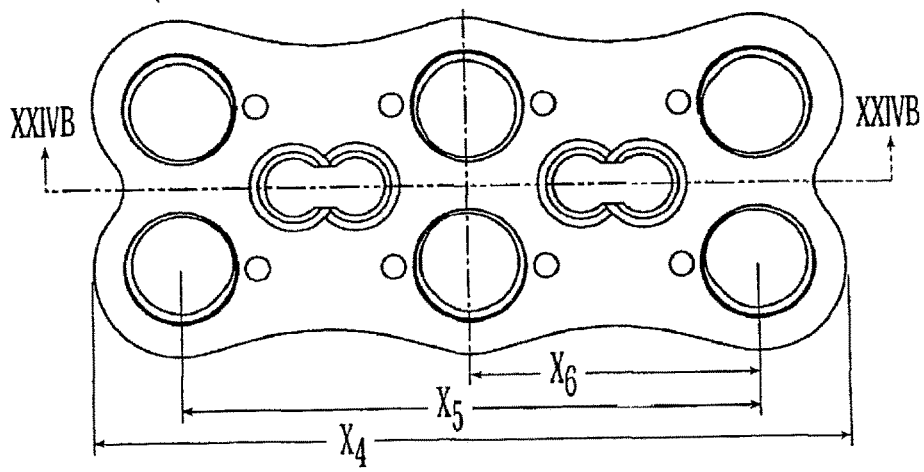
FIG. 24A shows a top view of a two level plate for use with a seventh embodiment.
Figure 24B:
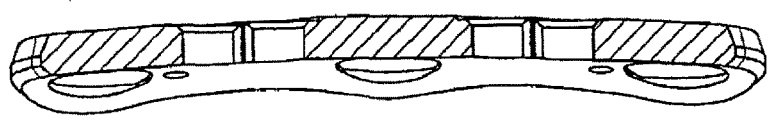
FIG. 24B shows a partial cross-sectional side view taken along line XXIVB-XXIVB of the plate FIG. 24A.

Similarly, as shown for example in FIG. 24A, each of the exemplary "two-level" plates according to the present invention may be provided with maximum lengths $X_1$, lengths $X_2$ between the centers of cephalad and caudal holes, and lengths $X_3$ between the centers of adjacent holes, as follows:

TABLE XII

| Exemplary Plate | $X_4$ | $X_5$ | $X_6$ |
|---|---|---|---|
| 8 | about 36.5 mm | about 28.0 mm | about 14.0 mm |
| 9 | about 40.5 mm | about 32.0 mm | about 16.0 mm |
| 10 | about 44.5 mm | about 36.0 mm | about 18.0 mm |
| 11 | about 48.5 mm | about 40.0 mm | about 20.0 mm |
| 12 | about 52.5 mm | about 44.0 mm | about 22.0 mm |
| 13 | about 56.5 mm | about 48.0 mm | about 24.0 mm |
| 14 | about 60.5 mm | about 52.0 mm | about 26.0 mm |

Thus, kits of plates may be provided including two or more plates, such as plates selected from exemplary plates 8-14 as listed in Table XII. For example, plates may be provided with lengths $X_4$ that differ by about 4 mm each, lengths $X_5$ that differ by about 4 mm each, and lengths $X_5$ that differ by about 2 mm each.

Figure 25A:
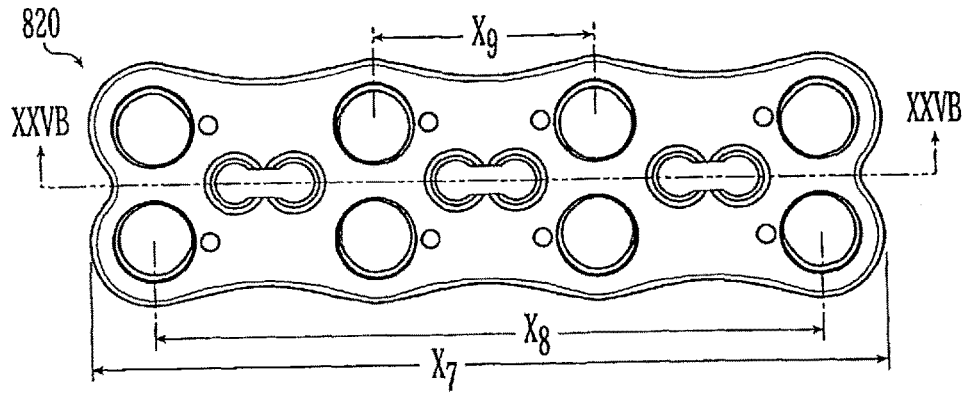
FIG. 25A shows a top view of a three level plate for use with a seventh embodiment.
Figure 25B:
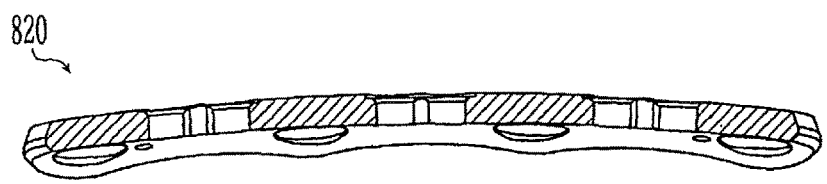
FIG. 25B shows a partial cross-sectional side view taken along line XXVB-XXVB of the plate FIG. 25A.

In addition, as shown for example in FIG. 25A, each of the exemplary "three-level" plates according to the present invention may be provided with maximum lengths $X_7$, lengths $X_8$ between the centers of cephalad and caudal holes, and lengths $X_9$ between the centers of adjacent holes, as follows:

TABLE XIII

| Exemplary Plate | $X_7$ | $X_8$ | $X_9$ |
|---|---|---|---|
| 15 | about 53.5 mm | about 45.0 mm | about 15.0 mm |
| 16 | about 56.5 mm | about 48.0 mm | about 16.0 mm |
| 17 | about 59.5 mm | about 51.0 mm | about 17.0 mm |
| 18 | about 62.5 mm | about 54.0 mm | about 18.0 mm |
| 19 | about 65.5 mm | about 57.0 mm | about 19.0 mm |
| 20 | about 68.5 mm | about 60.0 mm | about 20.0 mm |
| 21 | about 71.5 mm | about 63.0 mm | about 21.0 mm |
| 22 | about 74.5 mm | about 66.0 mm | about 22.0 mm |
| 23 | about 77.5 mm | about 69.0 mm | about 23.0 mm |

Thus, kits of plates may be provided including two or more plates, such as plates selected from exemplary plates 15-23 as listed in Table XIII. For example, plates may be provided with lengths $X_4$ that differ by about 3 mm each, lengths $X_5$ that differ by about 3 mm each, and lengths $X_6$ that differ by about 1 mm each.

Figure 26A:
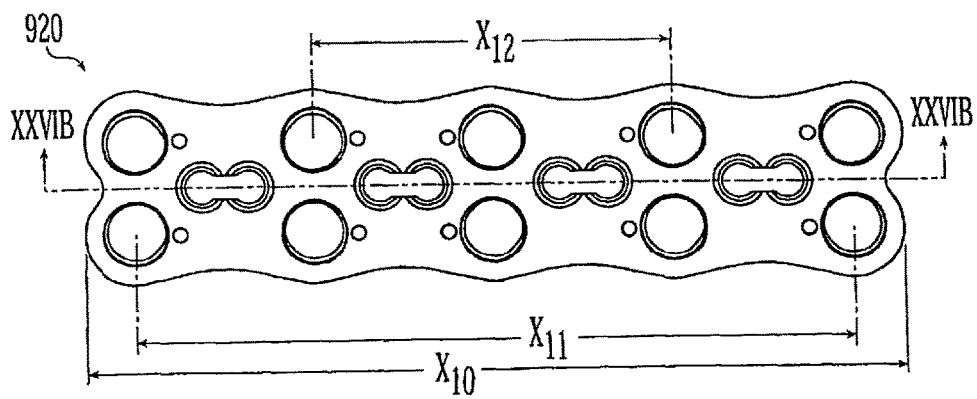
FIG. 26A shows a top view of a four level plate for use with a seventh embodiment.
Figure 26B:
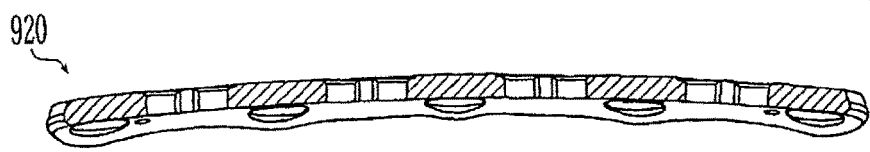
FIG. 26B shows a partial cross-sectional side view taken along line XXVIB-XXVIB of the plate FIG. 26A.
Figure 27A:
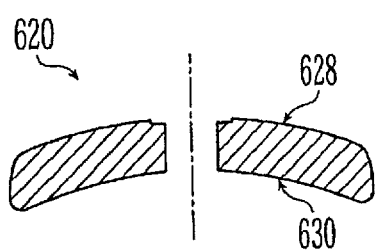
FIG. 27A shows a cross-sectional view taken along line XXVIIA-XXVIIA of the plate of FIG. 23B.
Figure 27B:
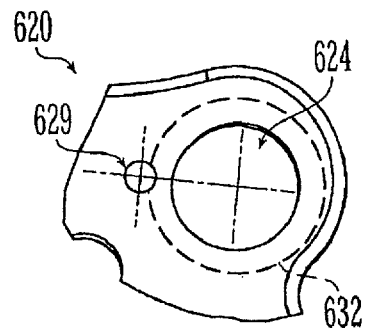
FIG. 27B shows a partial bottom view of a fixation hole and passage of the plate of FIG. 23A.
Figure 27C:
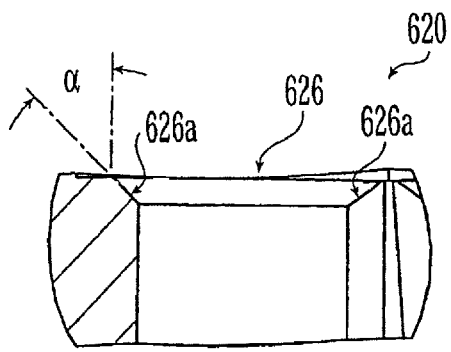
FIG. 27C shows a partial side view of a portion of the slot of the plate as indicated at detail N in FIG. 23B.
Figure 27D:
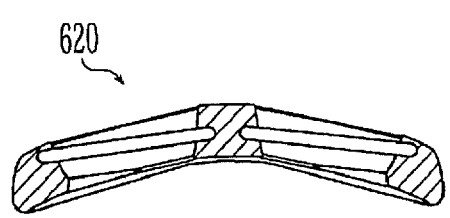
FIG. 27D shows a cross-sectional side view taken along line XXVIID-XXVIID of the plate of FIG. 23B.
Figure 27E:
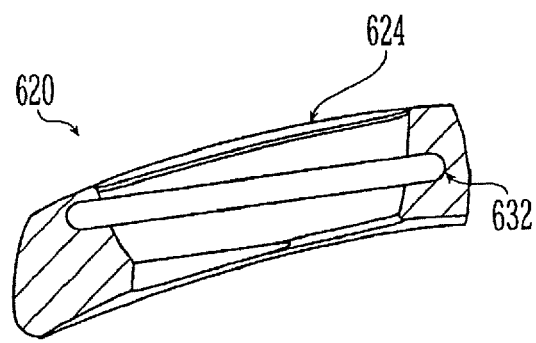
FIG. 27E shows another cross-sectional side view of one of the fixation holes taken along line XXVIID-XXVIID of the plate of FIG. 23B.

Also, as shown in FIG. 26A, each of the exemplary "four-level" plates according to the present invention may be provided with maximum lengths $X_{10}$, lengths $X_{11}$ between the centers of cephalad and caudal holes, and lengths $X_{12}$ between the centers of holes of a two-level construct, as follows:

TABLE XIV

| Exemplary Plate | $X_{10}$ | $X_{11}$ | $X_{12}$ |
|---|---|---|---|
| 24 | about 68.5 mm | about 60.0 mm | about 30.0 mm |
| 25 | about 72.5 mm | about 64.0 mm | about 32.0 mm |
| 26 | about 76.5 mm | about 68.0 mm | about 34.0 mm |
| 27 | about 80.5 mm | about 72.0 mm | about 36.0 mm |
| 28 | about 84.5 mm | about 76.0 mm | about 38.0 mm |
| 29 | about 88.5 mm | about 80.0 mm | about 40.0 mm |
| 30 | about 92.5 mm | about 84.0 mm | about 42.0 mm |
| 31 | about 96.5 mm | about 88.0 mm | about 44.0 mm |
| 32 | about 100.5 mm | about 92.0 mm | about 46.0 mm |

Thus, kits of plates may be provided including two or more plates, such as plates selected from exemplary plates 24-34 as listed in Table XIV. For example, plates may be provided with lengths $X_1$ that differ by about 4 mm each, lengths $X_2$ that differ by about 4 mm each, and lengths $X_3$ that differ by about 2 mm each.

In addition, kits with one or more plates selected from the group of "one-level", "two-level", "three-level", and "four-level" plates may be provided. Thus, a kit may optionally include one or more plates selected from exemplary plates 1-7, one or more plates selected from exemplary plates 8-14, one or more plates selected from exemplary plates 15-23, and one or more plates selected from exemplary plates 24-34, as listed in Tables XI to XIV.

In another exemplary embodiment of the present invention, an exemplary plate 1600 is provided for use without captive clips. As shown in FIGS. 38A to 38G, plate 1600 includes, fastener holes 1602 provided therein with opposed gussets 1604, 1606. Gussets 1604, 1606 serve a similar function as the clips disclosed with respect to other fixation systems described above, in that when a fastener is disposed in a hole 1602, the gussets are accommodated in groove 1610 in the head of the fastener. Thus, unlike the clips disclosed herein which may be plastically deformed to accommodate passage of the fastener and lock the fastener in place, gussets 1604, 1606 are immobile and thus do not deform. As shown in FIG. 38E, fastener 1608 may be provided with slits 1612 extending from an upper portion of head 1614 toward shaft 1616. Slits 1612 permit the head of fastener 1608 to expand and contract in a spring-like fashion, thus accommodating the decreased width of hole 1602 at gussets 1604, 1606 when fastener 1608 is installed or removed from hole 1602. In particular, fastener 1608 may be captured in hole 1602 as permitted when the head of fastener 1608 expands such that gussets 1604, 1606 are received in groove 1610. Optionally, head 1614 may be internally threaded. Advantageously, the need for a clip is eliminated in plate designs using gussets, allowing a one-piece plate construct requiring less manufacturing parts and easing assembly. Shown in FIG. 38G, the fastener 1608 is in a dynamic position; the fastener head 1614 is shown in the contracted state that occurs during insertion or removal of fastener 1608 from plate 1600. Advantageously, gussets 1604, 1606 provide the same function as described previously with respect to captive clip 680 shown in FIG. 30C.

Another embodiment of a fixation system is illustrated in FIGS. 39A-42B. FIG. 39A shows a perspective view of a plate 750 which may have a plurality of fixation holes 751, and drill guide keys 752. Fixation holes 751 may receive bone fasteners, such as fixed-angle bone screws 760 or variable-angle bone screws 770. Drill guide keys 752 may receive a portion of a drill guide (not shown), which may assist in aligning a drill barrel for more accurate use of a drill or other instrument through a fixation hole 751. Drill guide keys 752 may be a variety of shapes and sizes (including circular, triangular, elliptical, polygonal, and rectangular), and may be placed a varying or uniform distances away from fixation hole 751. Drill guide keys 752 may also be utilized for aligning a guide over more than one fixation hole 751. Plate 750 may also have windows 753, which may assist in visualization of a body tissue or bone graft below plate 750. Windows 753 may be configured, sized, and/or located such that when plate 750 is attached to a patient, at least one window 753 overlies an intervertebral disc space. Windows 753 may be a variety of shapes and sizes, including but not limited to diamond-shaped, circular, triangular, elliptical, polygonal, and rectangular. Clip 755 may also be disposed within a groove 759 (see FIG. 39D) fixation hole 751, and may engage a bone screw 760, 770 to prevent screw back-out. Clip 755 (described in more detail in below and in relation to FIG. 40), may have any or all of the characteristics or specifications of the clips described above. A top view of plate 750 is seen in FIG. 39B.

FIG. 39C shows a side view of plate 750 having a plurality of indentations 757, which may be beneficial for pre-operative bending of the plate 750 to better fit a patient's anatomy. Indentations 757 may be a variety of shapes, and may be placed at various locations along the plate 750. Although seen along the lower surface of plate 750 in FIG. 39C, indentations 757 may be placed on a variety of plate 750 surfaces, including the top surface and/or side surfaces, and/or along the perimeter of the plate 750.

FIG. 39D shows a cross-sectional view of the plate of FIG. 39C taken through the line X39-X39. As discussed above, clip 755 may be disposed within a groove 759 in a fixation hole 751. Fixation hole 751 may have tapered surfaces 758*a*, 758*b* within the inner surface of the fixation hole 751.

FIG. 40 shows a top view of another embodiment of a clip 755 for use with a variety of plates described herein. Clip 755 may be symmetrical. Clip 755 may have a notch 755*a*, and two flanges 755*b*, 755*c*. Flanges 755*b*, 755*c* may have ends 755*f*, 755*g*. Flanges 755*b*, 755*c* may also have recessed portion 755*d*, 755*e*, and a thickened portion 755*h*, 755*i*. At least a portion of clip 755, particularly the thickened portions 755*h*, 755*i*, may engage a bone fastener (such as screws 760, 770) inserted into a fixation hole 751.

Variable-angle screw 770 and fixed-angle screw 760 are shown in more detail in FIGS. 41A-42B. A side view of an embodiment of a variable-angle screw 770 is seen in FIG. 41A. Variable-angle screw 770 may have a head portion 772, a shaft 773 with at least one thread 771, and a tip 778. Head portion 772 may have a trailing ledge 774, an annular ledge 775, and a convex surface 776 extending from the annular ledge 775 to the shaft 773. Head portion 772 may also have an engaging portion 777 for receiving an instrument, such as a screwdriver. The engagement of screw 770 with a fixation hole 751 is discussed below in relation to FIG. 42A.

A side view of an embodiment of a fixed-angle screw 760 is seen in FIG. 41B. Fixed-angle screw 760 may have a head portion 762, a shaft 763 with at least one thread 761, and a tip 768. Head portion 762 may also have a trailing ledge 764, an annular ledge 765, and an annular groove disposed between the annular ledge 765 and the shaft 762. Head portion 762 may also have an engaging portion 767 for receiving an instrument, such as a screwdriver. The engagement of screw 760 with a fixation hole 751 is discussed below in relation to FIG. 428.

FIG. 42A shows a variable-angle screw 770 inserted into a fixation hole 751 of a plate 750, with a portion of the plate 750 removed for clarity. Clip 755 can be clearly seen disposed in groove 759. When variable-angle screw 770 is fully inserted into fixation hole 751, clip 755 may be disposed between trailing ledge 774 and annular ledge 775. Preferably, annular ledge 775 is sized such that after it passes below the clip 755, it may not back out of the fixation hole 751, thereby preventing overall screw 770 back-out. Convex surface 776 of screw 770 may contact tapered surface 758*a* of fixation hole 751. Tapered surface 758*a* may be concave, and thus may provide a close fit with convex surface 776. Variable-angle screw 770 may assume a variety of angulations within fixation hole 751, consistent with the discussion above.

FIG. 42B shows a fixed-angle screw 760 inserted into a fixation hole 751, with a portion of the plate 750 removed for clarity. Clip 755, along with notch 755*a* and end 755*f*, can be clearly seen disposed in groove 759. When fixed-angle screw 760 is fully inserted into fixation hole 751, clip 755 may be disposed between trailing ledge 764 and annular ledge 765. Preferably, annular ledge 765 is sized such that after it passes below the clip 755, it may not back out of the fixation hole 751, thereby preventing overall screw 760 back-out. Fixed-angle screw 760 may has a predetermined angulation within fixation hole 751, consistent with the discussion above.

FIGS. 43A-44D show embodiments of a drill guide for use, inter alia, with the system of FIG. 39A. FIG. 43A shows a side view of a variable-angle drill guide 850, which may have a barrel 851, tip portion 852, handle 853, and a connecting portion 854 for connecting the handle 853 to the barrel 851. A cross-sectional view of barrel 851 and tip portion 852 is seen in FIG. 43B. Barrel 851 may have a bore 855 which extends through the tip portion 852 as well. Bore 855, may be variably-sized along the length of the barrel 851 and/or tip portion 852. Preferably, bore 855 should be sized to receive a drill bit (not shown) or other instrument. Tip portion 852 is shown in more detail in FIG. 43C, in an enlarged cross-sectional view. Tip portion 852 may have a leading end 856. Tip portion 852 may also have an engaging portion 857 for engaging a portion of a fixation hole 851. Engaging portion 857 may be shaped and sized such that variable-angle drill guide 850 may assume a variety of angulations in relation to a fixation hole 751, thereby enabling a hole to be drilled at a variety of angulations into a bone segment beneath fixation hole 751.

FIG. 44A shows a side view of a fixed-angle drill guide 870, which may have a barrel 871, tip portion 872, handle 873, and a connecting portion 874 for connecting the handle 873 to the barrel 871. A cross-sectional view of barrel 871 and tip portion 872 is seen in FIG. 44B. Barrel 871 may have a bore 875 which extends through the tip portion 872 as well. Bore 875, may be variably-sized along the length of the barrel 871 and/or tip portion 872. Preferably, bore 875 should be sized to receive a drill bit (not shown) or other instrument. Tip portion 872 is shown in more detail in FIG. 44C, in an enlarged cross-sectional view. Tip portion 872 may have a leading end 876. Tip portion 872 may also have an engaging portion 877 for engaging a portion of a fixation hole 871. Engaging portion 877 may have a protruding ledge 878, which may be disposed immediately adjacent a clip 755 in a fixation hole 751, as seen in FIG. 44D. Engaging portion 877 may be shaped and sized such that fixed-angle drill guide 870 may only assume a predetermined angulation with a fixation hole 751. This is achieved with exemplary drill guide 870 by having a protruding ledge 878 that extends to the tapered surface 758a of fixation hole 751. The result may therefore be that tip portion 872 of fixed-angle drill guide 870 may only fit in a fixation hole 751 with a single orientation, as compared to variable-angle drill guide 850, which may assume a variety of angulations.

Drill guides 850, 870 may further have more than one barrel. Handle 853, 873 may be removably associated with a barrel 851, 871. Preferably handle 853, 873 is sized to accommodate a user's hand.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. For example, each of the plates described herein preferably are provided with curvature to conform to the spinal anatomy. In alternate embodiments, however, the plates instead may be provided without pre-lordosis. In addition, each of the plates described herein instead may be provided in embodiments that only include two fixation holes. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed:

1. A method of implanting a bone plate, the method comprising:
    positioning the bone plate adjacent a bone;
    identifying a select screw to be inserted through a hole extending through the bone plate, the select screw being selected from a group that includes a variable angle screw and a fixed angle screw, wherein:
        the variable angle screw includes a first head portion and a first shaft portion that extends from the first head portion along a first longitudinal axis, the first head portion including a first convex surface adjacent the first shaft portion; and
        the fixed angle screw including a second head portion and a second shaft portion that extends from the second head portion along a second longitudinal axis, the second head portion including a second convex surface adjacent the second shaft portion, the second convex surface extending proximally from the second shaft portion along the second longitudinal axis a distance less than a distance that the first convex surface extends proximally from the first shaft portion along the first longitudinal axis; and
    inserting the select screw through the hole and driving the screw into the bone so that 1) a resilient clip disposed within the hole is located above the first or second convex surface and 2) the first or second convex surface is seated against a tapered surface of the bone plate within the hole, wherein a central axis of the hole is one of angularly offset relative to the first longitudinal axis and parallel with the second longitudinal axis, and the resilient clip resists the select screw from backing out of the bone plate.

2. The method of claim 1, further comprising expanding the resilient clip during at least a portion of the inserting step.

3. The method of claim 2, wherein the expanding step further comprises driving the select screw through the resilient clip such that the first or second convex surface engages the resilient clip and forces expansion of the resilient clip.

4. The method of claim 3, wherein the expanding step further comprises expanding the resilient clip within an annular groove formed in the bone plate within the hole.

5. The method of claim 4, wherein the annular groove prevents the resilient clip from sliding axially within the hole.

6. The method of claim 3, wherein:
    the first head includes a first annular ledge, the first convex surface extends between the first annular ledge and the first shaft portion, the second head includes a second annular ledge, and the second convex surface extends between the second annular ledge and the second shaft portion; and
    the method further comprises allowing the resilient clip to snap inward against the first or second head portion after the corresponding first or second annular ledge is driven past the resilient clip.

7. The method of claim 6, wherein:
    the first head portion includes a first trailing ledge and a first groove formed between the first annular ledge and the first trailing ledge; and
    the second head portion includes a second trailing ledge and a second groove formed between the second annular ledge and the second trailing ledge.

8. The method of claim 6, wherein allowing the resilient clip to snap inward further comprises allowing the resilient clip to snap inward within one of the first groove and the second groove.

9. The method of claim 1, wherein driving the select screw comprises inserting a driver within a first or second receiving portion in the associated first or second head of the select screw and rotating the select screw with the driver about the associated first or second longitudinal axis of the select screw.

10. The method of claim 1, wherein:
    the inserting step further comprises inserting the variable angle screw through the hole and driving the variable angle screw into the bone at an insertion angle measured between the first longitudinal axis and the central axis so that 1) the first convex surface is seated against the tapered surface and 2) the resilient clip is disposed above the first convex surface; and the hole, the tapered surface, the first convex surface and the resilient clip are configured to permit an angle between the first longitudinal axis and the central axis to deviate from the insertion angle after inserting the variable angle screw into the bone.

11. The method of claim 10, wherein the angle between the first longitudinal axis and the central axis is permitted to deviate up to 15 degrees from the insertion angle after insertion of the variable angle screw into the bone.

12. The method of claim 11, wherein the resilient clip resists the variable angle screw from backing out of the bone plate when the angle is deviated 15 degrees from the insertion angle.

13. The method of claim 1, further comprising, prior to the inserting step, inserting a distal end of a drill guide into the hole such that a longitudinal axis of the drill guide extends at a drill angle in relation to the central axis, wherein, during the inserting step of claim 1, the select screw is inserted into the bone at the drill angle.

14. The method of claim 13, further comprising:
inserting a drill bit within an axial bore of the drill guide;
extending the drill bit through the hole; and
drilling a pilot hole in the bone at the drill angle with the drill.

15. The method of claim 14, wherein inserting the select screw through the hole and driving the select screw into the bone comprises inserting the select screw at last partially into the pilot hole.

16. The method of claim 1, wherein:
the select screw is a self-tapping screw; and
driving the screw into the bone further comprises tapping a screw hole in the bone with the self-tapping screw.

17. The method of claim 1, wherein:
the select screw is a self-drilling screw; and
driving the select screw into the bone further comprises drilling a screw hole in the bone with the self-drilling screw.

18. A method of implanting a bone plate, the method comprising:
selecting the bone plate from a kit;
positioning the bone plate adjacent a vertebral body;
identifying a select screw from the kit, the select screw being selected from a group that includes a variable angle screw and a fixed angle screw, wherein:
the variable angle screw includes a first head portion and a first shaft portion that extends from the first head portion along a first longitudinal axis, the first head portion including a first convex surface adjacent the first shaft portion; and
the fixed angle screw including a second head portion and a second shaft portion that extends from the second head portion along a second longitudinal axis, the second head portion including a second convex surface adjacent the second shaft portion, the second convex surface extending proximally from the second shaft portion along the second longitudinal axis a distance less than a distance that the first convex surface extends proximally from the first shaft portion along the first longitudinal axis; and
inserting the select screw through the hole and driving the screw into the bone so that 1) a resilient clip disposed within the hole is located above the first or second convex surface and 2) the first or second convex surface is seated against a tapered surface of the bone plate within the hole, wherein a central axis of the hole is one of angularly offset relative to the first longitudinal axis and parallel with the second longitudinal axis, and the resilient clip resists the select screw from backing out of the bone plate.

19. The method of claim 18, further comprising expanding the resilient clip during at least a portion of the inserting step.

20. The method of claim 19, wherein:
the resilient clip includes a body having a first end and a second end facing the first end and spaced from the first end; and
expanding the resilient clip further comprises increasing a distance between the first end and the second end.

* * * * *